US008663106B2

(12) United States Patent
Stivoric et al.

(10) Patent No.: US 8,663,106 B2
(45) Date of Patent: Mar. 4, 2014

(54) NON-INVASIVE TEMPERATURE MONITORING DEVICE

(75) Inventors: John Stivoric, Pittsburgh, PA (US);
David Andre, Pittsburgh, PA (US);
Christopher Kasabach, Pittsburgh, PA (US); James Hanlon, Library, PA (US);
Suresh Vishnubhatla, Wexford, PA (US); Christopher Pacione, Pittsburgh, PA (US); Scott Boehmke, Wexford, PA (US); Eric Teller, Pittsburgh, PA (US);
James Gasbarro, Fox Chapel, PA (US);
Jonathan Farringdon, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 2325 days.

(21) Appl. No.: 11/088,002

(22) Filed: Mar. 22, 2005

(65) Prior Publication Data

US 2005/0245839 A1 Nov. 3, 2005

Related U.S. Application Data

(63) Continuation-in-part of application No. 10/227,575, filed on Aug. 22, 2002, now Pat. No. 7,020,508.

(60) Provisional application No. 60/555,280, filed on Mar. 22, 2004.

(51) Int. Cl.
*A61B 5/00* (2006.01)

(52) U.S. Cl.
USPC .......................................... 600/301; 374/164

(58) Field of Classification Search
USPC ................. 600/300–301; 128/903–905, 920; 374/163–166
See application file for complete search history.

(56) References Cited

U.S. PATENT DOCUMENTS 3,830,224 A * 8/1974 Vanzetti et al. ............... 600/549
4,031,365 A 6/1977 Raggiotti et al.
(Continued)

FOREIGN PATENT DOCUMENTS

DE  19832361 A1  2/2000
DE  19911766 A1  9/2000
(Continued)

OTHER PUBLICATIONS

"Ironman Speed and Distance System" (downloaded from www.timex.com), Timex, Oct. 4, 2002.

(Continued)

*Primary Examiner* — Bill Thomson
*Assistant Examiner* — Bobby Soriano
(74) *Attorney, Agent, or Firm* — GTC Law Group LLP & Affiliates; John A. Monocello, III

(57) ABSTRACT

A monitoring system comprises a module having at least one sensor and preferably skin and ambient temperature sensors within a housing. The device may be durable or disposable. The housing may be provided with certain surface features and shapes to facilitate mounting on and interface with the skin of the wearer for more accurate temperature measurement. A receiver may be provided to obtain and display data from the module. The module may also display the output data. The output data comprises both detected and derived data relating to physiological and contextual parameters of the wearer and may be transmitted directly to a local recipient or remotely over a communications network. The system is capable of deriving and predicting the occurrence of a number of physiological and conditional states and events and reporting the same as output data.

79 Claims, 37 Drawing Sheets

(56) References Cited

U.S. PATENT DOCUMENTS

| | | | |
|---|---|---|---|
| 4,052,979 A | 10/1977 | Scherr et al. | |
| 4,129,125 A | 12/1978 | Lester et al. | |
| 4,148,304 A | 4/1979 | Mull | |
| 4,151,831 A | 5/1979 | Lester | |
| 4,192,000 A | 3/1980 | Lipsey | |
| 4,364,398 A | 12/1982 | Sassi et al. | |
| 4,377,171 A | 3/1983 | Wada | |
| 4,407,295 A | 10/1983 | Steuer et al. | |
| 4,488,558 A | 12/1984 | Simbruner et al. | |
| 4,509,531 A | 4/1985 | Ward | |
| 4,531,527 A | 7/1985 | Reinhold, Jr. et al. | |
| 4,539,994 A | 9/1985 | Baumbach et al. | |
| 4,557,273 A | 12/1985 | Stoller et al. | |
| 4,608,987 A | 9/1986 | Mills | |
| 4,622,979 A | 11/1986 | Katchis et al. | |
| 4,672,977 A | 6/1987 | Kroll | |
| 4,676,254 A | 6/1987 | Frohn | |
| 4,679,036 A * | 7/1987 | Cheng | 340/573.1 |
| 4,747,413 A * | 5/1988 | Bloch | 600/549 |
| 4,757,453 A | 7/1988 | Nasiff | |
| RE32,758 E | 10/1988 | Zartman | |
| 4,784,162 A | 11/1988 | Ricks et al. | |
| 4,803,625 A | 2/1989 | Fu et al. | |
| 4,819,860 A | 4/1989 | Hargrove et al. | |
| 4,827,943 A | 5/1989 | Bornn et al. | |
| 4,828,257 A | 5/1989 | Dyer et al. | |
| 4,883,063 A | 11/1989 | Bernard et al. | |
| 4,891,756 A | 1/1990 | Williams, III | |
| 4,917,108 A | 4/1990 | Mault | |
| 4,958,645 A | 9/1990 | Cadell et al. | |
| 4,966,154 A | 10/1990 | Cooper et al. | |
| 4,981,139 A | 1/1991 | Pfohl | |
| 5,007,427 A | 4/1991 | Suzuki et al. | |
| 5,012,411 A | 4/1991 | Policastro | |
| 5,027,824 A | 7/1991 | Dougherty et al. | |
| 5,038,792 A | 8/1991 | Mault | |
| 5,040,541 A | 8/1991 | Poppendiek | |
| 5,050,612 A | 9/1991 | Matsumura | |
| 5,072,458 A | 12/1991 | Suzuki | |
| 5,111,818 A | 5/1992 | Suzuki et al. | |
| 5,135,311 A | 8/1992 | Alpert | |
| 5,148,002 A | 9/1992 | Kuo et al. | |
| 5,178,155 A | 1/1993 | Mault | |
| 5,179,958 A | 1/1993 | Mault | |
| 5,216,599 A | 6/1993 | Uebe et al. | |
| 5,224,479 A | 7/1993 | Sekine | |
| 5,263,491 A | 11/1993 | Thornton | |
| 5,285,398 A | 2/1994 | Janik | |
| 5,305,244 A | 4/1994 | Newman et al. | |
| 5,335,664 A | 8/1994 | Nagashima | |
| 5,353,793 A | 10/1994 | Bornn | |
| 5,410,471 A | 4/1995 | Alyfuku et al. | |
| 5,416,469 A * | 5/1995 | Colling | 340/573.5 |
| 5,435,315 A | 7/1995 | McPhee et al. | |
| 5,445,149 A | 8/1995 | Rotolo et al. | |
| 5,458,123 A | 10/1995 | Unger | |
| 5,474,090 A | 12/1995 | Begun et al. | |
| 5,476,103 A | 12/1995 | Nahsner | |
| 5,484,389 A | 1/1996 | Stark et al. | |
| 5,491,651 A | 2/1996 | Janik | |
| 5,507,288 A | 4/1996 | Bocker et al. | |
| 5,511,553 A | 4/1996 | Segalowitz | |
| 5,515,858 A | 5/1996 | Myllymaki | |
| 5,515,865 A | 5/1996 | Scanlon | |
| 5,524,618 A | 6/1996 | Pottgen et al. | |
| 5,555,490 A | 9/1996 | Carroll | |
| 5,559,497 A | 9/1996 | Hong | |
| 5,564,429 A | 10/1996 | Bornn et al. | |
| 5,566,679 A | 10/1996 | Herriott | |
| 5,581,238 A | 12/1996 | Chang et al. | |
| 5,581,492 A | 12/1996 | Janik | |
| 5,583,758 A | 12/1996 | McIlroy et al. | |
| 5,611,085 A | 3/1997 | Rasmussen | |
| 5,617,477 A | 4/1997 | Boyden | |
| 5,622,180 A | 4/1997 | Tammi et al. | |
| 5,645,068 A | 7/1997 | Mezack et al. | |
| 5,663,703 A | 9/1997 | Pearlman et al. | |
| 5,666,096 A | 9/1997 | Van Zeeland | |
| 5,670,944 A | 9/1997 | Myllymaki | |
| 5,673,691 A | 10/1997 | Abrams et al. | |
| 5,673,692 A | 10/1997 | Schulze et al. | |
| 5,686,516 A | 11/1997 | Tzur | |
| 5,687,734 A | 11/1997 | Dempsey et al. | |
| 5,697,791 A | 12/1997 | Nashner et al. | |
| 5,701,894 A | 12/1997 | Cherry et al. | |
| 5,704,350 A | 1/1998 | Williams, III | |
| 5,719,743 A | 2/1998 | Jenkins et al. | |
| 5,724,025 A | 3/1998 | Tavori | |
| 5,726,631 A | 3/1998 | Lin | |
| 5,729,203 A | 3/1998 | Oka | |
| 5,730,140 A | 3/1998 | Fitch | |
| 5,738,104 A | 4/1998 | Lo et al. | |
| 5,741,217 A | 4/1998 | Gero | |
| 5,752,976 A | 5/1998 | Duffin et al. | |
| 5,771,001 A | 6/1998 | Cobb | |
| 5,778,345 A | 7/1998 | McCartney | |
| 5,778,882 A | 7/1998 | Raymond et al. | |
| 5,790,035 A * | 8/1998 | Ho | 340/573.5 |
| 5,798,907 A | 8/1998 | Janik | |
| 5,803,915 A | 9/1998 | Kremenchugsky et al. | |
| 5,813,766 A | 9/1998 | Chen | |
| 5,813,994 A | 9/1998 | Pottgen et al. | |
| 5,823,975 A | 10/1998 | Stark et al. | |
| 5,827,180 A | 10/1998 | Goodman | |
| 5,828,943 A | 10/1998 | Brown | |
| 5,832,296 A | 11/1998 | Wang et al. | |
| 5,832,448 A | 11/1998 | Brown | |
| 5,836,300 A | 11/1998 | Mault | |
| 5,839,901 A | 11/1998 | Karkanen | |
| 5,853,005 A | 12/1998 | Scanlon | |
| 5,855,550 A | 1/1999 | Lai et al. | |
| 5,857,939 A | 1/1999 | Kaufman | |
| 5,857,967 A | 1/1999 | Frid et al. | |
| 5,862,803 A | 1/1999 | Besson et al. | |
| 5,865,733 A | 2/1999 | Malinouskas et al. | |
| 5,868,669 A | 2/1999 | Iliff | |
| 5,868,671 A | 2/1999 | Mahoney | |
| 5,871,451 A | 2/1999 | Unger et al. | |
| 5,876,350 A | 3/1999 | Lo et al. | |
| 5,879,163 A | 3/1999 | Brown et al. | |
| 5,879,309 A | 3/1999 | Johnson et al. | |
| 5,884,198 A | 3/1999 | Kese et al. | |
| 5,888,172 A | 3/1999 | Andrus et al. | |
| 5,897,493 A | 4/1999 | Brown | |
| 5,899,855 A | 5/1999 | Brown | |
| 5,902,250 A | 5/1999 | Verrier et al. | |
| 5,908,396 A | 6/1999 | Hayakawa et al. | |
| 5,912,865 A | 6/1999 | Ortega | |
| 5,913,310 A | 6/1999 | Brown | |
| 5,919,141 A | 7/1999 | Money et al. | |
| 5,929,782 A | 7/1999 | Stark et al. | |
| 5,931,791 A | 8/1999 | Saltzstein et al. | |
| 5,933,136 A | 8/1999 | Brown | |
| 5,941,837 A | 8/1999 | Amano et al. | |
| 5,951,300 A | 9/1999 | Brown | |
| 5,956,501 A | 9/1999 | Brown | |
| 5,959,529 A | 9/1999 | Kail et al. | |
| 5,959,611 A | 9/1999 | Smailagic et al. | |
| 5,960,380 A | 9/1999 | Flentov et al. | |
| 5,960,403 A | 9/1999 | Brown | |
| 5,976,083 A | 11/1999 | Richardson et al. | |
| 6,032,119 A | 2/2000 | Brown et al. | |
| 6,047,203 A | 4/2000 | Sackner et al. | |
| 6,053,872 A | 4/2000 | Mohler | |
| 6,059,692 A | 5/2000 | Hickman | |
| 6,067,468 A | 5/2000 | Korenman et al. | |
| 6,091,973 A | 7/2000 | Colla et al. | |
| 6,101,407 A | 8/2000 | Groezinger | |
| 6,101,478 A | 8/2000 | Brown | |
| 6,126,595 A | 10/2000 | Amano et al. | |
| 6,135,107 A | 10/2000 | Mault | |
| 6,138,079 A | 10/2000 | Putnam | |
| 6,154,668 A | 11/2000 | Pedersen et al. | |
| 6,168,563 B1 | 1/2001 | Brown | |

(56) References Cited

U.S. PATENT DOCUMENTS

| | | | | |
|---|---|---|---|---|
| 6,184,797 | B1 | 2/2001 | Stark et al. | |
| 6,198,394 | B1 | 3/2001 | Jacobsen et al. | |
| 6,200,250 | B1* | 3/2001 | Janszen | 493/383 |
| 6,208,900 | B1 | 3/2001 | Ecker et al. | |
| 6,220,750 | B1* | 4/2001 | Palti | 374/164 |
| 6,225,901 | B1 | 5/2001 | Kail, IV | |
| 6,225,980 | B1 | 5/2001 | Weiss et al. | |
| 6,247,647 | B1 | 6/2001 | Courtney et al. | |
| 6,248,065 | B1 | 6/2001 | Brown | |
| 6,251,048 | B1 | 6/2001 | Kaufman | |
| 6,265,978 | B1 | 7/2001 | Atlas | |
| 6,266,623 | B1 | 7/2001 | Vock et al. | |
| 6,285,897 | B1 | 9/2001 | Kilcoyne et al. | |
| 6,287,252 | B1 | 9/2001 | Lugo | |
| 6,290,646 | B1 | 9/2001 | Cosentino et al. | |
| 6,290,650 | B1 | 9/2001 | Butterfield et al. | |
| 6,292,698 | B1 | 9/2001 | Duffin et al. | |
| 6,298,218 | B1 | 10/2001 | Lowe et al. | |
| 6,302,844 | B1 | 10/2001 | Walker et al. | |
| 6,306,088 | B1 | 10/2001 | Krausman et al. | |
| 6,312,363 | B1 | 11/2001 | Watterson et al. | |
| 6,315,719 | B1 | 11/2001 | Rode et al. | |
| 6,336,900 | B1 | 1/2002 | Alleckson et al. | |
| 6,339,720 | B1 | 1/2002 | Anzellini et al. | |
| 6,341,229 | B1 | 1/2002 | Akiva | |
| 6,364,834 | B1 | 4/2002 | Reuss et al. | |
| 6,366,871 | B1 | 4/2002 | Geva | |
| 6,368,287 | B1 | 4/2002 | Hadas | |
| 6,371,123 | B1 | 4/2002 | Stark et al. | |
| 6,377,162 | B1 | 4/2002 | Delestienne et al. | |
| 6,385,473 | B1 | 5/2002 | Haines et al. | |
| 6,416,471 | B1 | 7/2002 | Kumar et al. | |
| 6,450,922 | B1 | 9/2002 | Henderson et al. | |
| 6,450,953 | B1 | 9/2002 | Place et al. | |
| 6,454,708 | B1 | 9/2002 | Ferguson et al. | |
| 6,466,232 | B1 | 10/2002 | Newell et al. | |
| 6,468,222 | B1 | 10/2002 | Mault et al. | |
| 6,478,736 | B1 | 11/2002 | Mault | |
| 6,494,829 | B1 | 12/2002 | New, Jr. et al. | |
| 6,513,532 | B2 | 2/2003 | Mault et al. | |
| 6,514,200 | B1* | 2/2003 | Khouri | 600/300 |
| 6,527,711 | B1 | 3/2003 | Stivoric et al. | |
| 6,532,381 | B2 | 3/2003 | Bayer et al. | |
| 6,539,336 | B1 | 3/2003 | Vock et al. | |
| 6,547,745 | B1 | 4/2003 | Rubinstein | |
| 6,551,251 | B2 | 4/2003 | Zuckerwar et al. | |
| 6,553,251 | B1 | 4/2003 | Lahdesmaki | |
| 6,558,320 | B1 | 5/2003 | Causey et al. | |
| 6,569,094 | B2 | 5/2003 | Suzuki | |
| 6,571,200 | B1 | 5/2003 | Mault | |
| 6,584,344 | B2 | 6/2003 | Hannula | |
| 6,595,929 | B2 | 7/2003 | Stivoric et al. | |
| 6,597,944 | B1 | 7/2003 | Hadas | |
| 6,605,038 | B1 | 8/2003 | Teller et al. | |
| 6,607,484 | B2 | 8/2003 | Suzuki | |
| 6,610,012 | B2 | 8/2003 | Mault | |
| 6,656,125 | B2 | 12/2003 | Misczynski et al. | |
| 6,665,559 | B2 | 12/2003 | Rowlandson | |
| 6,690,959 | B2 | 2/2004 | Thompson | |
| 6,712,615 | B2 | 3/2004 | Martin | |
| 6,734,802 | B2 | 5/2004 | Halleck et al. | |
| 6,755,795 | B2 | 6/2004 | Marmaropoulos et al. | |
| 6,790,178 | B1 | 9/2004 | Mault et al. | |
| 6,808,473 | B2 | 10/2004 | Hisano et al. | |
| 6,817,979 | B2 | 11/2004 | Nihtila et al. | |
| 6,842,877 | B2 | 1/2005 | Robarts et al. | |
| 6,852,085 | B2 | 2/2005 | Rubinstein | |
| 6,874,127 | B2 | 3/2005 | Newell et al. | |
| 6,886,978 | B2 | 5/2005 | Tokita et al. | |
| 6,920,348 | B2 | 7/2005 | Vasin et al. | |
| 6,942,615 | B2 | 9/2005 | Suzuki | |
| 6,959,259 | B2 | 10/2005 | Vock et al. | |
| 6,968,375 | B1 | 11/2005 | Brown | |
| 7,092,846 | B2 | 8/2006 | Vock et al. | |
| 7,144,151 | B2 | 12/2006 | Saaski et al. | |
| 7,167,743 | B2 | 1/2007 | Heruth et al. | |
| 7,171,331 | B2 | 1/2007 | Vock et al. | |
| 7,198,600 | B2* | 4/2007 | Tamaki et al. | 600/300 |
| 7,330,818 | B1 | 2/2008 | Ladocsi et al. | |
| 7,676,384 | B2 | 3/2010 | Baker et al. | |
| 7,785,266 | B2* | 8/2010 | Fraden | 600/549 |
| 2001/0029340 | A1 | 10/2001 | Mault et al. | |
| 2001/0032059 | A1 | 10/2001 | Kelly, Jr. et al. | |
| 2001/0044581 | A1 | 11/2001 | Mault | |
| 2001/0044588 | A1* | 11/2001 | Mault | 600/549 |
| 2001/0049470 | A1 | 12/2001 | Mault et al. | |
| 2001/0056229 | A1 | 12/2001 | Cosentino et al. | |
| 2002/0019296 | A1 | 2/2002 | Freeman et al. | |
| 2002/0019586 | A1 | 2/2002 | Teller et al. | |
| 2002/0019615 | A1* | 2/2002 | Roe et al. | 604/361 |
| 2002/0026124 | A1 | 2/2002 | Camarero Roy et al. | |
| 2002/0027164 | A1 | 3/2002 | Mault | |
| 2002/0028995 | A1 | 3/2002 | Mault | |
| 2002/0032386 | A1 | 3/2002 | Sackner et al. | |
| 2002/0035340 | A1 | 3/2002 | Fraden et al. | |
| 2002/0055857 | A1 | 5/2002 | Mault et al. | |
| 2002/0107450 | A1 | 8/2002 | Ogura | |
| 2002/0111539 | A1 | 8/2002 | Cosentino et al. | |
| 2002/0128804 | A1 | 9/2002 | Geva | |
| 2002/0133378 | A1 | 9/2002 | Mault et al. | |
| 2002/0169427 | A1* | 11/2002 | Roe et al. | 604/361 |
| 2003/0004403 | A1* | 1/2003 | Drinan et al. | 600/301 |
| 2003/0040002 | A1 | 2/2003 | Ledley et al. | |
| 2003/0055460 | A1 | 3/2003 | Owen et al. | |
| 2003/0069510 | A1 | 4/2003 | Semler | |
| 2003/0083559 | A1 | 5/2003 | Thompson | |
| 2003/0092975 | A1 | 5/2003 | Casscells, III | |
| 2003/0152607 | A1 | 8/2003 | Mault | |
| 2003/0176797 | A1 | 9/2003 | Anzellini | |
| 2005/0032457 | A1 | 2/2005 | Gick | |
| 2005/0070778 | A1 | 3/2005 | Lackey et al. | |
| 2005/0099294 | A1* | 5/2005 | Bogner et al. | 340/540 |
| 2005/0101841 | A9 | 5/2005 | Kaylor et al. | |
| 2005/0226310 | A1 | 10/2005 | Nakazawa et al. | |
| 2006/0235280 | A1 | 10/2006 | Vonk et al. | |
| 2006/0293921 | A1 | 12/2006 | McCarthy et al. | |

FOREIGN PATENT DOCUMENTS

| | | |
|---|---|---|
| EP | 0670064 B1 | 11/1993 |
| EP | 0707825 A2 | 4/1996 |
| EP | 0880936 A3 | 3/1999 |
| GB | 2203250 A | 10/1988 |
| GB | 2322952 A | 5/1997 |
| JP | 56162022 | 12/1981 |
| JP | 2004008471 | 1/2004 |
| WO | 93/01574 | 1/1993 |
| WO | 94/25841 | 11/1994 |
| WO | 95/25946 | 9/1995 |
| WO | 97/06499 | 2/1997 |
| WO | 99/27483 | 11/1998 |
| WO | 98/59227 | 12/1998 |
| WO | 01/08554 | 2/2000 |
| WO | 00/11578 | 3/2000 |
| WO | 00/52604 | 3/2000 |
| WO | 00/26882 | 5/2000 |
| WO | 00/32098 | 6/2000 |
| WO | 00/47108 | 8/2000 |
| WO | 00/51543 | 9/2000 |
| WO | 01/28416 | 9/2000 |
| WO | 01/26535 | 10/2000 |
| WO | 01/26547 | 10/2000 |
| WO | 01/28495 | 10/2000 |
| WO | 01/39089 | 11/2000 |
| WO | 01/01093 | 1/2001 |
| WO | 01/52718 | 1/2001 |
| WO | 01/56454 | 2/2001 |
| WO | 01/82783 | 4/2001 |
| WO | 01/82789 | 5/2001 |
| WO | 01/89365 | 5/2001 |
| WO | 01/89368 | 5/2001 |
| WO | 02/69798 | 9/2002 |
| WO | 20021093272 | 11/2002 |
| WO | 2005/046433 | 5/2005 |

(56) References Cited

FOREIGN PATENT DOCUMENTS

OTHER PUBLICATIONS

"Ironman Speed Distance System—Once Again Timex Revolutionizes the Sportwatch" (downloaded from www.timex.com), Timex, Jan. 8, 2002.
Polar M91ti Heart Rate Monitor Users Manual—Quick Guide, Polar Electro Inc., Nov. 2000.
Polar USA—Product Detail—M91ti (downloaded from www.polarusa.com), Polar USA, Oct. 4, 2002.
Polar USA—Product Detail—S-610 (downloaded from www.polarusa.com), Polar USA, Oct. 4, 2002.
Georgia Tech "Smart T-Shirt," Georgia Institute of Technology Press Release, Nov. 14, 1997.
"Personal Health Monitor for Homes," Timo Tuomisto & Vesa Pentikainen, ERCIM News, No. 29, Apr. 1997.
CYBeR-CARE Internet Healthcare Technologies, BW Health Wire, Oct. 7, 1999.
"Nearer to the Heart," Brianna Krebs, Washington Post, Jan. 17, 1999.
"Portable Sensor Provides Remote Monitoring of Heart," Nikkei Weekly, Oct. 27, 1998.
"FDA Clears Datex-Ohmeda Pulse Oximeter," BW Health Wire, Dec. 3, 1998.
Estee Soft New Version of LifeConnect, Business Wire, Jan. 20, 1999.
Matsushita Home Health Check System, The Nihon Keisai Shimbun, Dec. 17, 1998.
Lightweight Ambulatory Physiological Monitoring System, Ames Research Center, Moffet Field, CA, May 22, 2002.
Warfighter Physiological Status Monitoring, MOMRP Fact Sheet No. 6, USAMRNC, 1999 (downloaded from www.momrp.org).
The H.J. Andrews Climatological Field Measurement Program, D. Henshaw, Aug. 9, 1997 (downloaded from www.fsl.orst.edu).
Weight Watchers TurnAround, Weight Watchers, 2004 (downloaded from www.weightwatchers.com).
Weight Loss Programs, Jenny Craig, 2004 (dowloaded from www.jennycraig.com).
The Complete Nutrition & Weight Management Solution Based on Your Unique Metabolic Fingerprint & Goals, BalanceLog, 2004 (downloaded from www.healthetech.com).
What is FitDay?, FitDay, 2004 (downloaded from www.fitday.com).
"A combined heart rate and movement sensor: proof of concept and preliminary testing study," K. Rennie, T. Rowsell, S.A. Jebb, D. Holburn & N.J. Wareham, 2000.
"Thermal Gap Fillers," Kent Young, Feb. 6, 2001 (article downloaded from www.chomerics.com).
Therm-A-Gap, Chomerics Technical Bulletin No. 70, Feb. 6, 2001.
"CoolPoly, the Original Thermally Conductive Polymer," Feb. 7, 2001 (article downloaded from www.coolpolymers.com).
Micro-Foil Heat Flux Sensors, RdF Corporation Catalog No. HFS-A, Mar. 1998.
Industrial Micro-Foil Heat Flux Sensor, RdF Corporation Datasheet No. HFS-B, Oct. 1995.
Industrial/Commercial Micro-Foil Heat Flux Sensor, RdF Corporation Catalog No. HFS-C, Dec. 1999.

\* cited by examiner

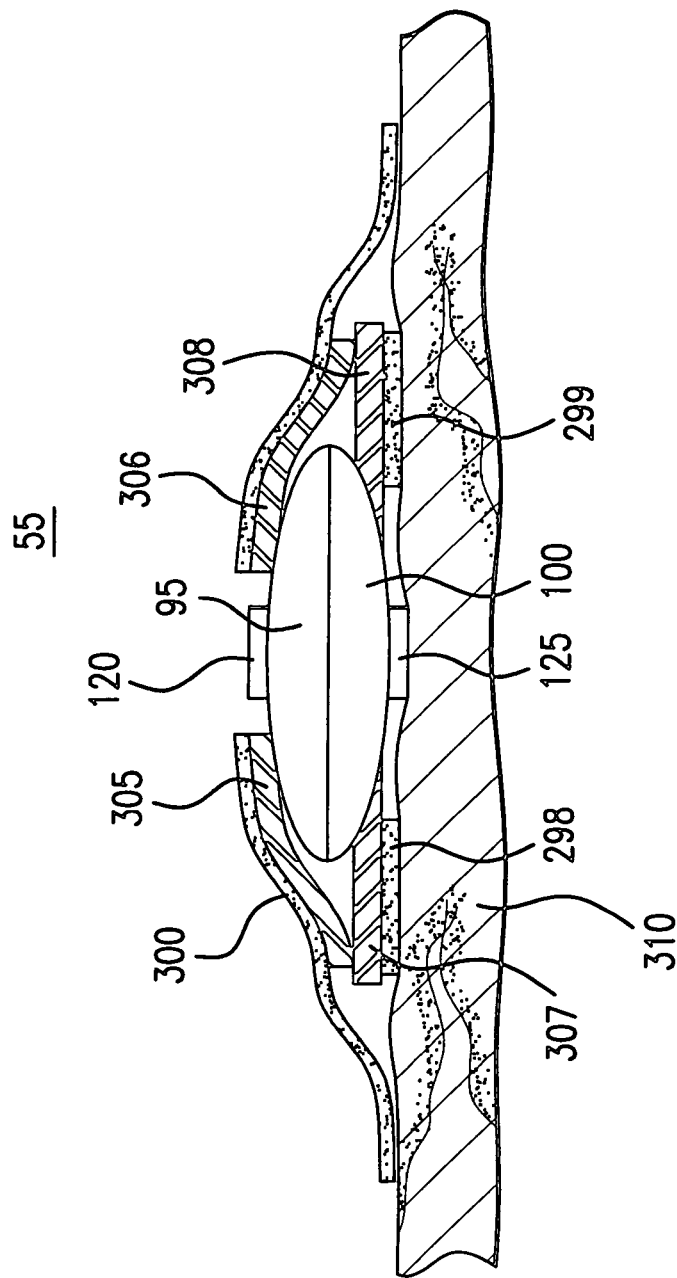

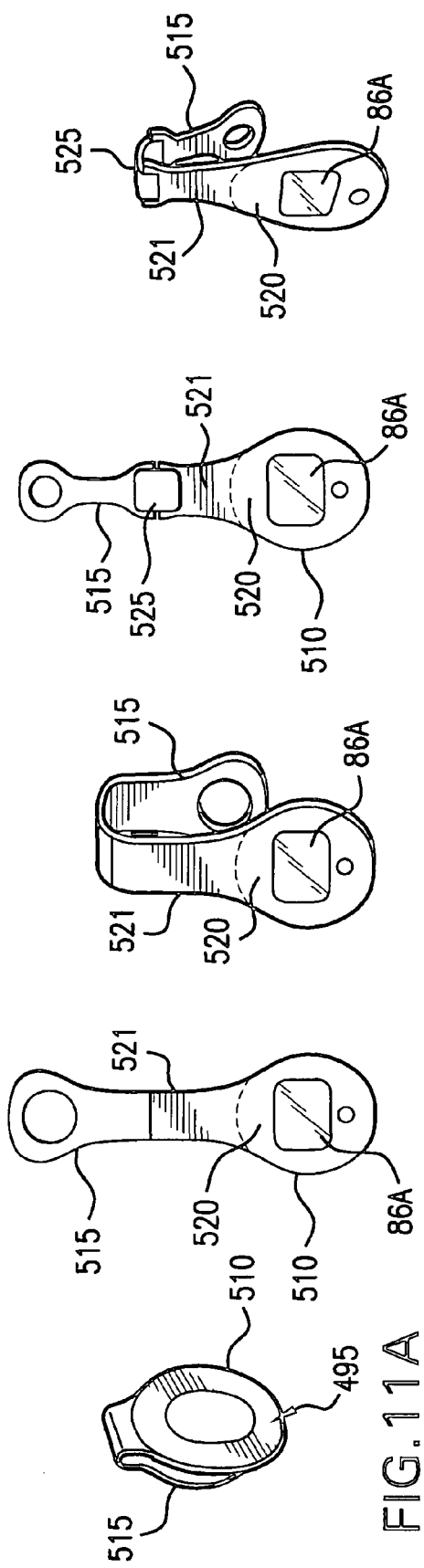

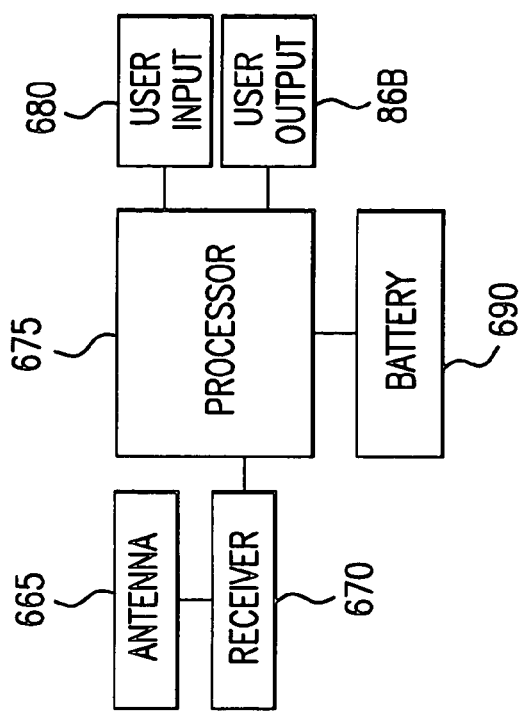
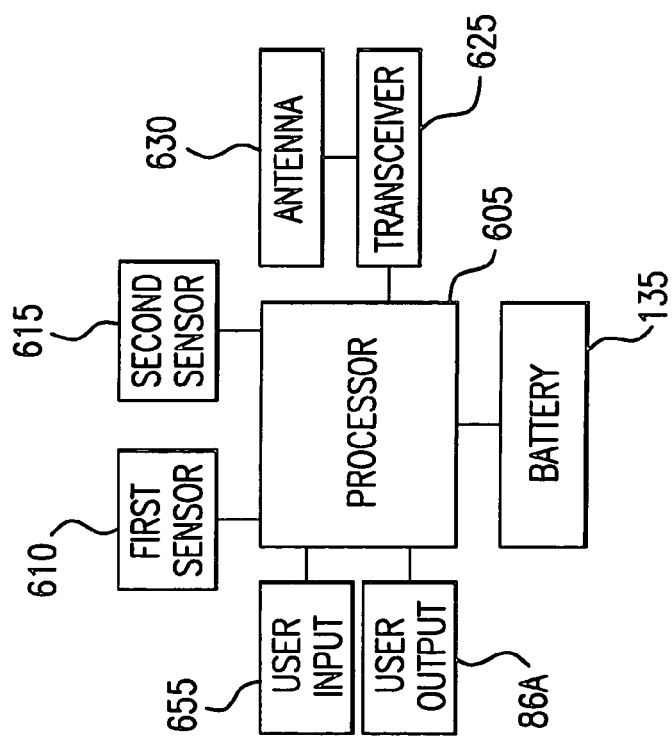

NON-INVASIVE TEMPERATURE MONITORING DEVICE

CROSS REFERENCE TO RELATED APPLICATIONS

This application is a continuation-in-part of Stivoric, et al., Apparatus for Detecting Human Physiological and Contextual Information, copending U.S. patent application Ser. No. 10/227,575 and also claims the benefit of U.S. Provisional Application No. 60/555,280, for an Automated Energy Balance System Including Iterative and Personalized Planning, Intervention and Reporting Capability, filed on Mar. 22, 2004.

FIELD OF THE INVENTION

The present invention relates to a system for continuous physiological monitoring and in particular to a system for collecting, storing, processing and displaying data primarily related to an individual's body temperature. The present invention also relates to a temperature measurement device that utilizes temperature and other detected data to derive and report additional body states, conditions and contexts. The device, while primarily intended for human use, is equally applicable to animals for veterinary or pet care.

BACKGROUND OF THE INVENTION

Core body temperature is the temperature of the vital organs of an individual. An abnormally elevated body temperature occurs when an individual is in a febrile state and can result in denaturation which is a process that causes irreversible loss of protein function, ultimately leading to cell death. An abnormally low body temperature causes an individual to be in a hypothermic state which can affect and impair the rate at which chemical reactions in the body take place and possible lead to respiratory or circulatory failure. For many years, the standard for normal or baseline body temperature has been 98.6° F., or 37° C., being the temperature at which the body is attempting to stabilize. However, research has proven that normal body temperature is actually a range of temperatures. According to the American Medical Association, normal body temperature of an individual can range from approximately 97.8° F., or 36.5° C., to 99° F., or 37.2° C. Typically, the body maintains a normal or baseline temperature generally within the narrow range of 36.5-37.5° C. Skin temperature is generally recognized as being 2-3° C. cooler than core, the actual gradient being dependent on many factors, including the ambient temperature of the environment surrounding the body and vasomotor tone. The specific normal or baseline measured temperature of an individual depends on a variety of factors. For example, time of day, recent activity, fluid and food consumption, measurement location and/or measurement technique can affect the detected body temperature of an individual. Also, normal body temperature of a group of individuals having similar demographics may vary based on these or other factors including age, metabolic rate, gender and if a disease condition is present.

Through monitoring of an individual's body temperature over time, the actual normal body temperature or range of temperatures of a specific individual can be determined. Knowing this vital statistic is important for preventing the occurrence of temperature extremes which can cause significant damage to tissues and cells of the human body. Additionally, an elevated body temperature can result in a febrile seizure, which is a brief convulsion that occurs repeatedly in association with a fever in infants and children particularly. Febrile seizures are associated with a rapid onset fever and occur in children between the ages of 6 months and 6 years of age. Although a febrile seizure does not typically result in long-term or permanent damage to the individual, there is an associated risk of bodily injury, as with any type of seizure.

True core body temperature is the temperature of the arterial blood flow from the heart and is most accurately measured at the center of the heart. Measurement at this particular location would require pulmonary artery catheterization, which is not appropriate under most circumstances due to the invasive nature of such a procedure. Consequently, body temperature measurement that provides a result closest to the blood temperature of the individual must be measured at a convenient location that is closest to core body temperature. The most widely accepted locations for measurement of body temperature are either external or externally accessible to the body or do not pose significant risk of injury to the individual. Typically, these locations include oral, axillary, rectal, and tympanic. However, the temperature measurement at any of these sites is not true core body temperature and therefore has an associated error or variance from that core body temperature, depending on the location.

One factor affecting the accuracy of temperature measurements is that different measurement locations have different rates of perfusion. Perfusion generally refers to the release of nutrient compounds needed by the cells to perform vital functions. Perfusion is further defined as the amount of arterial blood flow required to accomplish the release and distribution of nutrient compounds to the different areas of the body. Accordingly, perfusion can be correlated to factors indicative of blood flow such as blood temperature, because an area that is properly perfused has an adequate blood supply flowing through that area.

The hypothalamus of the human body attempts to maintain the body in a state of homeostasis, which is a metabolic equilibrium of the bodily functions. However, when this metabolic equilibrium is affected by ambient temperature, a hypothalamus set-point for body temperature related reactions may be triggered resulting in decreased blood flow to areas of the body. As blood flow travels farther from the heart and other vital organs, the effect of ambient temperature on the particular area of the body away from the heart is increased. For example, when the ambient temperature is lower than normal, the body will decrease peripheral blood flow to the extremities in order to maintain the homeostasis and associated core body temperature of the vital organs. The decreased peripheral blood flow is directly correlated to decreased perfusion, which leads to a lower skin temperature.

Blood supplies traveling through different areas of the body have different rates of temperature change corresponding to rising and falling body temperature. The amount of time for fluctuations in temperature to be reflected in the blood supply is largely varied among the detection locations on the body. The error or variance is also affected in large part by environmental conditions. Further, each site has error variables unique to that site that influence the measurement result.

Oral temperature is a convenient non-invasive measurement location and is an accepted equivalent for core body temperature, especially in clinical settings. The tongue has a relatively large blood flow with a temperature that mirrors that of core body temperature. However, the activity of an individual, including coughing, drinking, eating, and talking, can lower the detected temperature of the individual and produce an erroneous result. Although widely used, this method of temperature measurement depends upon proper position of the measuring device and cooperation of the patient. Recommended measurement time is three minutes to get an accurate reading.

Axillary temperature is another convenient and non-invasive site for measuring temperature. Axillary temperature can be taken externally in the armpit between two folds of skin of the armpit and arm. The accuracy of this measurement is typically dependent upon the measurement being taken relative at a location proximate to the artery on the body side. The axillary site can be adversely affected by ambient temperature in that an exceptionally cool or warm environment will produce an erroneous result. Further, the shape of the armpit affects the result because a hollow armpit is less insulated and provides increased exposure to ambient temperature of the environment. Temperatures taken in this manner tend to be 0.3 to 0.4° C. lower than corresponding temperatures taken orally. The measurement time is similar to the oral temperature technique or longer.

Rectal temperature is measured internally in the rectum. It is the least time consuming, with a typical measurement time of one minute. This is particularly important when measuring the temperature of infants, as they tend to move around, which causes additional error in the measurement. It is, however, the most uncomfortable location for measurement. The increased accuracy over oral and axillary measurements stems from the fact that the rectum is well insulated from the environment and the resulting temperature measurement is a closer match to an individual's core temperature than the temperatures measured at either the oral or axillary sites. Temperatures taken rectally tend to be 0.5 to 0.7° C. higher than corresponding temperature readings taken by mouth.

Although rectal temperature measurements are more accurate, the measurement process has associated disadvantages. This particular method poses a risk of injury to the individual because the insertion of the temperature probe into the rectum may cause perforation of the delicate tissues, in addition to the risk of infections and other illnesses stemming from lack of hygiene relating to the measurement device and/or its use. Also, rectal temperature responds more slowly than oral temperatures to changes in heat input and loss because any matter contained within the rectum acts as insulation and any rapid body temperature changes are not immediately reflected.

There are two locations in the ear which are also appropriate for temperature measurement. The first location is the external portion of the ear canal. The ear canal is a convenient, non-invasive location but is subject to significant influence by environmental conditions and the cooling effect of these conditions on the body. The second location is the tympanic membrane which is located deep inside the skull and is not subject to the same influences as the ear canal. Tympanic temperature has also become a common measurement technique in recent years. Tympanic temperature is a close reflection of core body temperature because the eardrum shares the blood supply with the hypothalamus which controls temperature. Temperature changes are reflected sooner and are more accurate. To measure the temperature at the tympanic membrane, however, a long thin thermocouple probe has to be inserted into the ear causing a great deal of discomfort to the individual. The thermocouple probe must contact or at least remain close to the very delicate tympanic membrane which entails a cooperation of the individual and a risk of injury.

A wide variety of devices and techniques are know for the measurement of body temperature, most of which are directed to static, as opposed to continuous, measurements. The most accurate devices and methodologies for temperature measurement are, unfortunately, the most invasive and include pulmonary artery/thermal dilution catheters, esophageal temperature probes and indwelling bladder and rectal temperature probes. Pulmonary artery/thermal dilution catheters are the most accurate method of temperature measurement because of the ability to continuously monitor the temperature of the pulmonary outflow of the heart. However, because these methods are invasive and impractical, other devices have been developed to more conveniently measure the temperature of an individual, even on a static basis.

The glass mercury or expanding liquid thermometer has been used to measure temperature for many years, however the accuracy of this device is questionable, in part because its accuracy significantly depends on the time at which it is properly located and the reader properly interpreting the scale. This accuracy deficiency is partially due to the limited number of locations for measurement while using the device, which include oral, axillary and rectal. Studies have revealed that glass mercury thermometers demonstrate errors on the order of 0.5° C. or 0.9° F. at normal body temperature and errors of greater magnitude when an individual is febrile. In addition, accidental breakage and disposal is cause for concern when using a glass mercury thermometer. When liquid mercury is spilled, it forms droplets that emit vapors into the air which are odorless, colorless and toxic. Because mercury is poisonous and hard to clean up if spilled, these thermometers are less common today and have actually been banned in some locations. Also, there is no ability of the device to obtain and record a history of the temperatures of an individual because only individual serial measurements are recorded on this simple measuring device. Continued long-term temperature measurement which is not continuous can be troublesome to the ill individual who must be awake for each measurement. The electronic thermometer, also called the digital thermometer, is considered more accurate than a glass mercury thermometer, but essentially provides similar functionality with a small improvement in convenience.

The chemical thermometer, designed to be a one-time use or disposable product, is a type of probe thermometer. An example of this type of thermometer is the Vicks Disposable Thermometer, Model V920. This device is a paper device with heat activated chemical dots superimposed on the surface. The dots change color based on the temperature measurement. This device provides some advantage in that it can be thrown away after its use so that germs and bacteria do not contaminate the device for continued use. However, this particular type of thermometer strip has been found to be imprecise, inaccurate, inconsistent and yields frequent false-positive results.

Many of the recent developments in the field of temperature measurement are directed toward improving comfort and convenience for the user, such as the use of a curved, rubber accessory or probe that is conformed and flexible to fit over the teeth and inside the mouth to rest more easily on the jaw to garner greater application consistency. These efforts can also be counterproductive. In one example, a pacifier-like probe is utilized to allow an infant to be monitored with a familiarly shaped device. The natural and reflexive sucking action of the infant, however, causes the signal from this device to be noisy and inaccurate. These improvements have therefore been directed toward ease of use issue but little has been accomplished in terms of increasing accuracy and consistency completely apart from technique and user error. Additionally, all of the preceding devices are directed toward static measurements. In most, if not all circumstances, these devices are entirely impractical as continuous temperature monitors for ergonomic, safety, convenience and data retention reasons.

Other newer techniques and devices include sensing diaper urine or bowel movements in a diaper, immediately after release from the body when the substance is at core temperature. The limitation is that this is entirely event driven and must be properly anticipated, in the proper location, and must be able to detect the peak temperature to record the measurement before cooling or heating up. Additional practical considerations include the need to dispose of or clean the product because the sensor/device is now soiled.

An infrared thermometer is a non-contact temperature measurement device that detects infrared energy emitted from an individual and converts the energy to an electrical signal that can be displayed as a measurement of temperature after being corrected for variation due to ambient temperature. An infrared thermometer can be used at a variety of locations and provide significant advantages. Infrared thermometers can be used to take temporal membrane measurements which have more recently been reported to have strong correlation to pulmonary arterial temperature, but have also become popular especially in infant monitoring because they don't require the measurer to disturb the infant through an orifice or under the arm, especially if frequent readings are required or prescribed to be performed. The main disadvantage of an infrared thermometer is that the device is highly dependant on the operator's technique. It can be difficult to get a consistently accurate reading without a consistent method of use. Also, the cleanliness of the infrared lens can significantly impact the results of measurement. Further, infrared thermometers typically do not account for the effects of ambient temperature on the skin temperature measurement of the individual.

In most cases, there is also the traditional trade off between cost and accuracy. This is exacerbated in this field, especially within the realm of disposable products. Disposable products are increasingly popular in light of concerns regarding hygiene. This is most applicable to institutional applications. Disposability, however, necessitates a firm cost ceiling for any product, which in turn limits the ability of the device to provide more than the most limited functionality.

In many situations, temperature readings, together with the data, diagnoses and other information extrapolated or derived from the temperature readings, would be more useful and accurate if made continuously rather than the periodic, static measurements now commonly made and described above. Several devices and techniques have been proposed to facilitate continuous measurement.

Exterior skin has traditionally not been considered an appropriate location for temperature measurement, even when measurement is taken near a surface artery. This is, in part, because skin temperature measurements suffer from significant noise from peripheral shutdown, skin insulation, activity and environmental and internal (hydration) convolutions. Even so, skin locations are much less invasive and potentially comfortable for continuous wear of a temperature monitor. These monitors can also be protected from environmental noises by clothing, diapers, attachable bands and the like.

A Wireless Thermometer manufactured in Taiwan and Japan by Funai and marketed by Granford Marketing and Management Services under a variety of trade names provides a transceiver device which is clipped onto clothing or diaper of the patient to be monitored. A sensor is mounted internal to the clip and is intended for direct contact with the skin. The device relies upon the article of clothing or diaper to maintain the contact between the skin and the sensor. The sensor records the temperature and displays the reading on an LCD screen. The transceiver device is paired to a receiver unit by wireless transmission which receives the temperature data and may be preset to sound an alarm if a certain temperature threshold is reached. No provision is made for storage of any historical data. A number of other prior art devices do provide this functionality.

Rubinstein, U.S. Pat. No. 6,852,085, issued Feb. 8, 2005, for a Fever Alarm System, discloses a continuous body temperature measurement device. The device comprises a microprocessor having two thermistors that continuously measure skin temperature and ambient room temperature for calculation of body temperature. One thermistor lies adjacent to the skin and is insulated from the surrounding environment. The second thermistor is exposed to the ambient room air and is not in contact with the skin. The device measures both skin and ambient room temperature and then transmits the calculated result through an RF transmitter to a display unit which displays the current temperature of the individual. The device further includes an adjustable alarm that is triggered when a certain predetermined temperature threshold is reached.

The device continuously measures both skin temperature and ambient temperature, and must first log a history of ambient room temperature for thirty minutes before a first result is calculated. The thirty minute delay in accounting for the ambient room temperature can be life-threatening when monitoring a febrile individual. The output of the device is a calculation, which is not based on the actual measurement history of the individual's detected temperature or on a correlation to that specific individual's physiology, physiological performance, activity and core temperature. Instead, the device obtains this information from programmable read-only memory containing tabular data of analytic values. The tabular data is derived by a process of data to data mapping in which a particular output is generated for a particular set of possible inputs. The data contained in these look-up tables is taken from previously determined experimental data of body temperature versus skin and ambient temperature and the relationship and effect on each other over time. The data requires an initial storage of reference values and has no relationship to the input for a specific individual.

Pompeii, United States Patent Publication No. 2003/0169800, for an Ambient and Perfusion Normalized Temperature Detector, published Sep. 11, 2003, discloses an infrared thermometer that estimates core body temperature by measuring the axillary and/or tympanic temperature of adults with an infrared sensor. The device calculates core body temperature using the arterial heat balance equation which is based on heat flow through thermal resistance from an arterial core temperature to a location of temperature measurement to the ambient temperature. The arterial core temperature is calculated based on ambient temperature and sensed skin temperature. Pompeii suffers from the deficiencies described above with respect to infrared thermometers, generally, including technique and lens quality. In addition, Pompeii's calculation does not use a direct measurement of ambient temperature. Ambient temperature is an important factor in determining skin surface temperature because the effects of ambient temperature on the skin can grossly affect the resulting measured skin temperature. To account for ambient temperature, Pompeii calculates the core temperature of the individual using the sensed temperature of the detector as the ambient temperature, with 80° F. being the presumed value for the detector. However, the detector may be either cooler or warmer than the surrounding ambient environment, affecting the accuracy of the result of the calculation. The accuracy of the final temperature calculation may be improved through adding or subtracting 20% of the difference between 80° F. and the actual temperature of the device.

Specifically, in other methods of axillary thermometry, the difference between skin temperature and ambient temperature is calculated as being a weighted coefficient determined by approximating h/pc where h is an empirically determined coefficient which includes a radiation view factor between the skin tissue and the ambient temperature, p is the perfusion rate and c is blood specific heat. The approximation of h/pc under normal circumstances for afebrile individuals varies over a range of at least 0.09 to 0.13 corresponding to a variation of about 30%.

Instead of assuming that the ambient temperature, estimated by Pompeii to average approximately 80° F., is always the same as the detector temperature, Pompeii weights the sensor temperature by 20% as the sensor temperature varies from 80° F. For example, if the detector is sensed to be at 80° F., the corresponding ambient temperature used in the calculation is not corrected because the detector temperature and the ambient temperature are assumed to be equal. However, as the temperature of the sensor increases or decreases from 80° F., the ambient temperature used in the calculation of body temperature is varied by 20% accordingly in the same direction.

Fraden, United States Publication No. US 2005/0043631, for a Medical Body Core Thermometer, published Feb. 24, 2005, discloses a device intended primarily for surface temperature measurements. The device calculates core temperature by sensing the temperature of the skin while accounting for the sensor temperature and ambient temperature. The device has a first sensor for measuring skin temperature as a function of the thermal resistance of the user. The device has a second sensor which measures a reference temperature of the measuring device. Although Fraden accounts for ambient temperature, the device is not adapted to measure ambient temperature which is an important factor in calculating an accurate measurement of skin surface temperature. Fraden attempts to eliminate ambient temperature from the calculation by using a pre-warming technique comprising an embedded heater to heat the device to a temperature that is near the potential skin temperature.

Fraden further utilizes an equation that requires multiple measurements of skin temperature to account for the effects of ambient temperature. The equation does not require a detected ambient temperature, nor does Fraden measure the ambient temperature. The Fraden device does require at least three temperature measurements to determine skin temperature. The first measurement is the detected temperature of the device before it is placed in contact with the skin. The second measurement is an initial skin temperature measurement detected upon the placement of the probe on the skin of the user. The third measurement is the detected temperature corresponding to an altered temperature after the device is placed in contact with the skin. This altered temperature measurement is related to the increased skin perfusion resulting from the surface pressure exerted on the skin by the device. Specifically, when surface pressure is exerted on the skin of an individual, the perfusion of the stressed skin is increased due to the vasodilatation of the blood vessels at that particular site. This results in an increased blood flow at the site and possibly a more accurate skin temperature measurement.

Based on the multiple measurements taken with the Fraden device, the skin temperature of the individual is calculated. Core body temperature is calculated using experimentally determined constants and the calculated skin temperature. Although the blood flow to the area is increased so that skin temperature can be more accurately measured, ambient temperature still has an effect on the skin temperature, and the result of the calculation is in conflict with the true core body temperature of the individual.

Matsumura, U.S. Pat. No. 5,050,612, for a Device for Computer-Assisted Monitoring of the Body, issued Sep. 24, 1991, discloses a method for estimating core body temperature at the skin surface comprising monitoring the skin surface temperature at a location on the body. Matsumura discloses that ambient temperature affects the temperature measured at the skin surface, but a first device contemplated by Matsumura uses only a skin temperature sensor and insulation to prevent the ambient temperature from affecting the skin temperature measurement. Insulation of at least a four square centimeter area is used in connection with a temperature sensing means to insulate the skin from the surrounding environment such that the skin could theoretically adjust more closely to core body temperature. Matsumura further discloses a second device that includes a second sensor for measuring the temperature of the ambient environment and in addition to lesser quantities of insulating material to insulate the skin from the ambient environment. However, the insulating material is required in a lesser quantity.

Data is detected by both the first and second sensors and used to manually calculate the core body temperature of the individual. The user creates a look-up table by charting a record of the skin temperature and corresponding ambient temperature. Matsumura states that by correlating skin temperature as it exists at a particular ambient temperature, core temperature can be determined. Matsumura does not disclose how core body temperature is determined but allows for the use of a table to correlate measured and calculated temperature. The determination of ambient temperature can also be affected by the amount of insulation used in constructing the device. For the first device, Matsumura requires a minimum of four square centimeters of insulation to be placed around the sensor to shield it from the environment. For the second device that is equipped with an ambient sensor, Matsumura is not specific but only states that that the required insulation is less than what is required for the first device. If wear of the device is not consistent in that the insulation is removed and changed during the charting of reference temperatures, the effect of the ambient temperature may not be a consistent result with respect to skin temperature. The insulation shields the skin sensor from the environment and a certain temperature is detected based upon the amount of insulation used. If the amount of insulation varies between the placement of the sensor device on the body, the accuracy of the user created chart is affected.

Ward, U.S. Pat. No. 4,509,531, issued Apr. 9, 1985 for a Personal Physiological Monitor, discloses a continuous physiological monitor that detects changes in either galvanic skin resistance, temperature or both in order to detect the onset of hypoglycemic states in a diabetic individual. A temperature reference is automatically established by the device as it is worn by the user. The skin temperature of the user is monitored by a skin temperature sensor, and once the measured temperature drops below the temperature reference, an alarm sounds. Ward mentions that ambient temperature affects the skin temperature measurements of an individual but does not provide a means to measure or a method to account for ambient temperature.

Dogre Cuevas, U.S. Pat. No. 5,938,619 for an Infant External Temperature Monitoring Transmitter Apparatus with Remotely Positionable Receiver Alarm Mechanism, issued Aug. 17, 1999, also discloses a device to detect changes in skin temperature. However, although the device comprises a skin temperature sensor, it does not provide a mechanism to measure ambient temperature. Further, Dogre Cuevas does not contemplate ambient temperature as having an effect on skin temperature.

Continuously measuring body temperature of an individual can be beneficial in monitoring the well-being of that individual and provides a better indication of the individual's normal body temperature. Having knowledge of the normal body temperature of an individual may aid in the prevention of life-threatening conditions can be prevented or detected quickly. Temperature measurement devices exist that provide both serial and continuous temperature detection and measurement of the user. However, the serial temperature measuring devices are not very helpful in monitoring the normal body temperature of an individual for quick identification of an abnormal temperature unless monitoring is done manually by the user or caregiver. Further, the current temperature measurement devices that provide continuous measurement provide less than accurate results because the devices fail to account for conditions that affect skin temperature, including activity, personal physiology and diaper conditions for both infants and adults.

Additionally, many prior art devices base the calculations of core temperature upon certain measured alternative conditions, such as skin temperature and utilize standardized conversions or tables of data to correlate these readings to a meaningful output temperature.

Therefore, what is lacking in the art is a continuous temperature measurement monitoring device that promotes long term wear and provides an accurate measurement of the actual core body temperature of an individual. Additionally, what is lacking is a multisensor device which may utilize additional environmental and physiological parameters to increase the accuracy of the temperature output. These temperature measurements may also be utilized to provide activity and conditional information about the individual which may be useful for informational, diagnostic and other purposes.

SUMMARY OF THE INVENTION

A monitoring system is provided which may comprise either a one or a multi component embodiment which includes at least a temperature module. The module may be provided with a display for output of temperature and other data as well as a variety of input capabilities. The module is particularly sized and shaped to conform to and interface with the skin of the wearer, typically in one of several preselected preferred locations. The first and most preferred location for the device is in the valley formed by the juncture of the leg and the torso which is adjacent the passage of the femoral artery close to the hip and is preferably affixed by the use of an adhesive strip. The module may also be affixed to a garment or diaper, but is preferably operated in a confined space within a diaper or clothing. All applications and embodiments described herein are equally applicable to children and adults, while infants and the elderly or infirm are the most typical candidates.

A multi component system includes a module in addition to a receiver for receiving temperature and other data measurements. The presentation of raw or derived information may include current skin and/or ambient temperature, current derived core body temperature, temperature trends for all of these current values and contextual data.

Data may be collected and processed by the module and transmitted to a receiver, or may provide all processing on board. The module may also be adapted to communicate with other devices through direct telecommunication or other wireless communication as well as over local, wide area or global computer networks.

The module may be provided with an electronic tag or other ID of some known type so that receivers may be able to detect and display discrete information for each such patient in a multiuser environment. The modules may also communicate with certain third party or other associated devices.

The system is primarily intended for home use, typically for monitoring of an infant. The system is equally applicable, however, to hospital, nursing home or other institutional use. For example, a simple adhesive patch embodiment may be utilized in an emergency room for each patient, especially those waiting to be seen for the first time, to make initial physiological assessments or to alert triage about a significant change in the condition of a waiting patient. The module may also be utilized during surgery as a less invasive and more convenient temperature or conditional measurement device, especially when other typical locations for such measurements are inaccessible or inconvenient. Post operative care, including the use of temperature dependent patient warming devices may also be based upon the output of the system.

The core embodiment of the shape and housing of the module provides a significant aspect of the functionality of the device. In general, the device has a curved, relatively thin housing which may have a variety of convex and concave portions for creating an appropriate space and interface with the skin. It is typically held in place by an adhesive pad, which may be shaped in accordance with the needs of the specific application. The adhesive material may further support or contain all or additional sensors or electrodes for detection of the various parameters.

The housing components of the module are preferably constructed from a flexible urethane or another hypoallergenic, non-irritating elastomeric material such as polyurethane, rubber or a rubber-silicone blend, by a molding process, although the housing components may also be constructed from a rigid plastic material. An ambient temperature sensor is preferably located on the upper surface of the housing facing away from the skin and a skin temperature sensor is preferably located along a protrusion from the lower housing and is placed against the skin. The housing may be provided with an orifice therethrough to facilitate the use of heat flux sensors thereon.

While the preferred embodiment is durable in nature, a number of disposable or combination embodiments are presented. In disposable applications, the entire module and mounting material are utilized for a relatively short period of time and are discarded. In a combination embodiment, certain key or costly components are placed in a durable housing which is integrated physically and electrically with additional components which are disposable. Disposable and combination embodiments are specifically directed at short term use and low cost. Certain embodiments may be specifically provided with a known, limited lifetime.

In all embodiments, a number of methodologies are described for initiating operation of the device. The device and attendant receiver may have traditional means for turning the units on or off, or may be auto-sensing, in that the devices wake up upon detecting certain use-related conditions. The devices may also be equipped with medication or other nutrients or the like for delivery by the device, upon programmed control or direction by a caregiver.

A receiver is intended to display a variety of information and may be incorporated in other devices such as a clock radio which has a primary use unrelated to the temperature measurement system. The receiver provides a locus of information relating to the changing condition of the wearer and may present an iconic, analog or digital indication as to the data being measured, any derived information based upon both measured and other data as well as certain contextual information. Also displayed may be trends of change and indications of changes meeting certain present thresholds. Alarms, warnings and messages, both on the receiver and sent through the various transmission networks may be initiated upon the meeting of such preselected or event driven thresholds.

The module includes at least one sensor, a processor and potentially an amplifier to provide appropriate signal strength of the output of the sensor to the processor. An analog to digital converter may also be utilized. The digital signal or signals representing detected temperature data and/or other relevant information of the individual user is then utilized by the processor to calculate or generate current temperature data and temperature data trends as well as derived data and contextual data. All data or relevant information may be stored in memory, which can be flash memory. A discrete clock circuit may also be provided. Sensor input channels may also be multiplexed as necessary. The processor may be programmed and/or otherwise adapted to include the utilities and algorithms necessary to create derived temperature and other related data. The receiver may output the data directly on a display or other informative means to a caregiver or may transmit the data according to a number of techniques electronically to a network or other device.

In operation, the skin temperature sensor preferably detects a skin temperature and an ambient temperature sensor preferably detects a temperature corresponding to the near ambient environment of the individual within the protective enclosure of the diaper. The module is subject to calibration to aid in the accuracy of the detection of data. The step of feature creation takes as input the temperature data or any other sensor data, which may or may not comprise calibrated signals and produces new combinations or manipulations of these signals. The system reviews and analyzes the data streams and identifies patterns and conditions, preferably through the use of multiple sensors. These detectable patterns and conditions, together with conditions and parameters which are observed immediately prior to such patterns and conditions, create repeatable and definable signals which may be utilized to warn or predict future events, behavior or conditions. This data and conclusions may be presented in graphs, reports or other output which reflect the correlations and predictions.

The device is also able to detect appropriate data to derive the proximity of other humans to the patient as mentioned above. Additional modalities for detection of proximity include those well known in the art as well as a proximity detector, as disclosed herein, which utilizes an oscillator constructed around the ambient capacitance of a metal plate. As the environment surrounding the plate changes, such as mounting the device on the human body or moving other objects closer/farther from the device, the capacitance of the plate changes, leading to a change in the frequency of the oscillator. The output of the oscillator is then input into a counter/timer of a processor. This permits the device to be aware and detect the presence of humans or other defined objects, which may be recorded and utilized as part of the analytical tools identified above.

The device may preferably be utilized for (i) monitoring of infants and children in day care or other extended non-parental supervision and (ii) the increasingly important monitoring of elderly patients under institutional or other nursing care, in order to detect or assess, among other things, abuse and neglect of the people under care.

BRIEF DESCRIPTION OF THE DRAWINGS

FIG. 4 is a cross sectional view of a of a temperature measurement module mounted on the body of an individual.

FIGS. 11A-G illustrate five aspects of a seventh embodiment of the temperature measurement module.

FIGS. 21A and 21B are diagrammatic views of a third embodiment of the circuitry of the temperature measurement module including a receiver.

DESCRIPTION OF THE PREFERRED EMBODIMENTS

Figure 1:
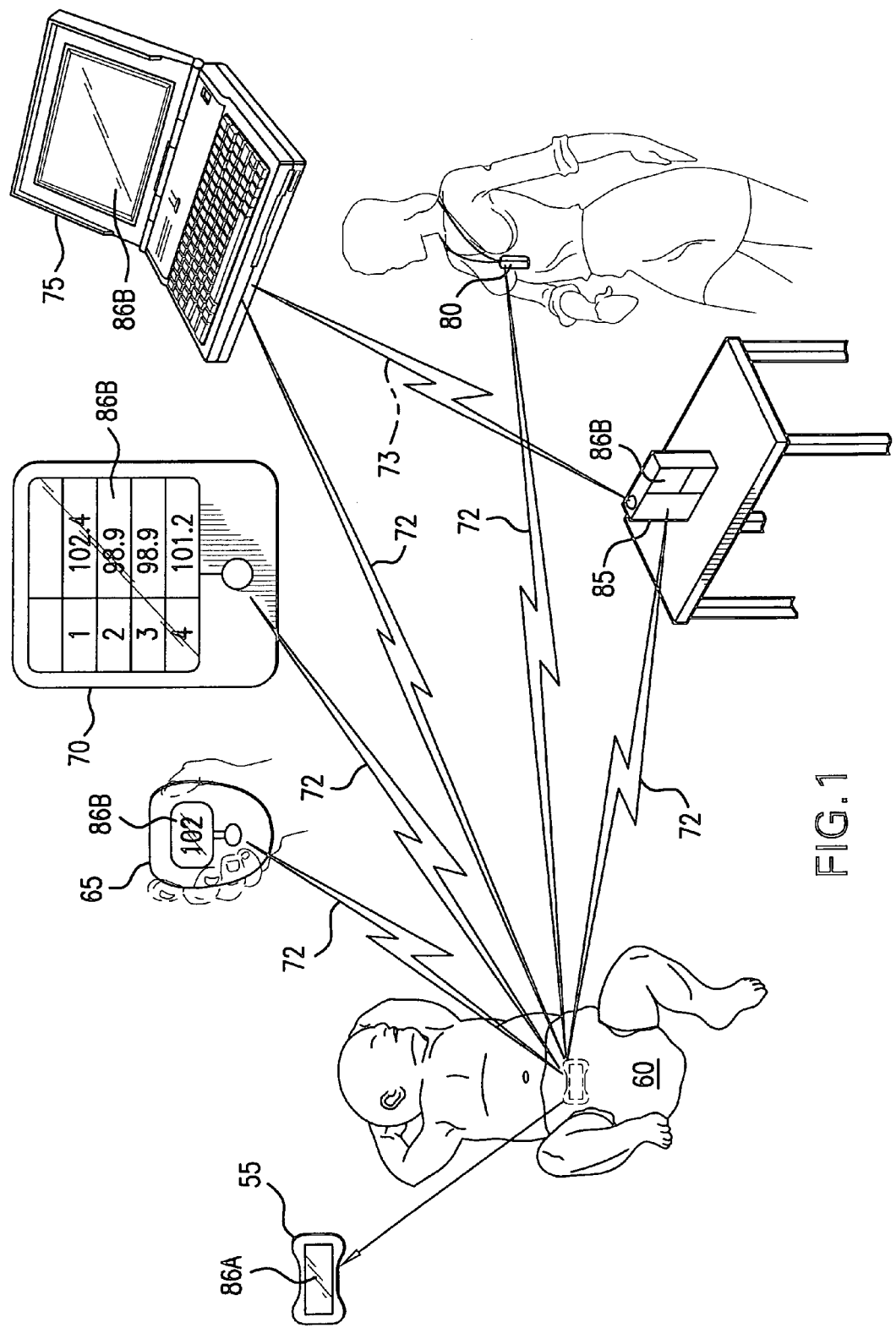
FIG. 1 is a diagrammatic representation of a system utilizing the temperature measurement module together with various embodiments of a receiver device.

With reference to FIG. 1, the monitoring system may comprise either a one or a multi component embodiment. In its simplest form, being a one component embodiment, temperature module 55 is provided with display 86A for output of temperature and other data. Module 55 may be provided, according to the knowledge of one skilled in the art, with a variety of input capabilities, including wired or wireless transmission in a manner similar to the wireless output described herein. Other modalities of input may include a button, dial or other manipulative on the device itself (not shown). This one component embodiment is placed immediately adjacent to and in contact with the body of an individual at one of many preselected locations as will be described further. It is to be specifically noted that each module may also be generally comprised of the features and components of those sensor units described in: Stivoric, et al., U.S. Pat. No. 6,527,711, issued Mar. 4, 2003, for Wearable Human Physiological Data Sensors and Reporting System Therefor; Stivoric, et al., U.S. Pat. No. 6,595,929, issued Jul. 22, 2003, for System for Monitoring Health, Wellness an Fitness having a Method and Apparatus for Improved Measurement of Heat Flow; Teller, et al., U.S. Pat. No. 6,605,038, issued Aug. 12, 2003, for System for Monitoring Health, Wellness and Fitness; Teller, et al., pending U.S. patent application Ser. No. 09/595,660, for System for Monitoring Health, Wellness and Fitness; Teller, et al., pending U.S. patent application Ser. No. 09/923,181, for System for Monitoring Health, Wellness and Fitness; Stivoric, et al., pending U.S. patent application Ser. No. 10/227,575, for Apparatus for Detecting Human Physiological and Contextual Information; Teller, et al., pending U.S. patent application Ser. No. 10/682,759, for Apparatus for Detecting, Receiving, Deriving and Displaying Human Physiological and Contextual Information; Andre, et al., pending U.S. patent application Ser. No. 10/682,293, for Method and Apparatus for Auto-Journaling of Continuous or Discrete Body States Utilizing Physiological and/or Contextual Parameters; Stivoric, et al., pending U.S. patent application Ser. No. 10/940,889, for Method and Apparatus for Measuring Heart Related Parameters and Stivoric, et al., pending U.S. patent application Ser. No. 10/940,214 for System for Monitoring and Managing Body Weight and Other Physiological Conditions Including Iterative and Personalized Planning, Intervention and Reporting, which are all incorporated herein by reference.

In the one component embodiment, all functions including data output are contained within the housing of temperature module 55. While almost any contact with the body is sufficient to enable the user to develop some indication of temperature, in the most preferred forms, temperature module 55 is placed in one of the preselected locations. This placement is applicable to both the one and multi-part component embodiments.

Referring to FIG. 1, module 55 has multiple alternative placement locations and is positioned adjacent to and in contact with the wearer's body. The first and most preferred location for the device is in the valley formed by the juncture of the leg and the torso which is adjacent the passage of the femoral artery close to the hip. This femoral region provides a location which is well sheltered from body movements which might lead to dislodgement, is close to a major blood vessel at or near core temperature and the skin surrounding the area is conducive to mounting module 55. Other mounting locations include the inguinal area, the axillary area under the arm, the upper arm, the inside of the thigh, crotch/groin area, behind the ear and ear lobe, the forehead, in conjunction with the tympanic location described above, on the sole of the foot, the palm of the hand, the fingers, the wrist, between the corner of an eye and the side of the nose, the chest and on the back in several locations along the spine. Generally, appropriate locations are those locations as where module 55 is amenable to the use of clothing or skin or both as an insulating structure and/or environmentally protecting structure, which improves the accuracy of the skin, which is well perfused in these areas. Additionally, an important consideration is the ability to obtain an appropriate ambient temperature, as will be described more fully herein, at that location. With particular reference to the back regions, especially in infants or bedridden adults, particular advantage can be taken of the insulation features of the mattress upon which the infant is sleeping to the body. This minimizes external influences and noise. Additionally, any moving, rolling over or sitting upright by the child will result in alternative readings which can be useful in determining whether the context and/or position of the child has changed, as will be more fully described herein. Lastly, other physiological parameters, such as heart beat, energy expenditure and the like can be measured at many of these locations, as more fully described in Stivoric, et al., U.S. patent application Ser. No. 10/940,889.

Although an infant is illustrated in FIG. 1, all applications and embodiments described herein are equally applicable to children and adults. Furthermore, the use of different types of garments, including diaper 60 are to be considered analogous in infants, children and adults. With respect to the femoral region location, it has been observed that infants, especially prior to full development of internal temperature regulation systems, may exhibit excellent correlation to core temperature at the skin. After development of temperature regulation in the older infant, child or adult, this location provides excellent correlation to core temperature at the skin, however, certain adaptations to measuring devices and techniques must be adopted, which will be more fully described herein, in order to ensure proper skin perfusion, insulate the skin temperature sensor from the ambient environment and potentially utilize other sensor readings to adjust the detected measurements.

It is generally considered in the art that the skin is one of the least accurate sites to measure for core temperature. It is, however, considered a useful adjunct to other standard temperature methods, especially for evaluations of how environmental, physiological and/or physical activity affects human body. Accuracy is significantly affected by perfusion characteristics of the skin and tissue immediately adjacent the measurement location. One additional location for temperature measurement is the wrist, however, it must be understood that this area is plagued by very significant and complex noise because of peripheral shutdown of the arterial and venous systems, as well as increased activity levels at this location.

It is further contemplated that a multiplicity of modules 55 may be placed on the body simultaneously to increase accuracy of detected parameters and derived output. Additionally, each one of such multiple modules may have different sensors or capabilities, with the data from each being transmitted to another module having the appropriate processing on board, or to an off-body receiver which collects and processes the data from the various modules. Moreover, some processing can be performed on some modules and not others, as necessary to transmit the data in a useful manner.

As will be discussed further herein, the temperature module 55 is preferably operated in a confined space, such as within a diaper or clothing. This confined space serves to filter ambient noises that can affect the skin temperature readings. In certain embodiments, however, module 55 may be utilized to detect certain physiological parameters, such as activity, which may be improved by the exposure of portions of the device to ambient conditions. The confined space, in the appropriate embodiments, may also be provided as part of an adhesive patch rather than under clothing or a diaper.

A multi component system includes module 55 that may be provided with display 86A, in addition to a receiver for receiving continuous temperature measurements and other relevant, statistical data including processed data that is output from module 55 for visual presentation on display 86A of module 55 or on a receiver display 86B The visual presentation of information may include current skin and/or ambient temperature, current derived core body temperature, temperature trends for all of these current values, and contextual data, Contextual data as used herein means data relating to the environment, surroundings, location and condition of the individual, including, but not limited to, air quality, audio sound quality, ambient temperature, ambient light, global positioning, humidity, altitude, barometric pressure and the like. It is specifically contemplated, however, that contextual data may also include further abstractions and derivations regarding the condition and status of the body, including the position of the body and the detection of certain events and conditions within and without the body, such as urination in a diaper, dislodgement of the module, activity and rest periods, the nature and quality of sleep and removal of the insulating clothing or diaper.

Module 55 may further be integrated into an item of clothing or a diaper, subject to the requirements, as more fully described herein, that sufficient pressure is exerted on the module in order to achieve proper interface with the skin.

Figure 19:
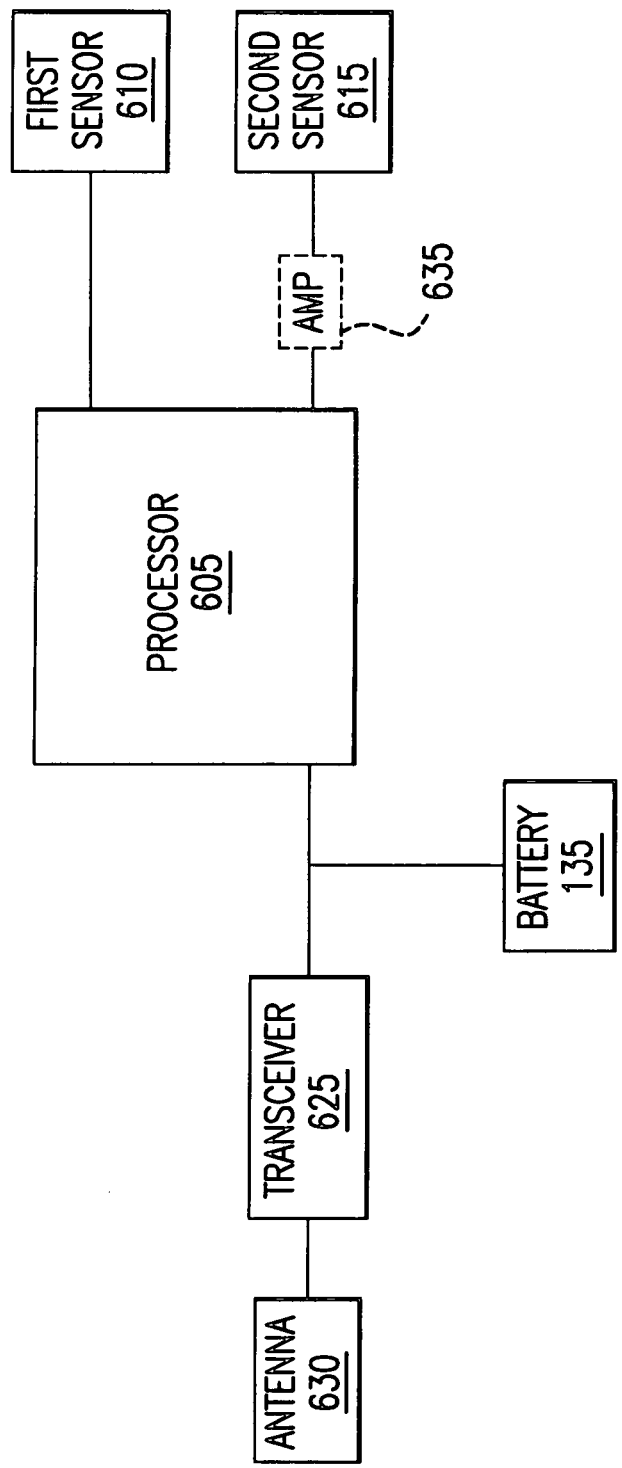
FIG. 19 is a diagrammatic view of a first embodiment of the circuitry of the temperature measurement module.
Figure 20:
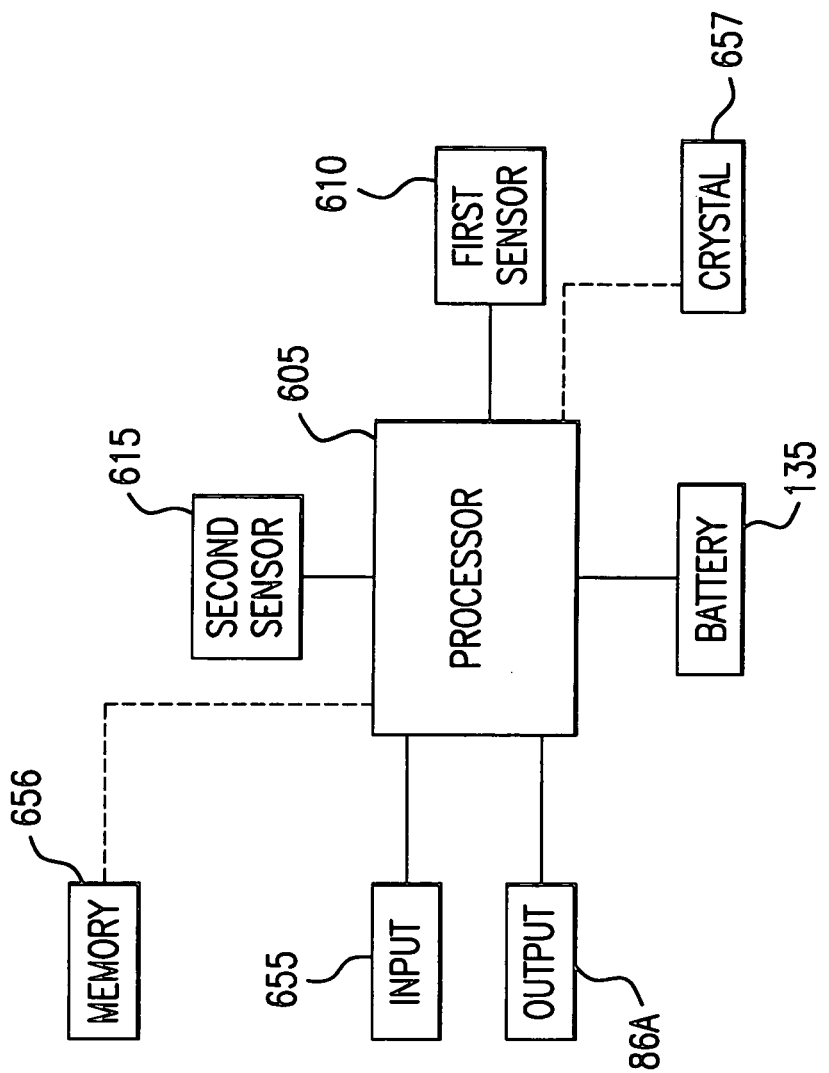
FIG. 20 is a diagrammatic view of a second embodiment of the circuitry of the temperature measurement module.

Data may be collected and processed by module 55 and transmitted by primary transmission 72 to a receiver through a short-range wireless transmission, such as infrared, RF transmission or any other known wireless transmission system as known to those skilled in the art and as further described herein with respect to FIGS. 19-21. The receiver can take one of a number of forms, including a table top receiver 85, a hand held receiver 65, clinical monitor receiver 70, a personal computer 75 or a necklace receiver 80, a ring, a headworn display, a headsup display, a display built into the dashboard or windshield of a car, displayed directly on the clothing of the person being monitored or on the caregiver's clothing, displayed on household appliances such as a refrigerator, a microwave oven or conventional oven, be reflected qualitatively in controllable ambient conditions such as the temperature of a room, the lighting of the room, or the sound in a room, a watch or an armband as disclosed in Stivoric, et al., copending U.S. patent application Ser. No. 09/923,181 and can be remotely positionable with respect to module 55. The receiver may further comprise a microphone, as would be apparent to one skilled in the art, for detecting environmental sounds. The distance between module 55 and receiver is dependant upon the type of transmission used. The module may also be provided with a wide area wireless chip or other CDMA equivalent for direct telecommunication with other devices or through a network. The module may also transmit its data to such a chip in a cell phone or other device that includes wide area wireless functionality, which may then forward the information anywhere in the world. Alternatively, module 55 may communicate with a receiver or a group of receivers that combines the features of any one of the receiver forms. If more than one receiver unit is utilized in a multi-component system, the data is relayed across the network of transceiving components or transmitted to each receiver in the system as described more fully with respect to FIGS. 19-21.

It is further contemplated that intermediate receivers may be utilized to both expand the range of the system as well as provide another locus for processing capability. In this embodiment, a primary transmission 72 would be provided between a receiver 85 and module 55, and a secondary transmission 73 would be provided between the receiver 85 and an additional receiver, such as personal computer 75. Additionally, in a multisensor, multipatient environment, module 55 may be provided with an electronic tag or ID of some known type so that receivers may be able to detect and display discrete information for each such patient. The modules may also communicate with certain third party or other associated devices which may be associated with the wearer or even implanted thereon, such as a false tooth or therein to uniquely identify that wearer by electronic or biofingerprinting means. Additional receivers and multiple levels of transmission are contemplated in such an environment with appropriate encoding or transmission identification to prevent overlap or confusion of signals. It is also possible to adapt a mass triage system such as that described in Stivoric, et al., copending U.S. patent application Ser. No. 10/940,889 which would also allow communication to occur across modules near each other as a self-healing network which is also location-awareness capable.

Table top receiver 85 is provided with a housing that contains electrical circuitry for communicating with module 55 and receiving the relevant data, as described further herein with respect to FIGS. 19-21. Table top receiver 85 may be battery-operated; self powered through heat flux, magnetic flux, solar power, motion flux or ambient RF harvesting or it may operate through a power supply by inserting an attached plug into an electrical outlet. Receiver may be in the form of a hand-held receiver 65 which is also preferably constructed of a rigid plastic, although the housing may also be constructed from any durable, disposable, or biodegradable material that can protect the components of hand-held receiver 65 from destruction and/or the necessary times of use. Clinical monitor receiver 70 operates in a likewise manner as the other receivers and is utilized in a medical setting. Necklace receiver 80 is constructed of a lightweight material conducive to being worn on the body or may be in the form of a key fob, a ring, a bracelet, or the like.

Clinical monitor receiver 70 and personal computer 75 receive continuous raw and derived temperature measurements and other related data, including processed data such as current temperature, temperature trends and contextual data from module 55. Clinical monitor receiver 70 and personal computer 75 may further include a processor to process continuous temperature and other related data and calculate current temperature, temperature trends and contextual data. Clinical monitor receiver 70 may contain additional features so that it can be electrically connected to third-party medical monitoring equipment which is used to monitor other patient conditions. These receivers may be used for additional purposes, which may, in fact, be the primary purpose for which the device is designed.

Any of the receivers is adapted to receive continuous temperature measurements and other related data, including processed data such as current temperature, temperature trends, patterns recognized, derived states and contextual data from module 55, as will be more fully described herein. Each receiver is adapted to display relevant data on display 86B according to the process described with references to FIGS. 19-21 herein.

Module 55 may also be provided with the ability to obtain data, either through a wired or wireless connection, from other types of physiological detection equipment, such as a glucometer or ECG device, incorporate that data into its detected parameters and/or process and/or transmit the combined and collected data to the receiver. The device can also be provided with anti-tamper mechanisms or features to prevent or at least identify whether it has been opened or manipulated. This is also applicable to any covering or adhesive material utilized to mount the module to the body. The module could also be provided with medication which could be administered subcutaneously or topically upon the receipt of the necessary instructions.

Figure 2A:
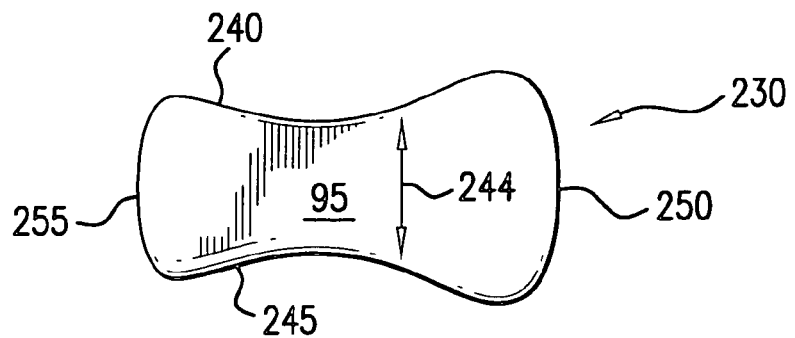
FIG. 2A is a top plan view of a core leaf spring embodiment of a temperature measurement module.

FIG. 2A illustrates a core embodiment of the shape and housing of module 55, which provides a significant aspect of the functionality of the device. The figures are intended to illustrate the central surface features of the primary embodiments, regardless of overall geometry and are generally applicable thereto. A leaf spring module 230 is preferably constructed of a flexible or springy material having a durometer between 80A and 90A, however the module performs equally well as a rigid device. FIGS. 2A through 2D are intended to illustrate the gross physical features of the device. Leaf spring module 230 has upper housing 95, a first long side 240, a second long side 245, a first short side 250 and a second short side 255 with the first and second long sides 240, 245 having a curved shape. It is to be noted that second short side 255 may be smaller in section than first short side 250, as illustrated in FIGS. 2A through 2D to facilitate mounting in certain areas of the body, including the femoral region. The module is generally concave on upper housing 95 in the longitudinal central section 243 along the longitudinal axis extending from short sides 250, 255 and may be flat, convex or a combination thereof, as well as along transverse central section 244 extending from long sides 240, 245. It is further provided with longitudinally convex features 246 at the distal ends of upper housing 95. These features 246 may be flat, convex or concave or a combination thereof in the transverse direction.

Additionally, the first long side 240 and second long side 245 are preferably chamfered or radiused, as would be selected by one skilled in the art, along the edges that form the boundaries connecting a side surface 260 of leaf spring module 230 to lower housing 100 and along the boundaries connecting side surface 260 of leaf spring module 230 to upper housing 95. The chamfered edges of first and second long side 240, 245 allow the skin to form around leaf spring module 230 as it is pressed against the body, rocking along with the body's motions, while maintaining sensor contact. This chamfered surface is further illustrated with respect to FIG. 6C. The chamfered surface may be flat, convex, or slightly concave or some combination through its cross section and along the length of the chamfer.

Lower housing 100 is generally convex in both longitudinal central section 243 and transverse central section 244. However, the convexity of transverse central section 244 may alternatively be formed by three relatively flat longitudinal regions 247, 248, 249, separated by ridges. Central longitudinal region 248 may not necessarily extend entirely between short sides 250, 255 but may be confined to a central region.

Figure 2B:
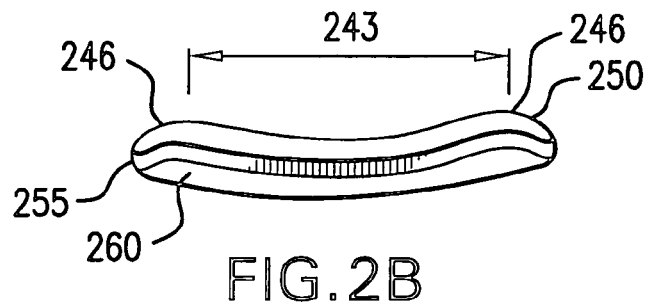
FIG. 2B is a side elevational view of a core leaf spring embodiment of a temperature measurement module.
Figure 2C:
FIG. 2C is an end elevational view of a core leaf spring embodiment of a temperature measurement module.

As shown in FIGS. 2A-2D, the shape of leaf spring module 230 is generally curved so that lower housing 100 is in contact with the body of the wearer. The curvature of leaf spring module 230, as illustrated in FIG. 2B, causes lower housing 100 to exert pressure on the skin surface of the wearer which results in increased contact of wearer's body with lower housing 100 in addition to increased perfusion of the skin. This interaction creates a snug and relatively insulated interface between the skin and module, especially in the central longitudinal region 248 within longitudinal central section 243, which increases, or at least leaves undisturbed, the perfusion of the skin beneath the module with fresh blood which is relatively close to core temperature. This interface is further facilitated by the folding of adjacent skin along the sides of the module which may also overlap the module to the level of upper housing 95 and cradle the module therein. The locations selected and identified herein for placement of the module are generally concave to accept the convex form of the module, or are pliant enough to be molded into the appropriate shape to accept the module and create the necessary interface. With respect to the folds of skin coming in contact with the surface or edge, the radiused or chamfered edges are designed to not impinge on comfort and the convex curves and chamfers are specifically intended to push into the cavities available at the location, especially with limbs and body folds, taking into consideration not just the skin surface, but also the muscles adjacent and underneath these regions which allow for these placements and ease the acceptance location and pressure of the module comfortably at the location.

The generally curved shape of leaf spring module 230 and chamfered edges of first and second long side 240, 245 accept, allow, and guide the folds of the skin, fat, and muscle to comfortably and unobtrusively fold over onto the upper housing 95 of leaf spring module 230. In infants especially, the skin fold of the femoral region is convex when the infant's body is fully extended, however, in its natural state, or fetal position, the legs are folded toward the torso. This creates a mostly concave space for accepting the module and module 55 is adapted for insertion in this area because of the shape of the leaf spring module 230. In addition, the surface of upper housing 95 facing away from the body is preferably concave, but it can be flat or convex in cross section, to accept the folds of skin in the femoral region of the body, axillary or other local. The size and dimension of leaf spring module 230 does not affect the fit of leaf spring module 230 in the femoral region. Further, the corners of leaf spring module 230, and optionally all edges or intersections of surfaces, may also be radiused for comfort and wearability of the user so that the leaf spring module 230 does not irritate the body unnecessarily.

Figure 2D:
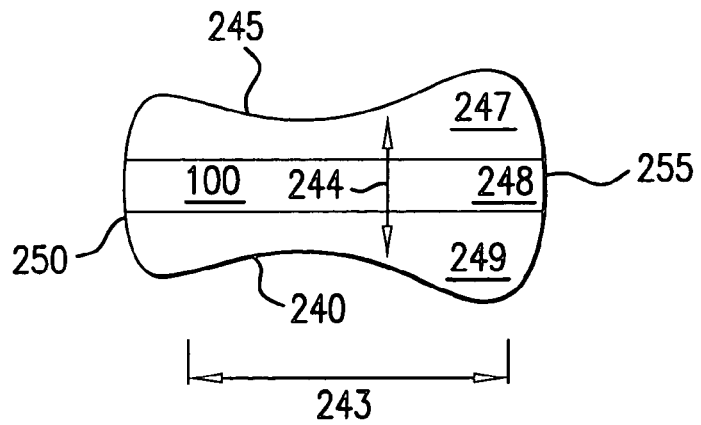
FIG. 2D is a bottom plan view of a core leaf spring embodiment of a temperature measurement module.

The material from which leaf spring module 230 is constructed can absorb the shocks of the motions of wearer while maintaining pressure of the skin temperature sensor area of lower housing 100, illustrated in FIG. 2D, against the desired contact location. This absorbent quality can additionally be aided by the use of a stretchable springy adhesive to adhere the module to the body, as will be more fully described herein, especially if the module itself is rigid. The material from which leaf spring module 230 is constructed should further have a slight bending quality yet with sufficient memory which enables the leaf spring module 230 to retain its shape over long-term continuous use. Because appropriate interface contact of the relevant areas of lower housing 100 of leaf spring module 230 with the skin surface of the wearer is maintained, the results are not substantially affected by wearer motions including bending over, lifting of the leg, and contraction or extension of the stomach and abdomen muscles. In addition, the generally curved body shape of leaf spring module 230 causes it to push into the skin and conform to the body's natural shape allowing it to roll with the body and further have a spring action as it moves with the motions and folds of the body of the wearer.

Leaf spring module 230 is attached to the body by an integrated or separate adhesive material, the shape and configuration of which will be more fully described herein. While the application of the appropriate adhesive material will be highly case dependent and within the ambit of one skilled in the art, a non-exhaustive list of such materials includes: hydrophilic material which will allow skin to breathe and transfer of water or sweat from skin surface; semi permeable films, polyurethane foams, hydrogels; Microfoam, manufactured by 3M Corporation and Tegaderm, also manufactured by 3M. These adhesives could also be layered with a heat-sensitive gel having a lower critical solution temperature where under the influence of the user's body or skin temperature, the intermediate layer actively produces a constant modification of contact points to either enhance or limit or selectively limit thermal conductivity and or comfort between the module or adhesive strip and the skin. The adhesive may further be provided on the module itself.

The attachment to the module may also be a non adhesive interface such as a collar or flexible restraint around the perimeter by stretching over it or popping over a lip, as more fully described in Stivoric, et al., copending U.S. patent application Ser. No. 10/227,575. The adhesive may also be variable in its adhesive qualities and not monolithic across its surface, different on the module as opposed to the skin interface, and even variable at these different surfaces. A non-woven adhesive, with appropriate breathable materials that provide the stretch and spring to further enable the concept of the leaf spring module's sensor contact with the body and response to human movements and skin folds, muscle interactivity, and any combination of the above is most preferred. Adhesive material is in contact with a portion of leaf spring module 230 on first short side 250 and extends to skin of wearer.

The adhesive pad may be shaped in accordance with the needs of the specific application, however, a non-exhaustive list of examples would include the use of a simple adhesive strip which covered the module either longitudinally or transversely, wings of adhesive material which extend outwardly from the module itself which may be removable/replaceable and multiple adhesive sections which hold the ends of the module or have multiple connected sections or snaps which fasten the module to the skin according to various geometries. The adhesive material may further support or contain additional sensors, electrodes for use in an ECG detector or piezoelectric strain gauges for the additional sensing capabilities. The module being restrained by the adhesive also exhibits to certain detectable movement, which may act as a shuttle in an accelerometer. This displacement may then provide basic information regarding activity and motion similar to an accelerometer.

Leaf spring module 230 can also be held in place on the body by pressure received from a waist band or a similar pressure causing object. For example, besides adhering to skin, the adhesive could adhere to itself, loop back and adhere to itself and/or loop back and connect to itself with a reseatable/removable fastener. Leaf spring module 230 may be snapped into or otherwise held in place in a garment, a waistband or other like restraint. The module may also be restrained in a tightly fitting garment which is particularly designed to exert sufficient pressure on the module to create the skin interface. The garment may have specific body tension areas which are designed for such function, or elastic or other materials arranged as appropriate. The module can be integrated into the garment, and simply placed, snapped or pocketed behind these tension areas, without module required adhesive.

Figure 3:
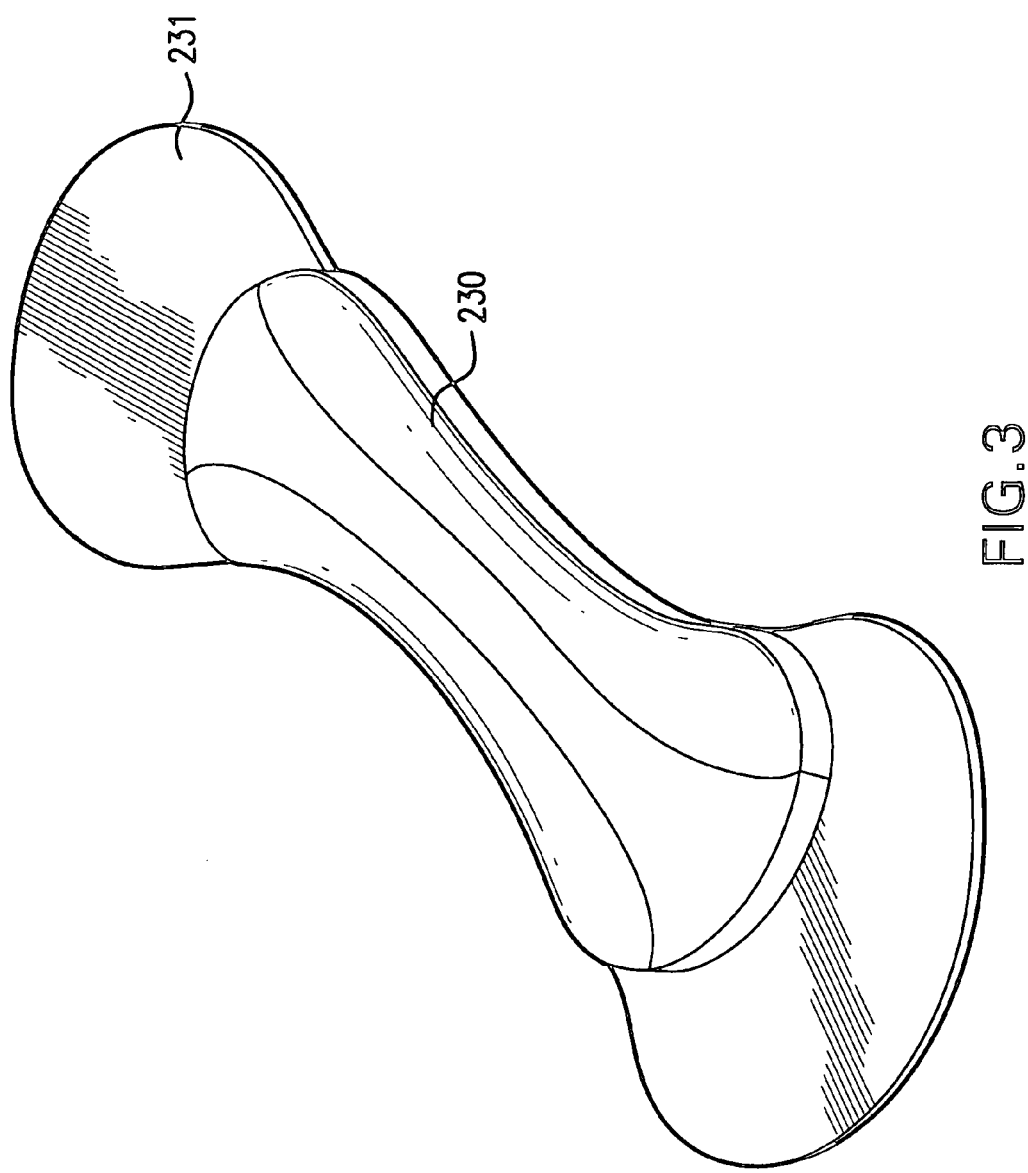
FIG. 3 is an alternative embodiment of the core leaf spring embodiment of a temperature measurement module.

Referring to FIG. 3, leaf spring module 230 may also be detachable or provided with integrated flexible wings 231 that create downward pressure or increased stability on the skin when pressed on or adhered to the body to create a compound spring form that moves and bounces with the body motions while maintaining contact with the skin of the wearer. The pressure contact with the skin reduces signal noise resulting from body motion and can reduce temperature warm up times.

The dimensions of the leaf spring module 230 are variable depending on the age of the wearer. Some tested and preferred, but not limiting, dimensions for a larger leaf spring module 230 are 1.325 inches long×2.5 inches wide×0.25 inches deep. The dimensions for a smaller size leaf spring module 230 further vary based on the age and size of the wearer, and may be 1.5×0.6125×0.25 inches, respectively. The size of leaf spring module 230 can vary considerably from these dimensions based on the specific embedded components or additional constraints such as the need to conform to safety regulations as provided in the United States Consumer Product Safety Commission, Office of Compliance, Small Parts Regulations, Toys and Products Intended for Use By Children Under 3 Years Old, 16 C.F.R. Part 1501 and 1500.50-53.

FIG. 4 illustrates a cross section of module 55 mounted on the body of the wearer. Module 55 has an ambient temperature sensor 120 located along upper housing 95 of module 55 and a skin temperature sensor 125 located along lower housing 100 of module 55. Module 55 optionally has foam insulation in contact with and covering a portion of module 55. Foam insulation may be incorporated as outer mounting foam and includes an upper foam support. Upper foam support 305 is in contact with and extends along one end of upper housing 95 of module 55. Additional upper foam support 305 is in contact with and extends along the opposite end of upper housing 95 of module 55.

Foam insulation, in order to increase the thermal footprint of the device and therefore increasing and/or maintaining skin perfusion levels, may also be incorporated as lower foam support 307. Lower foam support 307 is in contact with and extends along one end of lower housing 100 of module 55. Additional lower foam support 307 is also in contact with and extends along the opposite end of lower housing 100 of module 55. Foam insulation can be placed at any one of these locations or in a combination of these locations.

Module 55 is secured by adhesive strips that may be placed at a number of locations further illustrated in FIG. 4, including an upper adhesive 300 and a lower adhesive 298. Upper adhesive 300 extends across module 55 on one end of upper housing 95 and is in contact with and covering upper foam support 305. Upper adhesive 300 may extend beyond upper foam support 305 and be in direct contact with upper housing 95 of module 55.

Lower adhesive 298 extends across module 55 on one end of lower housing 100 and is in contact with and covering lower foam support 307. Lower adhesive 298 is further in contact with the skin in a manner that adheres module 55 adjacent to skin 310 for temperature measurement. Lower adhesive 298 may be double-sided adhesive strips (add this to wing concept) having one side adhered to lower foam support 307 and a second side adjacent to and in contact with the skin of wearer. Adhesive strips 298 and 300 can be shaped for a particular part of the body on which module 55 is located. The adhesive strips are also flexible so that module 55 adheres to the body of the wearer body while the body is in motion.

Figure 5A:
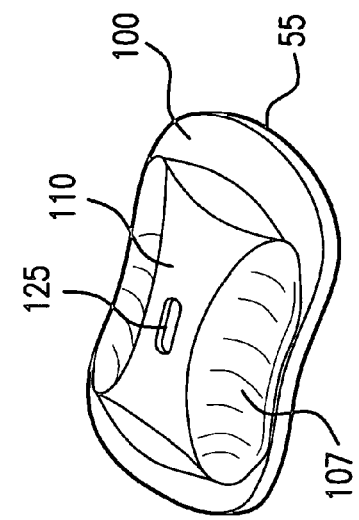
FIG. 5A is an isometric view of the top surface of a preferred embodiment of a temperature measurement module.
Figure 5B:
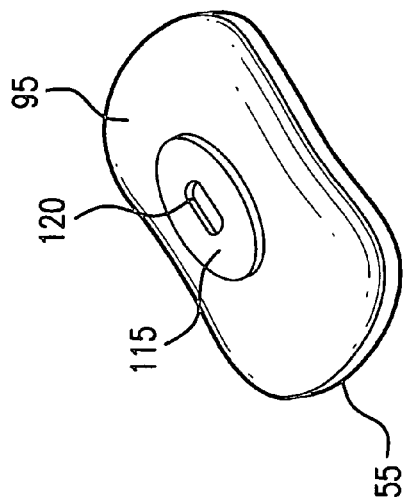
FIG. 5B is an isometric view of the bottom of a preferred embodiment of a temperature measurement module.
Figure 5C:
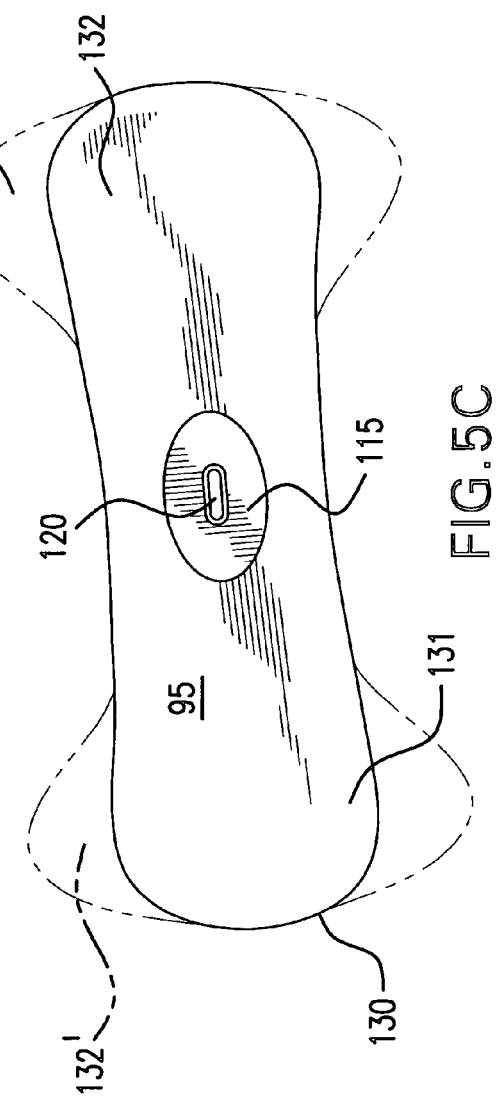
FIG. 5C is a top plan view of a second embodiment of a temperature measurement module.

FIGS. 5A through 5C illustrate the general construction of a module 55 constructed generally in accordance with the description of leaf spring module 230, accounting for construction and manufacturing considerations and needs. The housing components of module 55 are preferably constructed from a flexible urethane or another hypoallergenic, non-irritating elastomeric material such as polyurethane, rubber or a rubber-silicone blend, by a molding process, although the housing components may also be constructed from a rigid plastic material. Ambient temperature sensor 120 is located on upper housing 95 and is protected by a sensor cover 115. Ambient temperature sensor 120 can be large enough such that the entire surface of upper housing 95 can be the active sensor area, or the active sensor can be located only on a portion of upper housing 95, preferably at the apex of upper housing 95 furthest from the wearer's body, and skin in order to provide the largest thermal variance and/or insulation from the skin temp sensor. It is to be specifically noted, however, that to the extent that module 55 is located within a diaper or article of clothing, ambient temperature sensor 120 is not detecting ambient temperature of the room or even the environment near the body. It is detecting the ambient temperature of the area enclosed within the article of clothing or the diaper. Ambient temperature sensors for detection of the actual room temperature or the area surrounding the area of exposed parts of the body are provided by other ambient sensors, as will be described more fully with respect to multi-module embodiments or the receiver unit. This enclosed ambient temperature which is actually sensed by ambient temperature sensor 120 in most uses and embodiments is particularly useful in both derivation of the core temperature as well as the context of the user or any events occurring to the user, as will be described herein with respect to the operation of the system.

As illustrated in FIG. 5B, module 55 further comprises a lower housing 100 opposite upper housing 95. Skin temperature sensor 125 is located along protrusion 110 which corresponds to central longitudinal region 248 of leaf spring module 230. Lower housing 100 of module 55 is placed adjacent to and in contact with the skin of the wearer. Relieved sections 107 adjacent protrusion 110 correspond to lateral longitudinal regions 247, 249 of leaf spring module 230 and enhance the interface of protrusion 110 with the skin. The surface of lower housing 100 is preferred to be smooth for cleaning requirements especially for multi-use products, but the surface may be textured, either finely or coarsely, to increase the connection to the wearer's skin irrespective of dead skin cells and hair or to increase contact surface area, pushing around the hair, and upon application and or continued skin movement slight abrading the skin of its dead cells to make a cleaner connection. These surfaces can also be enhanced by the use of microneedles to gather data that is not as insulated by the cutaneous skin surface, where the microneedles are probing an active, fluid, subcutaneous/epidermal layer of skin. Especially in less durable applications, such as disposable patches, as described more fully herein, that are meant for limited use time periods, these microneedles or other textures could be quite advantageous, where the thermal conduction to the sensor is extended to these forms in order to be less affected by the insulated qualities of stratum corneum, extending into the epidermal layer, not long enough to extend into the blood or nerve ending/pain receptors and into an interstitial layer that will potentially/inherently conduct body temperatures to the sensor better than the surface of the skin. The convex surface of module 55, and specifically protrusion 110 of lower housing 100, enables module 55 to push into the skin and maintain contact with the skin during the various body and/or limb positions, activities, conditions or bodily motions and allows module 55 to conform to bodily motion. Conversely, the surface features guide the skin thickness and folds and underlying muscles to conform around or along the form of the module, maintaining a high degree of actual and perceptual comfort to the wearer, but also maintaining a high degree of contact with the skin of the body, as well as aiding in the insulation of the sensor from the ambient environment and temperature.

FIG. 5C illustrates a second embodiment of module 55 which is an elongated module 130. As previously described with respect to FIGS. 5A and 5B, the housing components of module 130 are preferably constructed from a flexible urethane or an elastomeric material such as rubber or a rubber-silicone blend by a molding process, although the housing components may also be constructed from a rigid plastic material. Ambient temperature sensor 120 is located along a central portion of upper housing 95 of elongated module 130 and can be protected by sensor cover 115 if necessary, as described with respect to FIG. 5A. Elongated module 130 further has a first wing portion 131 and a second wing portion 132. Wing portions 131, 132 are located opposite to each other on either side of sensor cover 115 and can be of equal or varying lengths and widths depending on location of body being attached to requirements for adhesion and force against the body. Elongated module 130 may be adapted to conform to the size of an individual other than an infant in that the dimensions of the first wing portion 131 and the second wing portion 132 can be varied. Depending on certain characteristics of the wearer, such as age, weight or body size, in addition to the proposed location of the modules on the body, first and second wing portion 131, 132 may be made larger or smaller depending on the fit required for the comfort level associated with continuous wear. Alternative wings 132' are shown in chain line to illustrate a variation on this embodiment. This embodiment may further comprise an entirely flexible and adhesive exterior surface.

Figure 6:
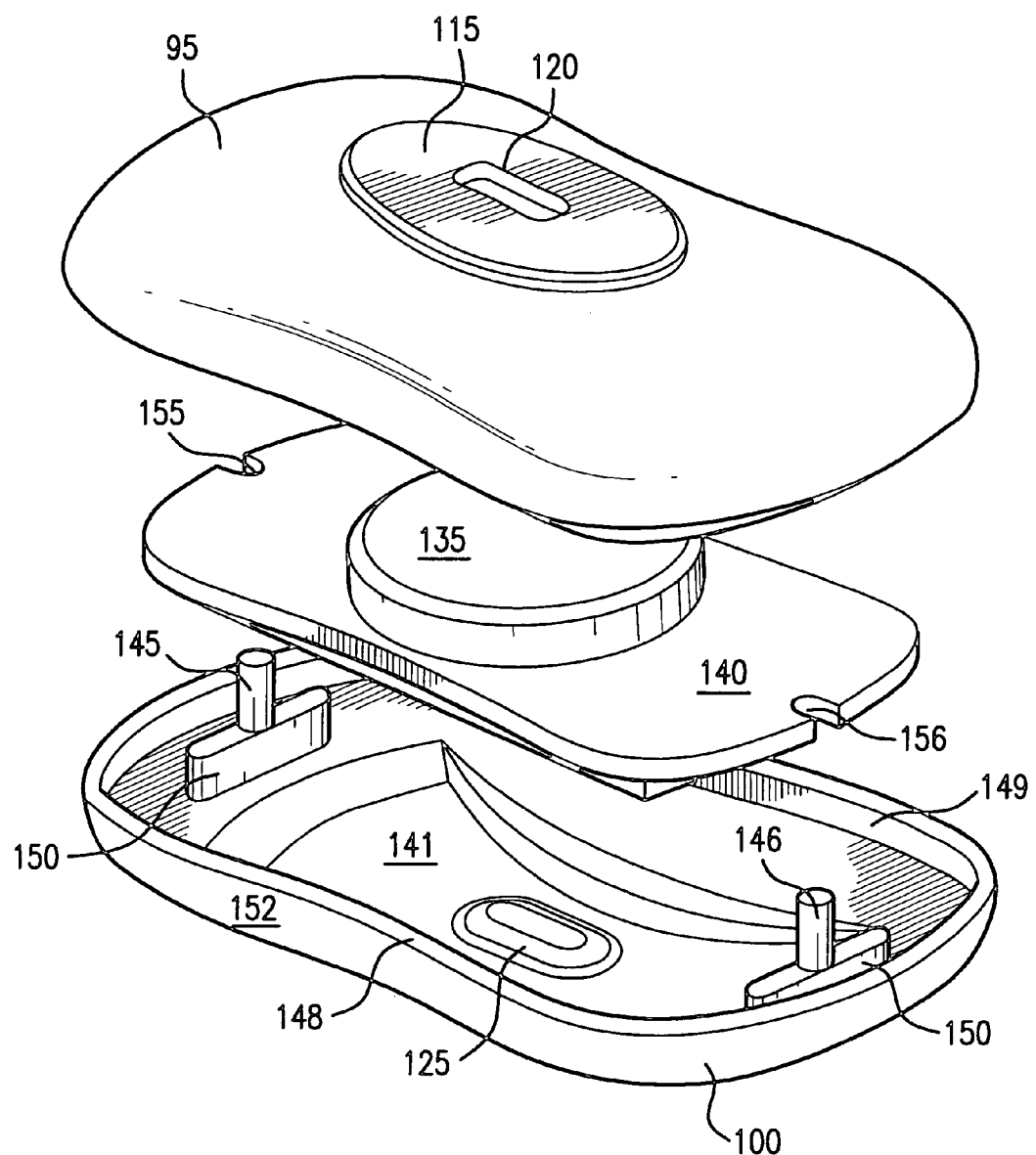
FIG. 6 is an exploded view of the preferred embodiment of the temperature measurement module.

Referring now to FIG. 6, ambient temperature sensor 120 is located along a portion of upper housing 95 and is directed away from the body of the wearer. Ambient temperature sensor 120 is protected by sensor cover 115. Module 55 contains a central portion comprising printed circuit board 140 adapted for insertion within the upper and lower housings 95, 100, which contains circuitry and components generally in accordance with the electronic configurations described herein. Printed circuit board 140 has a power source in the form of a battery 135, which may be either permanently mounted or replaceable. Battery 135 can be any one of a coin cell, a paper battery, plastic film battery, capacitor, RFID component, solar or other similar device, as would be apparent to those skilled in the art. Battery 135 and the components of printed circuit board 140 are electrically connected in a conventional manner to each other and sensors 120, 125 as would be apparent to one skilled in the art (not shown). Printed circuit board 140 further has a first alignment notch 155 on one end of printed circuit board 140 centrally located along one edge of printed circuit board 140. Printed circuit board 140 further has a second alignment notch 156 on one end of printed circuit board 140 centrally located along an opposing edge of printed circuit board 140.

Module 55 further comprises a generally oblong shaped lower housing 100 having a recess 141 on its inner surface opposite and corresponding to outer surface protrusion 110 of lower housing 100, as described with respect to FIG. 3B. Lower housing 100 further comprises a lip 148, extending generally perpendicular from the surface of module and having an interior wall portion 149 and an exterior wall portion 152. Skin temperature sensor 125 is located along recess 141 of lower housing 100 inner surface. Lower housing 100 has alignment pins 145, 146 which are supported by alignment pin supporting bosses 150, 151.

Upper housing 95 may also benefit from a form that keeps the skin folds from actually touching the ambient sensor in order to maintain the quality of its data, because touching the ambient sensor may compromise the measurements and accuracy of the output. Alignment pins 145, 146 extend in a perpendicular orientation away from lower housing 100 to extend through the alignment notches 155, 156 of printed circuit board 140. By extending through the first and second alignment notches 155, 156 of printed circuit board 140, printed circuit board 140 is secured to lower housing 100 and is prevented from moving laterally with respect to first and second alignment pins 145, 146. The housing may also be sonically welded together with the circuit board being molded, insert molded, potted or embedded within the housing or other manufacturing techniques within the ambit of those skilled in the art may be applied.

Figure 7A:
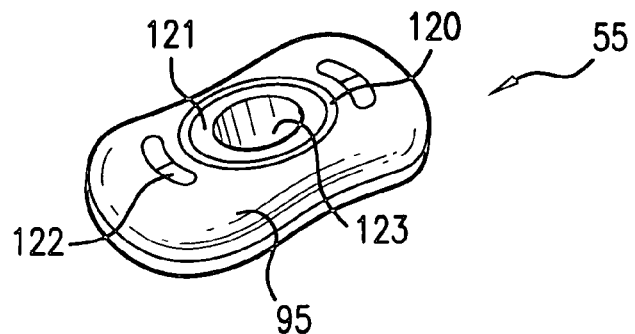
FIG. 7A is an isometric view of the top of a exploded bottom view of a third embodiment of the temperature measurement module.

Referring now to FIG. 7A, a third embodiment of module 55 is presented, also generally in accordance with the geometric housing features of leaf spring module 230. Upper housing 95 and lower housing 100 are symmetrical in this embodiment and are generally constructed as previously described with respect to FIGS. 5 and 6. This embodiment further comprises a heat flux sensor, generally in accordance with the teachings of Stivoric, et al., U.S. Pat. No. 6,595,929. The heat flux sensor comprises heat conduit 121 and is operated in conjunction with orifice 123 which extends annularly through the central portion of both upper and lower housings 95, 100, providing a conduit for ambient air throughout orifice 123. Heat conduit 121 surrounds the annular orifice 123 and extends entirely between the respective surfaces of upper and lower housings 95, 100. Immediately adjacent the annular ends of heat conduit 121 and circumferentially surrounding at least a portion of heat conduit 121 on upper housing 95 is ring-shaped ambient temperature sensor 120.

Figure 7B:
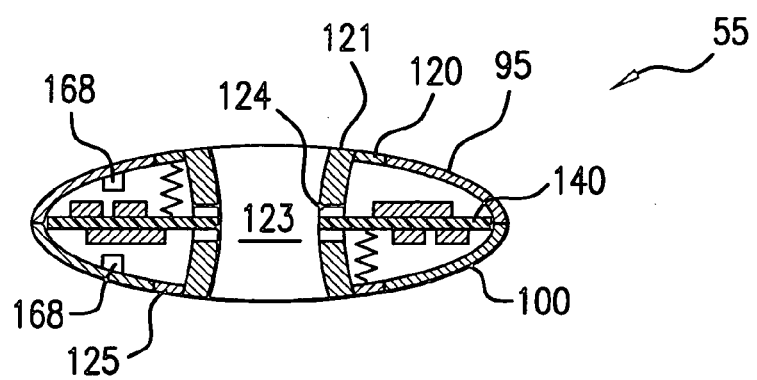
FIG. 7B is a sectional view of the third embodiment of the temperature measurement module.
Figure 7C:
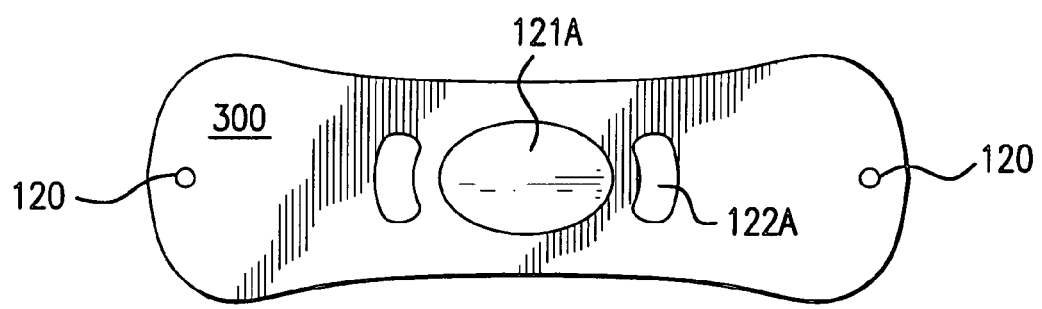
FIG. 7C is a top plan view of an adhesive strip for mounting the third embodiment of the temperature measurement module to the body.

Referring now to FIG. 7B, printed circuit board 140 is interposed within the space created by housing 95, 100 and may be thermally isolated from heat conduit 121 by thermal interface 124. Skin temperature sensor 125, analogous to ambient temperature sensor 120 is ring-shaped and circumferentially surrounds the opening of annular heat conduit 121 at lower housing 100. This embodiment may also incorporate the use of alternative or additional external sensors or power sources which may be mounted on or integrally with adhesive 300, as would be known to those skilled in the art and as illustrated in FIG. 7C, which shows an exemplary placement of additional ambient or skin temperature sensors 120. Microphone or other acoustic sensor 168 may optionally be placed on either the skin or ambient side of the housing to detect motion and sounds such as crying, snoring, heartbeats, eating, drinking and other environmental noises. In the event that electrical communication is necessary between components located on or in adhesive 300, electrical contacts 122, 122A are provided on upper housing 95 and adhesive 300, respectively. Adhesive 300 is further provided with orifice 121A corresponding to orifice 121 of module 55 to permit the passage of ambient air. Adhesive 300 is placed on upper housing 95 and the skin of the user consistent with the illustration of FIG. 4.

It is to be specifically noted that a number of other types and categories of sensors may be utilized alone or in conjunction with those given above, including but not limited to relative and global positioning sensors for determination of location of the user; torque and rotational acceleration for determination of orientation in space; blood chemistry sensors; interstitial fluid chemistry sensors; bio-impedance sensors; and several contextual sensors, such as pollen, humidity, ozone, acoustic, body and ambient noise, including these sensors, combinations of these sensors, and any additional sensors adapted to utilize the device in a biofingerprinting scheme, where the wearer can be identified by their physiological signatures, as well as how their body provides these sensors with certain values and/or patterns during certain body states and or activities. This is important when a multiplicity of sensors on multiple individuals is contemplated in a confined space, such as a hospital. It is important to distinguish one wearer from a different wearer, even if just for the sake of distinguishing between two people. For example, in a family, where when one person wears the unit, the unit will automatically understand who the wearer is, so that there is no need to include demographic or other information before incorporating the data from the product for applications or correlations where this proper personalization and/or accuracy is necessary. This same type of biofingerprinting could extend to different locations of the same user's body, so that even if not distinguishable across different people, the unit could be able to distinguish the location in which is it is being worn. The detection of this location will be more apparent with respect to the description of the processing of data provided herein.

Figure 8:
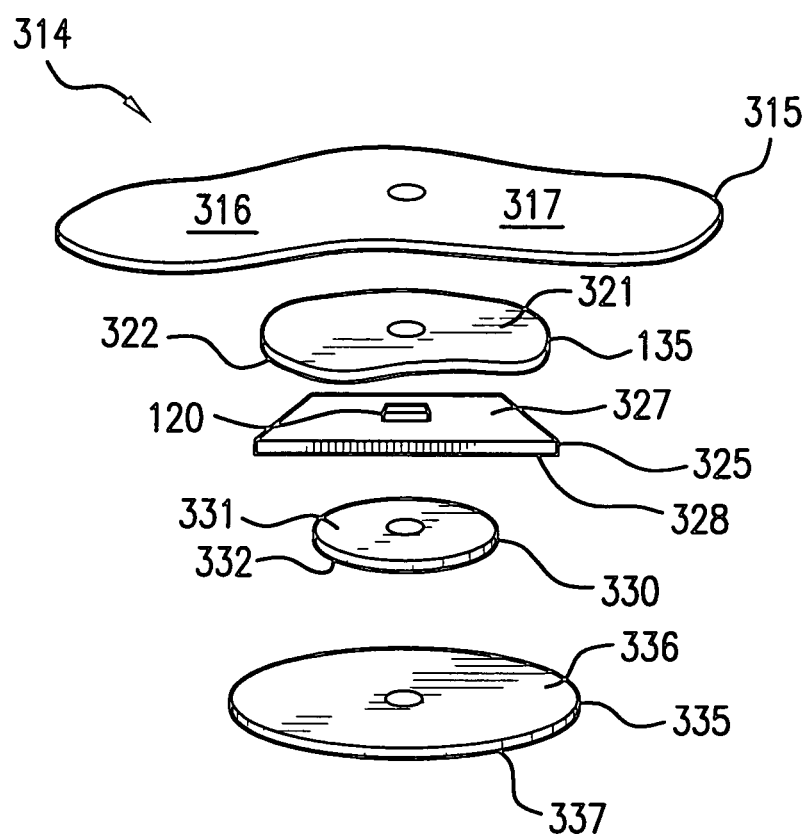
FIG. 8 is an exploded view of a fourth embodiment of the temperature measurement module.

FIG. 8 illustrates a fourth embodiment of module 55 which is a disposable embodiment comprising patch module 314. It is specifically contemplated that, as a flexible member, the patch may be of any general form or shape necessary to adhere comfortably to the body at the necessary location while providing accurate data. Moreover, the patch embodiments may include certain aspects of the more durable embodiments described herein or may also include a combination of durable and disposable components, as will be more fully described herein. In general, the disposable embodiments conform less to the geometries of leaf spring module 230 than the durable embodiments. Disposable patch module 314 comprises an adhesive patch cover 315 for adhering disposable patch module 314 to the skin of wearer. Adhesive patch cover 315 has a first wing portion 316 and a second wing portion 317 and is adapted to have an aperture in the central portion of adhesive patch cover 315. Disposable patch module 314 further comprises a battery 135, which may be a paper battery, of the type manufactured by Power Paper, Ltd., being generally oblong in shape. Battery 135 is composed of zinc anode and manganese dioxide cathode layers printed directly onto paper, plastic or other flexible material which produces electrical energy much like ordinary alkaline batteries. Another alternative is a plastic film battery or one of a type manufactured by Cymbet Corporation. Battery 135 has two electrodes separated by an electrolyte, and when the electrodes are connected, the circuit is complete and power flows through disposable patch module 314. Battery 135 is thin and flexible but is not necessarily replaceable, but may be rechargeable. Some variants are replaceable, but not the spirit of the disposable concept. This embodiment may also be provided as a self-contained unitary patch which is completely disposable.

Battery 135 has an upper side 321 that is adjacent to and in contact with adhesive patch cover 315. Battery 135 further has an aperture located in and extending through its central portion that is in alignment with aperture in adhesive patch cover 315 when battery 135 and adhesive patch cover 315 are in contact with each other. Battery 135 of disposable patch module 314 further comprises a lower side 322 opposite upper side 321 that is adjacent to and in contact with a printed circuit board 325 which supports ambient sensor 120 and skin temperature sensor (not shown). Printed circuit board 325 has a first side 327 facing away from skin on which ambient temperature sensor 120 is located. This circuit board could also be flexible. Ambient temperature sensor 120 is located in a central location on first side 327 of printed circuit board 325 and extends through aperture in both paper battery 320 and adhesive patch cover 315. Skin temperature sensor is oriented toward the skin of wearer and is located on a lower side 328 of printed circuit board 325 opposite the upper side 327 of printed circuit board 325. Disposable patch module 314 further comprises a compression material 330 for pressing the sensor against skin as with other embodiments presented, which may also be constructed of multiple densities of material in order to keep the skin sensor in proper contact, having a upper side 331 adjacent to and in contact with lower side 328 of printed circuit board 325, generally round in shape and having an aperture in the central portion that is in alignment with skin temperature sensor (not shown) that is located on lower side 328 of printed circuit board 325 generally correlating to orifice 123 as shown in FIGS. 7A-C. Compression material has a lower side 332 adjacent to and in contact with a skin interface 335. Skin interface 335 is generally round in shape and has an upper side 336 that is adjacent to and in contact with lower side 332 of compression material. Skin interface 335 further has a lower side 337 that lies adjacent and in contact with the skin when disposable patch module 314 is placed on the body of wearer. Skin interface 335 further has an aperture in its central portion through which skin temperature sensor (not shown) extends through and is in contact with the skin of wearer.

Additional considerations relating to the use of batteries include a variety of alternatives. The same battery may be removed from a device and reused, especially if the battery is a durable coin or button cell and the unit is disposable. The module may be specifically designed to accept the insertion of the battery, or even retain the battery through an undercut or an opening along the edge, the use of the adhesive or pressure from the skin itself.

One significant consideration with respect to disposable embodiments is time of wear and condition. A deteriorated device may provide inaccurate data without other indication of failure. Certain sensors, such as a piezoelectric strain detector may be utilized, as well as a mere electrochemical visual indicator to alert the user that a present time or performance limit has been reached and that the unit should be replaced. Other example displays include thermal-chemical, chemical; light-chemical and bio-chemical. The displays or detectors can be integrated into a portion or the entirety of the adhesive, in which the adhesive can be printed with different imagery. As the body moves, the collective movements could result in disruption of the material or cracking of the surface of the adhesive so that what is presented is also a mechanical, non-electronic sensor that exposes the activity of the wearer in addition to the temperature readings. This is applicable for determining the end of life of the product, as a basic activity or motion detector as well as a tampering detector, as described above.

A second consideration is power utilization. Although battery based embodiments are described and generally preferred, it is specifically contemplated that the unit may be powered by an external source, such as RF transmissions which contain sufficient power to enable the device to operate for a short period of time sufficient to take readings and transmit data. These embodiments are today not yet appropriate for continuous and/or long term measurement applications.

As with any inexpensive, disposable product, reduction of components and complexity is necessary for utility. This may include the use of conductive inks on the battery or integrated into the adhesive for electrical contacts. Additionally, elimination of switches and other controls are desired. An additional reason for elimination of on/off switches in favor of automatic startup is if the parent or caregiver forgets to turn on the device. On a durable or semi-durable module, the skin temperature sensor may be utilized as a power up detector, so that when the unit is affixed to the body, it turns on, eliminating an off/on switch and also improving power savings when the unit is not in use. The module may be configured to go to sleep for periods of time or take readings more occasionally to save the battery. The length of these periods may be set by the user, the caregiver or may be dynamically set, based upon the readings observed. For example, an elevated temperature may cause the device to take readings more frequently. Other methodologies of automatically sensing a condition to initiate operation of the device include sensing certain conditions as well as detecting certain environmental changes. For example, galvanic skin response sensors and/or heat flux sensors could be utilized to detect when the device is placed on the body. When the device is at ambient temperature and not on the body, the ambient and skin temperature sensors will report the same temperature. Once the device has been placed on the body, the temperature readings will diverge, which can be detected by the unit and utilized as a signal to begin operation. A motion detector may also signal mounting on the body. Other methodologies include the use of proximity detection or contact between the device and the receiver, for example, or the placement of the adhesive on the device. Inserting the battery may also initiate operation. Lastly, a signal could be generated from the receiver to wake up the device.

In conjunction with durable embodiments, disposable embodiments or combinations thereof, and as previously discussed, multiple units could be disposed on the body to create an array of sensors. Additionally, the array could be disposed on a single unit, using outboard sensors positioned on the adhesive or a wing. Lastly, the sensors could be completely physically separate, yet communicate with the single unit.

As previously discussed, certain embodiments may also be utilized for the delivery of medication, nutriceuticals, vitamins, herbs, minerals or other similar materials. The adhesive or the module itself may be adapted to topically apply medications in a manner similar to a transdermal patch. This functionality may also be implemented through the use of coated microneedles. Alternative on-demand delivery systems such as the E-Trans transdermal drug delivery system manufactured by Alza Corporation may also be included, with the capability of applying the medication at a specific time or when certain preset criteria are met as determined by the detection and processing of the device. For example, the temperature module could be coupled with an adhesive that delivers pain reliever to help with fever reduction. The drug delivery could be controlled or dosed or timed according to the reactions/measurements and derivations from the body. The set point for this closed loop may be factory set, or set on the device by the user or caregiver. The system may not employ a closed loop but the caregiver, through the receiver, may issue commands for some skin delivery to occur. Other examples include administering limited duration medications such as a four hour cough medicine while sleeping at the appropriate time. As stated more fully herein, the device is further capable of determining certain aspects of sleep recognition. In such embodiments, sleeping aids may be administered to help people sleep or, as they get restless in the middle of the night, be provided with an appropriate dosage of a sleep aid. Moreover, the ability to detect pain prior to full waking may allow the administration of a pain reliever. In these cases, remedial measures may be taken prior to waking, upon the detection of physiological and/or contextual signals recognized by the system as precursors of a waking event. This permits the user to enjoy a more restful and undisturbed sleep period. Additionally, the person could be awoken after 8 hours of actual biological sleep rather than by arbitrary time deadlines. The device may also be utilized for the prevention and/or treatment of snoring or sleep apnea through biofeedback.

An alternative embodiment utilizes the capabilities of the system to recognize and categorize certain pre-urination or bowel movement conditions, parameters and/or contexts. This may be useful in addressing bed wetting and bathroom training in both children and adults. For example, if the device is worn for some period of time during which these events occur, the system builds a knowledge base regarding the measured and derived parameters immediately prior to the events. These parameters may then serve as signals for an impending event and may trigger an alarm or other warning. This will allow a parent or caregiver the opportunity to reinforce proper bathroom habits or to awaken a sleeping child or unaware adult to go to the bathroom.

The adhesive could be a bioactive dressing that when placed on a burn area or suture, for example, while monitoring blood flow essential for tissue regeneration, may also be enabled with stimulating materials/minerals/substances to aid in the healing process. This provides a protective cover for the wound, encouraging healing, with a device capable of evaluating whether the process is actually occurring and successful. The device may also provide very modest electrostimulation for tissue or muscle regeneration.

The adhesive may also be designed to react to chemicals presence in normal moisture and/or perspiration from the skin, exposing results to observers through chemical reactions that result in color or other visual feedback as to the parameters sensed. These may include: sodium, chloride, potassium and body minerals. Potential conditions could be recognized such as: cystic fibrosis or substance use. The adhesive, which may be exposed to the diaper or adhered to inside of diaper or extended to a region of the body where urine will be contacted upon an insult, may be provided with certain chemical detectors for: pH, specific gravity, protein, glucose, ketones, nitrite, leukocyte, urobilinogen, blood, bilirubin, ascorbic acid, vitamin C and other like minerals and compounds. If the adhesive is further provided with microneedles, probing into interstitial fluid through various chemical, electrical or electrochemical technologies may collect and/or present data regarding: proteins, various nutrients, glucose, histamines, body minerals, pH, sodium, pO2, pCO2, body fluid status including hydration, with additional condition feedback about glucose and substance use. These adhesives could also include electrodes, potentially integrated with specific gels to allow technologies for non-invasive detection of trends and tracking of glucose levels utilizing weak electronic current to draw tiny volumes of tissue fluid through the skin for analysis of the fluid for glucose levels. Electrodes may be provided for ECG, galvanic skin response, EMG, bio-impedance and EOG, for example.

Figure 9:
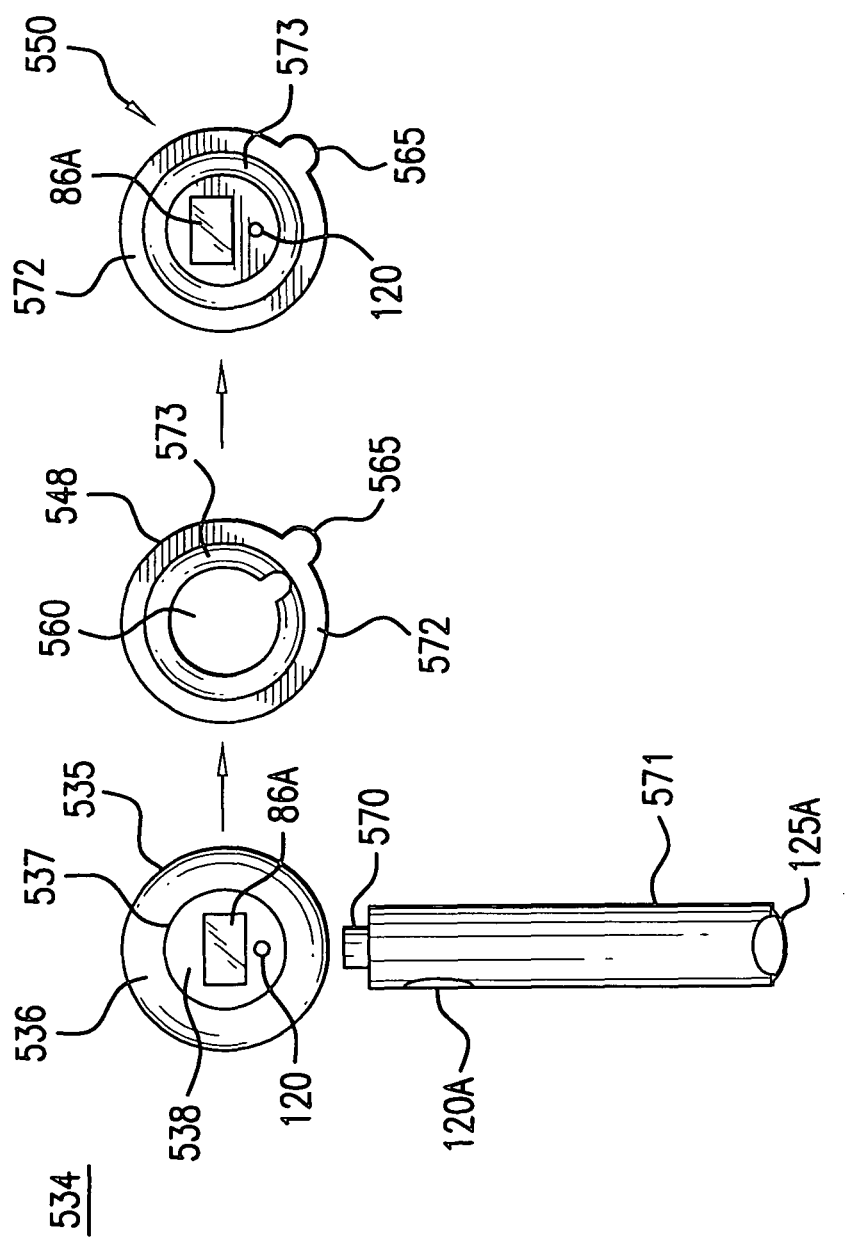
FIG. 9 is a top plan view of three aspects of a fifth embodiment of the temperature measurement module with a detachable handle.

A fifth embodiment of module 55 of the present invention is a disc temperature module 534 as illustrated in FIG. 9. Disc temperature module 534 comprises a disc 535 having a round base 536 and a round protuberance 537 extending from round base 536. Round protuberance 537 has a diameter smaller than the diameter of round base 536. The round protuberance 537 of disc 535 has a face 538 which further comprises display 86A. Optional display 86A visually presents continuous detected temperature measurements and other relevant, statistical data including processed data such as current temperature, temperature trends, and contextual data can be shown. Ambient sensor 120 is located on face 538 and skin temperature sensor (not shown) is located on the underside of disc 535 and is adjacent to and in contact with the skin of wearer. Ambient temperature sensor 120 may cover substantially all of face 538 of disc 535. Adhesive material may be placed on the under or skin side of module 534. Additionally an adhesive and/or insulating ring may be utilized in order to maintain the module on the body as will be described further herein.

Disc temperature module 534 may further comprise a detachable handle 570 having a handle projection 571 extended from one end of detachable handle 570. Detachable handle 570 may be connected to round base 536 of disc 535 by inserting handle projection 571 into an opening located on round base 536 to take a preliminary temperature measurement. In this embodiment, handle 570 is affixed to module 534 and the module is merely placed, not adhered to the designated location, such as under the arm of the patient. A static or preliminary reading is made and the handle is detached. The module 534 may then be affixed to the body or utilized in a static manner at a later time. Handle 570 may also comprise a skin temperature sensor 125A and/or an ambient temperature sensor 120A. The handle skin temperature sensor 125A may be utilized in conjunction with the module as a traditional oral or axillary thermometer to take static readings. Additionally, periodic confirmations of the operation of the device may be made by reattaching the module to the handle after some period of on-body use and taking an oral, rectal or other temperature to allow the device to check its calibration, as will be described more fully herein. In the instance where the module is removed for such a calibration, a new warm up period may be required. An alternative to eliminate such additional warm up periods is to provide a similar handle, reader or thermometer in electronic communication with the module that has a thermometer integrated therein for temperature measurement which will update the module without removal.

An alternative embodiment may include the integration of handle 570 and face 538 with display 86A, with a detachable sensor unit comprising disc 535 and the adhesive material. In this embodiment, the integrated handle 57 and face 538 comprise a receiver unit, as more fully described herein, with the detachable disc comprising the module to be affixed to the skin. In this embodiment, ambient temperature sensor 120A may also be utilized to detect the ambient temperature of the room, if the handle/receiver is within the same environment. These embodiments, in their most rudimentary forms, may merely measure relative temperature change rather than actual temperature. In this embodiment, a baseline temperature reading would be made with another device. In most embodiments of this type, the module would be preset to alarm or trigger a warning or other event upon meeting a preset criteria. An example of the utility of such a device is within a hazmat suit or firefighter's fire resistant clothing to detect when heat and lack of ventilation may cause body temperatures to rise to dangerous levels.

Disc temperature module 534 further comprises a round adhesive backing 545 having a flat surface 572 that adjoins a raised area 573 having a round shape with a diameter less than total diameter of the round adhesive backing 545. Raised area 573 has an opening 560 in a central portion that is defined by the perimeter of raised area 573. Flat surface 572 further comprises a pull tab 565 extending from flat surface 572.

Disc 535 can be engaged with adhesive backing 545 by inserting disc 535 into recess 560 of adhesive backing 545 so that the raised area 573 of adhesive backing 545 is in contact with round protuberance 537 of disc 535 forming an adhesive disc assembly 550. The adhesive disc assembly 550 is placed at an appropriate location on the body of wearer. When the wearer chooses to remove the disc temperature module 534 from the body, pull tab 565 is lifted to aid in the removal of the adhesive disc assembly 550 from the body of wearer.

Figure 10:
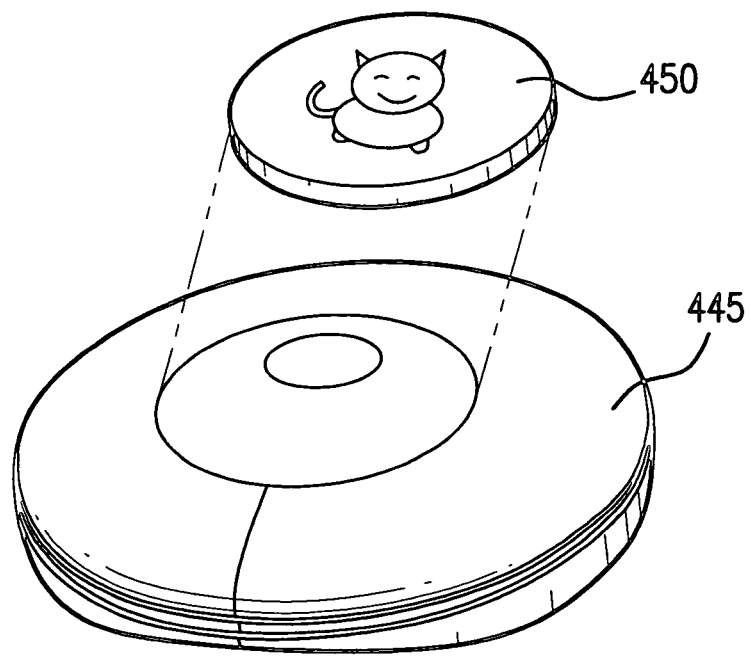
FIG. 10 is an isometric view of a sixth embodiment of the temperature measurement module.

FIG. 10 represents a sixth embodiment of module 55 in the form of a self-contained module 445. Self-contained module 445 is constructed of a durable material, preferably flexible urethane or an elastomeric material such as rubber or a rubber-silicone blend by a molding process. Alternatively, self-contained module 445 may also be constructed from a rigid plastic material. Self-contained module 445 has a display for transmitting information including, but not limited to, electrochemical display 450. Electrochemical display 450 contains an electrochromic dye that changes color when a voltage is applied across the dye. After the voltage is removed from the dye, the resulting color remains. Self-contained module 445 can be programmed such that when a predetermined threshold is reached, the electrochemical display 450 changes to reveal an image. The electrochemical display 450 may further have a removable adhesive-backed object on top of the electrochemical display 450 containing electrochemical dye such that the adhesive changes color or image when the threshold is reached. The adhesive-backed object is then removed from the electrochemical display 450 for placement elsewhere other than on the body or on self-contained module 445. This electrochemical display may furthermore be adapted for specific user types, feedback thresholds or user goals and provided for each particular application, such as 6 month old infants, firefighter or surgical suit.

FIGS. 11A through 11G illustrate a seventh embodiment of the present invention in the form of a folded clip module 495. FIG. 11A illustrates a folded clip module 495 having a first portion 510 and a second portion 515. FIGS. 11B and 11C illustrate one embodiment of folded clip module 495. In FIG. 11B, folded clip module 495 has a first portion 510 which is constructed from a durable material, preferably of flexible urethane or an elastomeric material such as rubber or a rubber-silicone blend by a molding process. Alternatively, first portion may be a rigid plastic. First portion 510 further has a circular face 520 on which display 86A is located. Display 86A visually presents continuous detected temperature measurements and other relevant, statistical data including processed data such as current temperature, temperature trends, and contextual data can be shown.

First portion 510 of folded clip module 495 has a narrow extension piece 521 that connects face 520 of first portion 510 to second portion 515 of folded clip module 495. The second portion 515 of folded clip module 495 is constructed from a malleable material, preferably of flexible circuit board or urethane or an elastomeric material such as rubber or a rubber-silicone blend by a molding process. As illustrated in FIG. 11C, folded clip module 495 is bent at the location at which extension piece 521 adjoins second portion 515 of folded clip module 495 for attachment to diaper 60 of wearer.

Another embodiment of folded clip module 495 is illustrated in FIGS. 11D and 11E. In FIG. 11D, folded clip module 495 has a first portion 510 which is constructed from a durable material, preferably of flexible urethane or an elastomeric material such as rubber or a rubber-silicone blend by a molding process. Alternatively, the first portion may be a rigid plastic. First portion 510 further has a circular face 520 on which display 86A is located. Display 86A visually presents continuous detected temperature measurements and other relevant, statistical data including processed data such as current temperature, temperature trends, and contextual data can be shown.

First portion 510 of folded clip module 495 has a narrow extension piece 521 that connects face 520 of first portion 510 to a hinge 525. Hinge 525 is used to connect first portion 510 of folded clip module 495 to second portion 515 of folded clip module. The second portion 515 of folded clip module 495 is constructed from a malleable material, preferably of flexible urethane or an elastomeric material such as rubber or a rubber-silicone blend by a molding process. As illustrated in FIG. 11E, folded clip module 495 is bent at the location hinge 525 for attachment to diaper of wearer. This embodiment may also be utilized in conjunction with adhesives for further ensuring good contact with the body, or for affixation to the garment or diaper. With respect to the skin mounted adhesives, the adhesive materials and mounting are consistent with the descriptions provided with respect to FIGS. 4-8.

In both embodiments of folded clip module 495, ambient temperature sensor (not shown) is located along the first portion 510 of folded clip module 495 and skin temperature sensor (not shown) is located along the second portion 515 of folded clip module. The ambient and skin temperature sensors, however, may be located solely on the second portion, which may, in turn, be disposable, with or without the flexible section.

FIGS. 11F and 11G illustrate the mounting locations of folded clip module 495 on diaper 60 of wearer. In FIG. 11F, folded clip module can be mounted to diaper 60 at first mounting location 505 located on the leg band of diaper 60. The first portion 510 of folded clip module 495 is placed exterior to diaper 60 and the second portion 515 of folded clip module 495 is placed under diaper 60. FIG. 11G illustrates folded clip module 495 mounted to diaper 60 at a second mounting location 505 located on the waist band of diaper. As described in FIG. 11F, the first portion 510 of folded clip module 495 is placed exterior to diaper 60 and the second portion 515 of folded clip module 495 is placed under diaper 60. This mounting technique may also be utilized in conjunction with other garments and for adult use. Furthermore, the housings utilized in conjunction with this embodiment may be detachable from the folding sections in a manner consistent with both the embodiments of FIGS. 7-9 in that certain functions and/or power sources may be located in disposable sections, with a durable housing which is reused. The power may, alternatively, be located in the diaper or garment upon which the module is mounted or supported.

Figure 12:
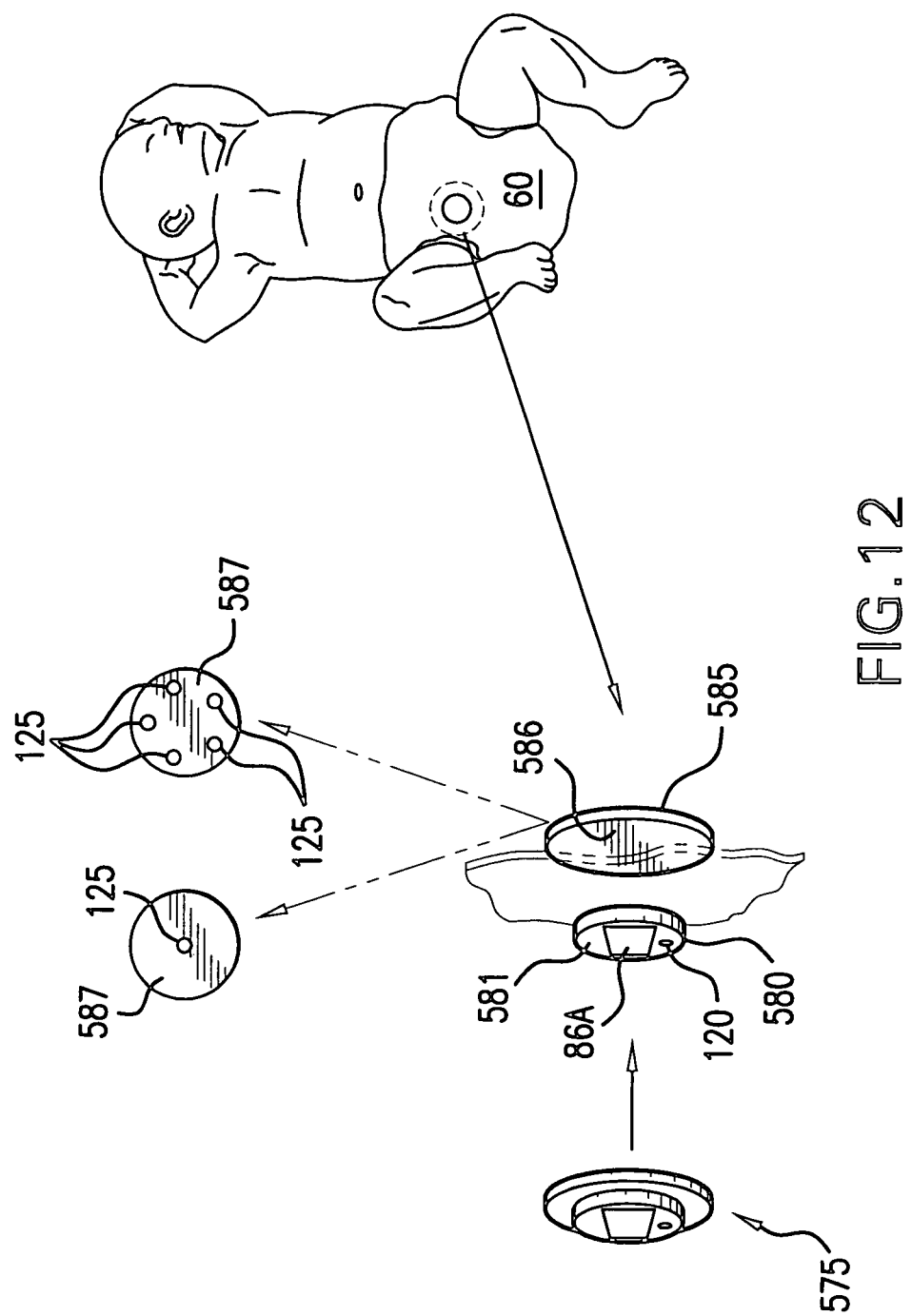
FIG. 12 is an eighth embodiment of the temperature measurement module.

FIG. 12 represents an eighth embodiment of a temperature monitor module which is a stack monitor module 575. Stack monitor module 575 comprises a first portion 580, which is a flat disc having a circular shape having a first side 581 and a second side (not shown). The first side 581 of first portion 580 has an ambient temperature sensor 120 which faces toward the environment of the wearer. First side 581 of first portion 580 also has a display 86A. Display 86A visually presents continuous detected temperature measurements and other relevant, statistical data including processed data such as current temperature, temperature trends, and contextual data can be shown. Electrical connections are consistent with those described with reference to FIGS. 7 and 8. The second portion 585 of stack monitor module 575 has a first side 586 and a second side 587. The first side 586 of second portion 585 is placed in contact with diaper 60. Skin temperature sensor 125 is located on second side 587 of second portion 585 of stack monitor module 575 and is placed adjacent to and in contact with the skin to detect skin temperature of the wearer. The second side 587 of second portion 585 may also have a single sensor or a multi-sensor array of skin temperature sensors 125. Second side (not shown) of first portion 580 and first side 586 of second portion 585 are placed in contact with diaper 60 and engaged through a piercing connection. The diaper or garment may already have an appropriately labeled and located hole, pocket, undercut or the like for receiving and/or locating the device.

Figure 13:
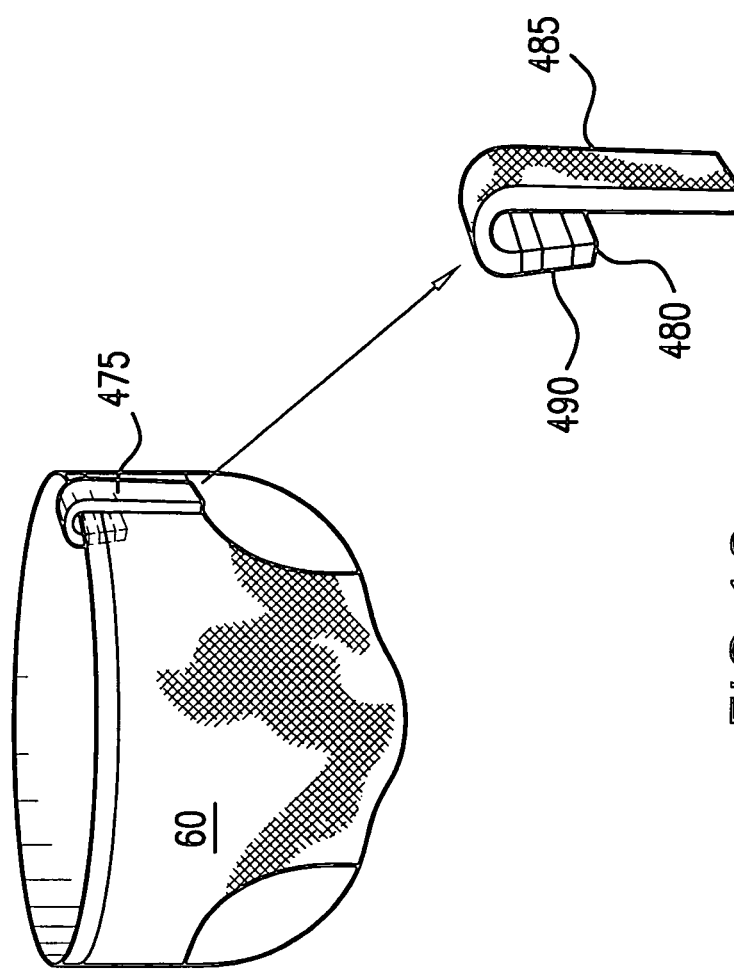
FIG. 13 is a ninth embodiment of the temperature measurement module.

FIG. 13 illustrates a ninth embodiment of the present invention in the form of a clip module 475. Clip module 475 is constructed of a malleable, flexible material such that clip module 475 can maintain its shape while attached to diaper 60. Clip module 475 is preferably flexible urethane or an elastomeric material such as rubber or a rubber-silicone blend by a molding process. Clip module 475 has an interior clip portion 480 on which skin temperature sensor 490 is located. Clip module 475 further has an exterior clip portion 485 on which ambient temperature sensor is located. Ambient temperature sensor (not shown) can be large enough such that the entire surface of exterior clip portion 485 can be the active sensor area, or the active sensor can be located only on a portion of exterior clip portion 485. Similarly, skin temperature sensor 490 can be large enough such that the entire surface of interior clip portion 480 can be the active sensor area, or the active sensor can be located only on a portion of interior clip portion 480. The interior clip portion 480 of clip module 475 is placed under the waistband of diaper 60. Clip module 475 is bent such that exterior clip portion 485 that rests on top of diaper 60.

Figure 14:
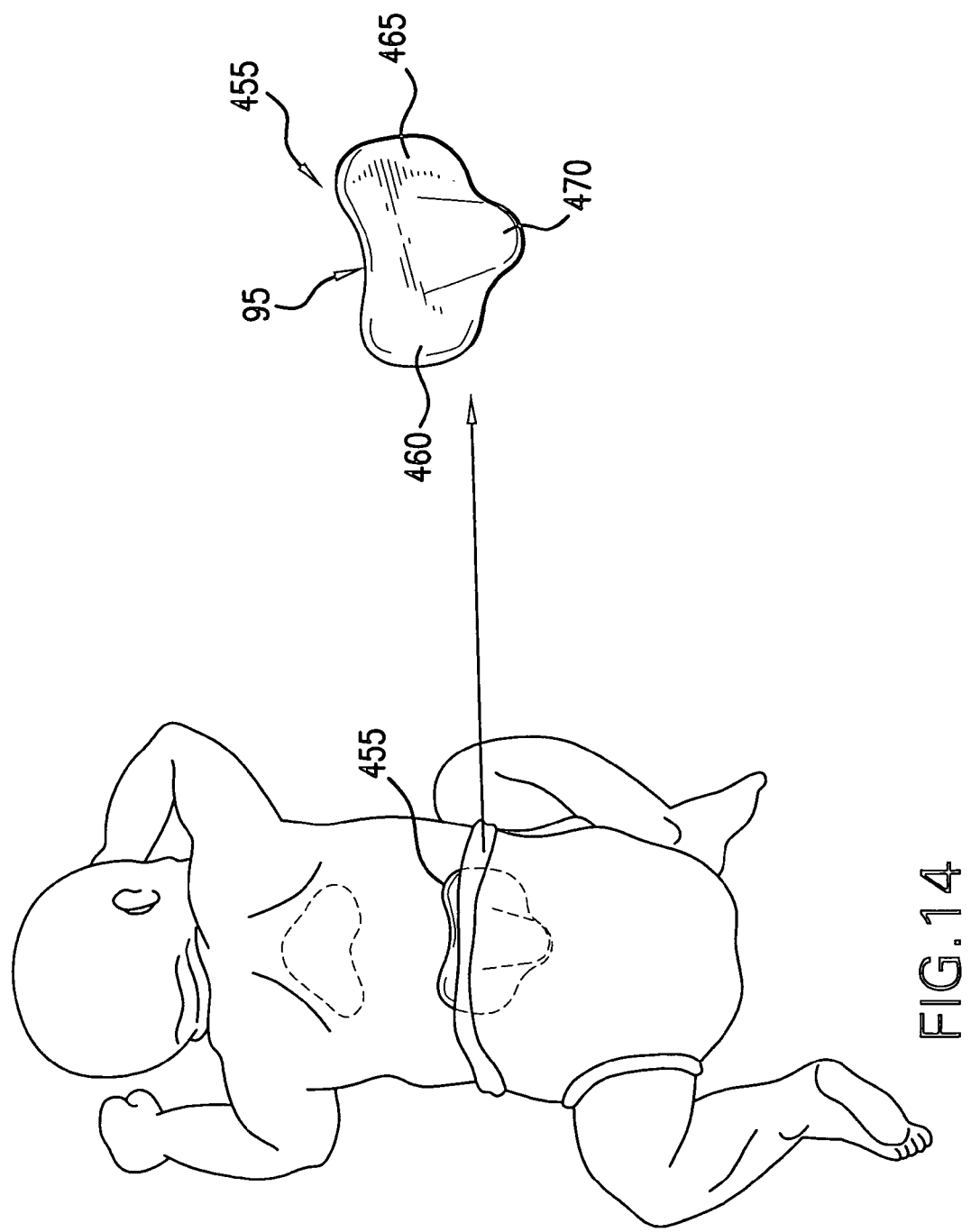
FIG. 14 is a tenth embodiment of the temperature measurement module.

FIG. 14 illustrates a tenth embodiment of module 55, which is a posterior mounted module 455, and its placements on the wearer. Posterior module 455 is constructed of a malleable, soft body-forming material, preferably a soft nonwoven multilayered material, but may also be a flexible urethane or an elastomeric material such as rubber or a rubber-silicone blend by a molding process. Alternatively, posterior module 455 may also be constructed from a rigid plastic material which is otherwise padded or adhered to the body consistent with the embodiments described above. Consistent with the other modules, posterior module 455 has a housing (not shown), which further comprises a left wing portion 460 and a right wing portion 455. A central portion 470 of posterior module 455 is located between the left and right wing portions. Posterior module 455 may slip into a pouch built into diaper or be positioned in between diaper 60 and small of back of wearer. Additionally the module may be adhesively mounted, as described previously, in the upper portion of the back between the shoulder blades as illustrated in FIG. 14 by chain line.

Figure 15:
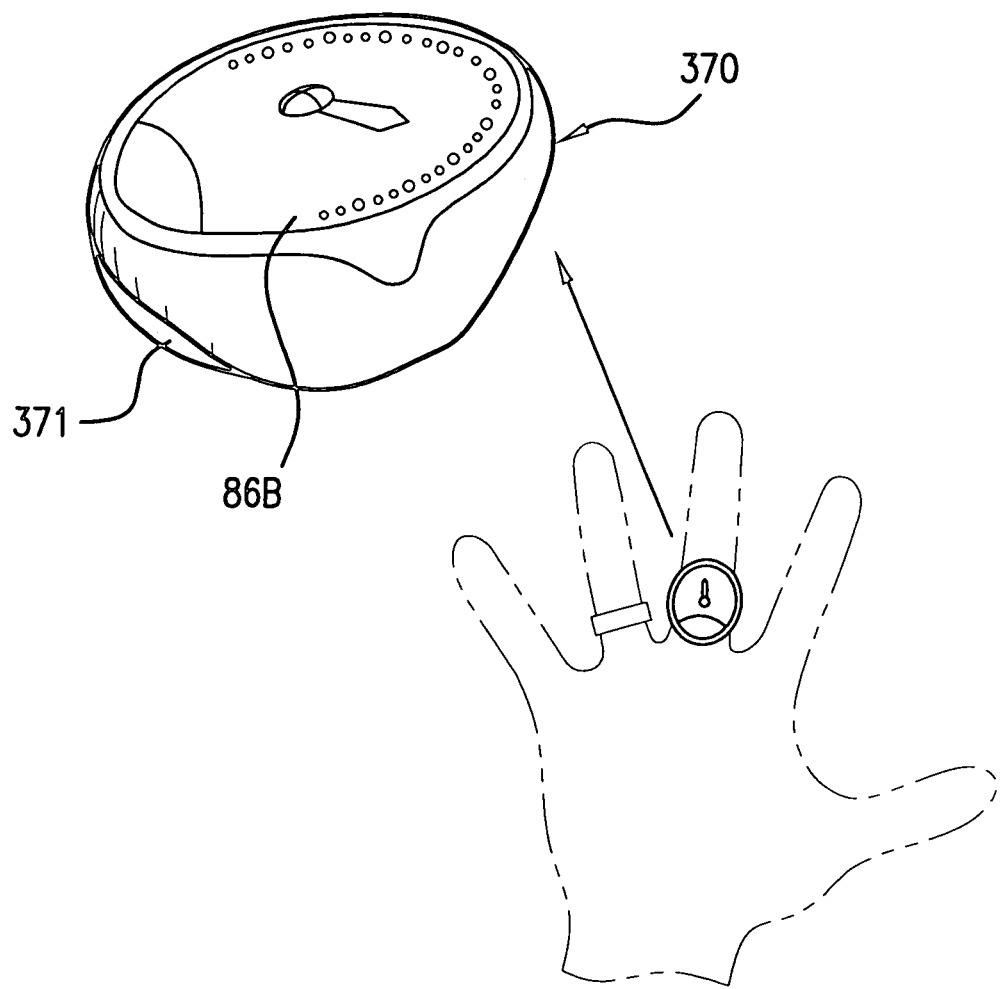
FIG. 15 is an eleventh embodiment of the temperature measurement module.
Figure 16:
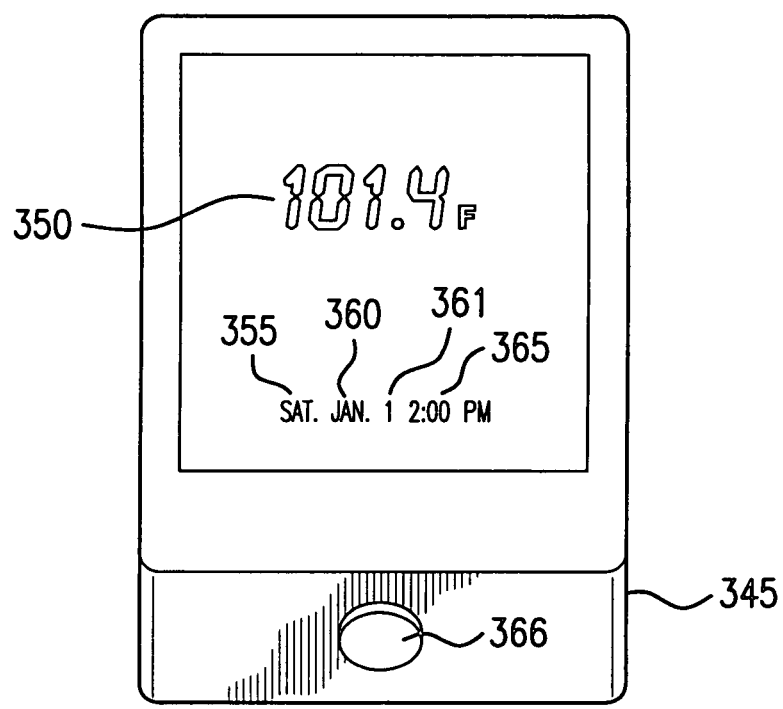
FIG. 16 is a diagrammatic representation of a first embodiment of a receiver.

Finally, FIG. 15 illustrates an eleventh embodiment of the receiver in the form of a ring 370. Ring 370 may be a receiver but may also be a self contained single module unit as previously described. Base 371 is constructed from a flexible urethane or an elastomeric material such as rubber or a rubber-silicone blend by a molding process, although base 371 may also be constructed from a rigid plastic material. Base 371 contains all of the necessary components for receiving data from a separate module 55, or may contain all of the components of module 55 itself and take temperature readings from the finger itself. The temperature and other relevant data received from module 55 is displayed on display 86B of base 371. Base 371 is sized to fit on an appropriate finger of an individual. Receiver ring 370 provides portability and mobility to the user so that the user can move to a distance within the area as defined by the transmission method used by module 55 to transmit data to receiver ring 370. In the embodiment shown in FIG. 15, an analog display is provided with respect to display 86B. It is to be specifically noted that any display of any embodiment may be digital or analog, electronic, or electromechanical. Displays may be instantaneous, as will be described more fully herein, or may be cumulative, in the sense that temperature trends may be displayed. With respect to display 86B in FIG. 15, the display could be a typical thermometer gauge which displays the current temperature on a relative scale. This device may be particularly useful as an ovulation detector or contraceptive indicator for women, and may be enabled to indicate peak temperatures over a time period to assist in determining ovulation, for example, 30 days, with a power source matched for such length of intended use. Additionally, it may be utilized, similar to the bathroom training embodiment above, for detecting pre-menstrual signals and provide a warning regarding the impending event. This may be useful for a number of applications, including familiarizing and/or educating young women with little menstrual experience about anticipating and addressing their needs. This application has equal utility for use with menopausal women, in that these temperature readings may be utilized in detecting, characterizing, trending and predicting hot flashes and managing this change in life.

It is important to note that the embodiments described above are, in conjunction with the circuitry and programming described below, adapted for use with all types of patients and wearers. For example for adults who do not wear diapers, the clip modules could be clipped onto a person's underwear. The devices are generally intended to be preprogrammed with appropriate information, algorithms and flexibility to adapt to any wearer and to calibrate itself to that particular use. Other embodiments, most notably the disposable embodiments described above, may also be further reduced in complexity and cost by limiting the functionality of the device. This may be done in an effort to produce the lowest cost embodiment or to increase the specificity of the application for which the device is intended. In either case, functionality may be limited by reducing the processing capabilities of the device, as will be described in more detail herein and/or by reducing the available range of functions. The functional range of each device may be limited, for example, to a certain weight range for the patients, so that infants, children and adults will each receive a different type of monitoring device. Moreover, as weight has a primary effect on the data derivation, as will be described more fully herein, finer gradations of weight applicability may be developed and preprogrammed into a series of specific weight range products. Additionally, other responsive parameters may be determined to permit differentiation between embodiments, with a training device worn for some initial period to allow the system to categorize the user according to a particular parameter or characteristic, the output of which is a determination of which of a series of alternative devices is appropriate for the user. By having several modules for different sizes of users or, alternatively, the adhesive or garment type, the module may be provided with a built in estimate of the size of the user which it may incorporate into its calculations without having to have that size input explicitly.

A typical receiver 345 and example of a display is illustrated in FIG. 10. The display may be incorporated into any one of the receivers as discussed with respect to FIG. 1. A current temperature 350 is shown on the display and is the latest calculated temperature of the individual as determined from the detected measurements of module 55. The calculation of the temperature is further described herein with respect to FIG. 22. The display of receiver 345 is further adapted to include other information such as current day of week 355, current month 360, current date 361 and current time 365. The operational status of receiver 345 is controlled by power button 366. Delivery of battery or electrical power to the receiver 345 is regulated by the depression or other manipulation of power button 366. Upon power delivery, the receiver 345 will begin to receive signals from module 55. Receiver 345 displays feedback from the modules, which may be as simple as an iconic or color based indicator relating to daily activity level or body fatigue, such as is when working in a surgical, fire retardant, biological or hazardous material suit where the body is unable to breathe as was previously described. The results may also convey and indication that a threshold was met. In addition the display may be divided by chronology, calendar and the like.

Figure 17:
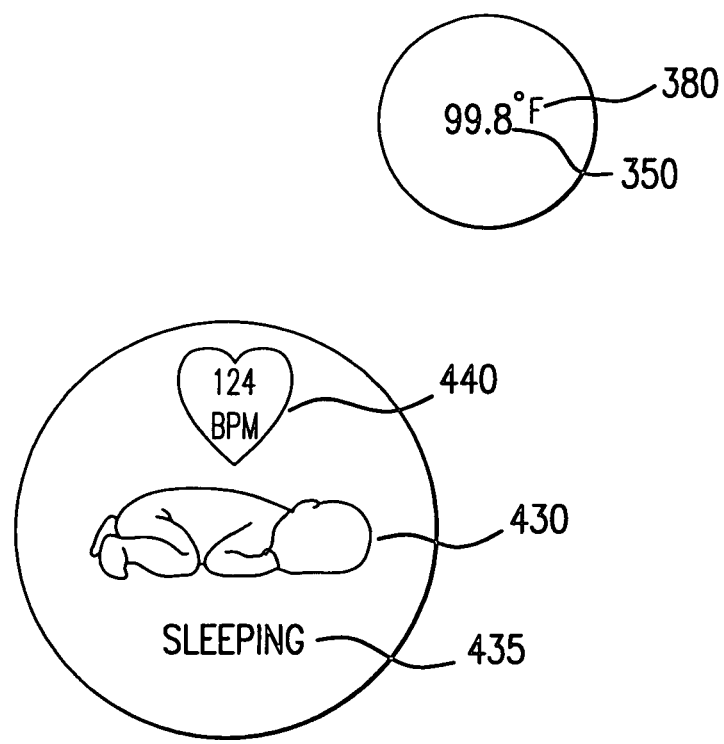
FIG. 17 is a diagrammatic representation of a receiver display.

As temperature changes, the display can also present an iconic, analog or digital indication as to the trend of change, such as moving the digits up or down similar to an odometer to indicate rising or falling temperatures, respectively. Graphical or iconic output may incorporate sleeping, crying and/or orientation for example. As shown in FIG. 17, an iconic presentation is illustrated, having current temperature 350 be the latest calculated temperature of the individual as determined from the detected measurements of module 55. Current temperature 350 can be displayed in Celsius or in Fahrenheit mode and the mode selected for display is indicated by temperature scale indicator 380 and displays a C for Celsius or an F for Fahrenheit. The display includes an orientation indicator icon 430. Orientation indicator icon 430 provides an iconic representation of the orientation of wearer. The orientation indicator icon 430 can be a sound or an illustration or icon of an individual in a certain body position or orientation indicator icon 430 can be a alphabetical symbol such as L for left, R for right, S for stomach and B for back. The display further provides an activity indicator text 435. The activity indicator text 435 provides information on the activity level of the wearer to indicate if the wearer is sleeping, awake or crying. Heart rate indicator 440 provides a measurement of the heart rate of the wearer. Heart rate indicator may be replaced by an indicator that displays one of another type of vital sign status.

Figure 18A:
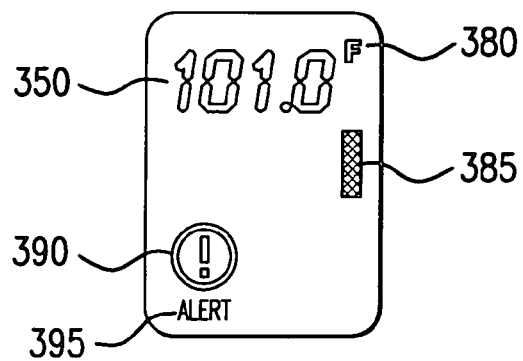
FIGS. 18A-C are additional diagrammatic representations of a receiver display.

FIG. 18A illustrates a display of receiver 345. The current temperature 350 is the latest calculated temperature of the individual as determined from the detected measurements of module 55. The calculation of the temperature is further described herein with respect to FIG. 23. Current temperature 350 can be displayed in Celsius or in Fahrenheit mode and the mode selected for display on receiver 345 is indicated by temperature scale indicator 380 and displays a C for Celsius or an F for Fahrenheit. Battery indicator 385 indicates the power level of the battery of module 55 or the selected alternative embodiment. Abnormal temperature alert indicator icon 390 flashes a visible alert when a borderline low or high temperature is detected. The high temperature alert indicator 390 may be accompanied by abnormal temperature alert text 395 which is high temperature alert indicator 390 in a textual format. Display 86B may also be rendered as a tactile device, a motor, electronic stimulation or other technologies for use by the visually impaired, including, but not limited to an array of reading pins to create a moving Braille-like display, as developed by NASA's Jet Propulsion Laboratory.

Figure 18B:
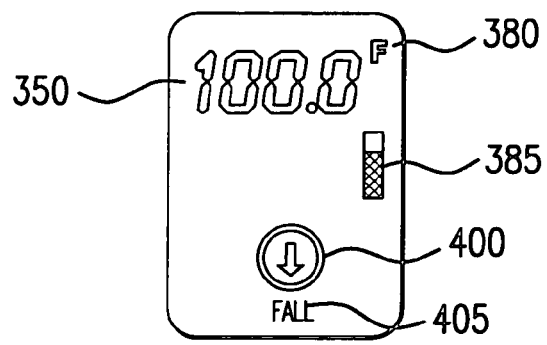

FIG. 18B represents a second embodiment of a display of receiver 345. The display includes current temperature 350, temperature scale indicator 380 and battery indicator 385, as described with respect to FIG. 18A. In addition, the display includes quick shift alert indicator icon 400 that visibly alerts the user when the temperature changes by a preprogrammed number of degrees in either a rising or falling temperature state or any other rapid change in condition or context. The quick shift alert 400 may be accompanied by quick shift alert text 405 that illustrates the quick shift alert 400 in a textual format.

Figure 18C:
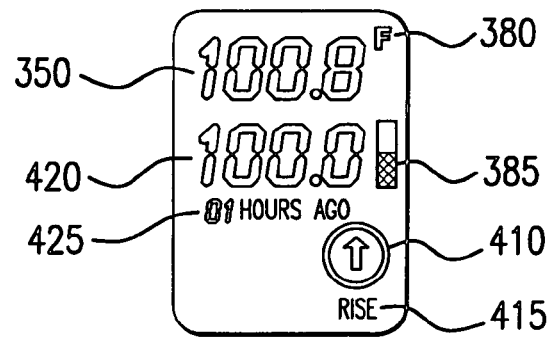

A third embodiment of the display of receiver 345 is shown in FIG. 18C. The display includes current temperature 350, current temperature indicator 380, battery indicator 385, as described with respect to FIG. 18A. The display also includes temperature trend information including a previous temperature 420 which indicates a previous temperature as detected by module 55, the calculation of which is further described with respect to FIG. 22. Previous temperature 420 has an associated previous temperature time text 425 which indicates the time at which the detected previous temperature 420 was current. The display illustrated in FIG. 18C further includes a temperature trend indicator icon 410, which is an iconic representation of the pattern of temperature over a certain period of time, and temperature trend indicator text 415 which is the textual representation of temperature trend indicator icon 410. It is to be specifically noted that the receiver and related displays may be incorporated into any other device commonly found in the home, office, health care institution or the like, including but not limited to a weight scale, television, phone base station or hand set, exercise equipment, blood pressure monitor, glucometer or clock radio.

FIG. 19 shows an electrical block diagram of the circuitry of a module 55. Module 55 includes a first sensor 610 and a second sensor 615. First sensor 610 is a skin temperature sensor that detects the skin temperature of the body at the skin area of placement on the wearer and generates a signal to be sent to a processor 605. Second sensor 615 is an ambient temperature sensor which detects the ambient air temperature of the environment of the wearer and also generates a signal to be sent to processor 605. Depending upon the nature of the signal generated by second sensor 615, the signal can be sent through amplifier 635 for amplification. Once the signals generated by second sensors 615 are sent to processor 605, the signals may be converted to a digital signal by an analog-to-digital converter contained with the processor 605.

A digital signal or signals representing detected temperature data and/or other relevant information of the individual user is then utilized by processor 605 to calculate or generate current temperature data and temperature data trends. Processor 605 is programmed and/or otherwise adapted to include the utilities and algorithms necessary to create calculated temperature and other related data.

It should be understood that processor 605 may also comprise other forms of processors or processing devices, such as a microcontroller, or any other device that can be programmed to perform the functionality described herein. It is to be specifically noted that the circuitry may be implemented in a minimal cost and component embodiment which may be most applicable to a disposable application of the device. In this embodiment, the apparatus is not provided with a processor, but as series of discrete electrical components and gate circuits for highly specialized preprogrammed operation in accordance with any of the embodiments described herein. This apparatus may be powered by any known means, including motion, battery, capacitor, solar power. RFID or other methods known to those skilled in the art. Another option is to power the apparatus directly from the voltage potentials being measured. The display mechanism may be chemical, LCD or other low power consumption device. The voltage spikes charge up a capacitor with a very slow trickle release; a simple LED display shows off the charge in the capacitor. In another embodiment, a simple analog display is powered by the battery.

The detected or processed data and/or other relevant information of the individual user can be sent to memory, which can be flash memory, contained within processor 605. Memory may be part of the processor 605 as illustrated by FIG. 20 or it may be a discrete element such as memory 656 as shown in FIG. 20. To the extent that a clock circuit is not included in processor 605, a crystal timing circuit 657 is provided, as illustrated in FIG. 20. It is specifically contemplated that processor 605 comprises an A/D converter circuit. To the extent such is not provided, an A/D circuit (not shown) may be required. Sensor input channels may also be multiplexed as necessary.

Battery 620 is the main power source for module 55 and is coupled to processor 620. A transceiver 625 is coupled to processor 620 and is adapted to transmit signals to a receiver in connection with module 55. Transceiver communicates detected and/or processed data to receiver by any form of wireless transmission as is known to those skilled in the art, such as infrared or an RF transmission. Antenna 630 is further coupled to processor 605 for transmitting detected and/or processed data to the receiver. Antenna 630 may further be mounted or incorporated into a diaper, garment, strap or the like to improve signal quality.

FIG. 20 illustrates an electrical block diagram of a stand alone version of module 55. The stand alone version of module 55 provides a means for user input 655. User input 655 may include initial temperature measurement as manually measured by user or characteristics of the wearer such as age, weight, gender or location of the module. Module 55 includes a first sensor 610 and a second sensor 615. First sensor 610 is a skin temperature sensor that detects the skin temperature of the body at the skin area of placement on the wearer and generates a signal to be sent to processor 605. Second sensor 615 is an ambient temperature sensor which detects the ambient air temperature of the environment of the wearer and also generates a signal to be sent to processor 605. Temperature sensors are generally implemented as thermistors, although any temperature sensing devices are appropriate. These sensors generally comprise 1% surface mount thermistors applied using standard automated SMT placement and soldering equipment. A 1% R25 error and 3% Beta error for each sensor means that each sensor is +/−0.5 degrees C. around the 35 degree C. area of interest. In certain circumstances, this may result in a 1 degree C. error in temperature reading between the two sensors. To reduce error, the sensor is submerged into a thermally conductive but electrically insulative fluid, such as 3M Engineered Fluids Fluorinert and Novec, and allowed to stabilize. By reading the two thermistors under this known condition of identical temperatures at two temperature setpoints, the relationship between the R25 and Beta of the two thermistors may be determined.

It is also possible to incorporate more costly thermistors with 0.1 degree C. interchangeability. This reduces the inter-sensor error by a factor of 10 to 0.1 degree C. It is also possible to match sensors during the manufacturing process utilizing a batching process as would be known to those skilled in the art.

A digital signal or signals representing detected temperature data and/or other relevant information of the individual user is then utilized by processor 605 to calculate or generate current temperature data and temperature data trends. Processor 605 is programmed and/or otherwise adapted to include the utilities and algorithms necessary to create calculated temperature and other related data. Processor 605 may also comprise other forms of processors or processing devices, such as a microcontroller, or any other device that can be programmed to perform the functionality described herein Battery 620 is the main power source or module 55 and is coupled to processor 620. Module 55 is provided with output 86A that presents multi component system includes module 55 that may be provided with display 86A for visual display of current temperature, temperature trends, and contextual data. Alerts can be reported in many non-visual forms as well, such as audio, tactile, haptic and olfactory, for example. Alerts may also be made through a computer network or by wireless transmission.

FIGS. 21A and 21B illustrate an electrical block diagram of a multi component system incorporating module 55. FIG. 22A contains all of the components as described in FIG. 21 with respect to the stand-alone version of module 55. In addition, module 55 further comprises a transceiver 625 is coupled to processor 620 which is adapted to transmit signals to a receiver in connection with module 55. Transceiver communicates detected and/or processed data to receiver by a short range wireless transmission, such as infrared or an RF transmission. Antenna 630 is further coupled to processor 605 for transmitting detected and/or processed data to the receiver.

FIG. 21B illustrates the circuitry of a receiver used in connection with module 55. User input 680 may include initial temperature measurement as manually measured by user or characteristics of the wearer such as age or weight. Processor 675 receives processed data from module 55 as current temperature data, and temperature data trends and contextual data. Process 675 may be programmed and/or otherwise adapted to include the utilities and algorithms necessary to create calculated temperature and other related data. Digital signal or signals representing detected temperature data and/or other relevant information of the individual user may be received and utilized by processor 675 to calculate or generate current temperature data, temperature data trends and contextual data. Processor 675 may also comprise other forms of processors or processing devices, such as a microcontroller, or any other device that can be programmed to perform the functionality described herein. An RF receiver 670 is coupled to processor 675 and is adapted to receive signals from transceiver of module 55. RF receiver 670 receives processed data by a short range wireless transmission, as previously described. Antenna 665 is further coupled to processor 605 for transmitting detected and/or processed data to the receiver. The antenna, in order to be longer and have been transmission qualities could be integrated into the adhesive. Transmission means may include, for example, RF, IR, sound and protocols such as Ethernet, Bluetooth, 802.11, Zigbee and GPRS.

It is to be specifically noted that any of the programmable features of the devices may be rendered as series of discrete circuits, logic gates or analog components in order to reduce cost, weight or complexity of the device which may be developed by the algorithmic method described in Andre, et al., copending U.S. patent application Ser. No. 09/682,293. This is especially true with respect to the disposable embodiments and more particularly, the graded or categorized devices described above.

Battery 620 is the main power source for receiver and is coupled to processor 670. The battery 620 may be recharged by induction or wireless communication. Another alternative is the use of RFID systems, where the internal power reserve of the unit is merely enough to store data until more fully powered by being showered by RF signals.

The device may be further enabled, in conjunction with RFID systems, to send a data bit to a reader or when a wand is waved over or brought in proximity to the wearer. With the wireless capability, there is also the capability to have other passive RFID tags, such as stickers, placed around the house at locations that are unsafe, such as a stairway. In this embodiment, a warning could be sounded or sent to a receiver if the wearer approaches the RFID tag denoting a dangerous location. This may be implemented in a fully powered embodiment or in a product that is externally powered.

An alternative power system, such as that developed by Firefly Power Technologies, Pittsburgh, Pa. is another subtle variant with regards to powering products. In that system, by either collecting the ambient magnetic field or RF bandwidth or alternatively showering an area with a known and consistent RF bandwidth powers a module having only a capacitor and no battery, which is trickle charged until a certain power capacity is collected or a certain amount of time has passed. The unit is then powered up, the necessary readings taken/recorded and then passed on wirelessly with acknowledgement that the data reached the destination or held in flash memory until the next time the power up and wireless connection is initiated and established. The unit would then power down and begin its next cycle or recharge. Aura Communications' LibertyLink chip is another alternative that creates a weak magnetic field bubble and transmits by modulating the magnetic field at low frequencies of approximately 10 MHz.

Figure 22:
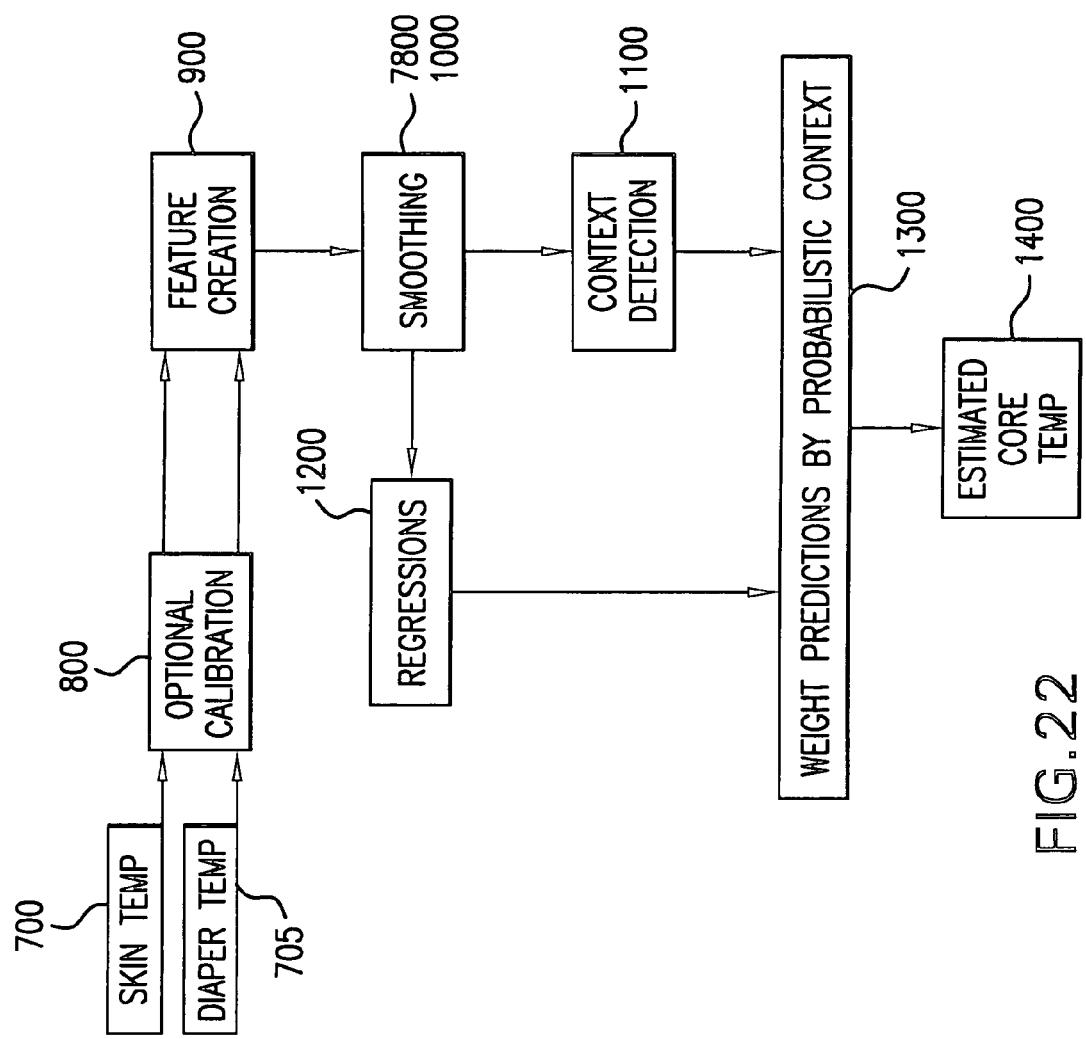
FIG. 22 is a logic diagram illustrating the operation of the temperature measurement module.

FIG. 22 illustrates the gross operation of a temperature measurement module. Skin temperature sensor initially detects skin temperature 700 and ambient temperature sensor initially detects a diaper temperature 705 corresponding to the ambient environment of the individual. The module is subject to calibration 800 to aid in the accuracy of the detection of skin temperature by skin temperature sensor. One method of calibration includes the temperature measurement of the wearer with a digital temperature measurement device which is automatically transferred to the module. Once the initial temperature of the wearer is received by the module, the unit is set to the wearer's initial starting temperature and uses this temperature as a basis for the relative changes that occur while the temperature module is in contact with the wearer.

If an initial temperature of the wearer is not received through a baseline calibration, the module will calibrate itself over a period of time after being on the body, as well as adapt and/or modify the calculations and/or algorithms over time as part of a learning process, as described more fully in Andre, et al., copending U.S. patent application Ser. No. 10/682,293 and others identified above. During this time of initial wear, while the module is being calibrated, any particular unexpected changes in temperature are stored for later characterization. The module creates a history of measurements that are categorized for further contextual analysis as similar unexpected values are detected.

In detail, calibration 800 can take one of two embodiments: sensor calibration and personalization of the system to the particular wearer. In sensor calibration, the individual sensors are calibrated against one another based on laboratory adjustments or first readings from the device before each is applied to the skin. The appropriate offset and, optionally, a slope or linear (or non-linear) function are chosen for each sensor. In personalization, a secondary reading of core temperature is taken and utilized for the purposes of calibrating the device to the individual. For example, a parent may take their child's temperature through another means before placing the module on the child. This value can be utilized to personalize the algorithm for that child by correlating the detected measurements of the module with the actual temperature recorded by other means.

Alternatively, detectable events may occur which permit further calibration of the system. As one example, if the module is placed in the diaper in such a way as to have a portion of the sensor, if not the module itself, placed in a way to sense the temperature of urine when freshly present in the diaper, the temperature of this urine, as detected by the ambient sensor, can be utilized to aid in calibrating the module.

However, any readings being made in the diaper, whether for infant, toddler, or adult benefits from the recognition of these events and be able to filter out this noise during, but especially after, the introduction of the urine to the diaper because of the chemical reaction of the diaper which increases temperature momentarily. Additional information can improve the accuracy of the system over time.

Finally, another form of calibration is to input into the system the wearer's age, height, weight, gender or other such personal characteristics. These demographic factors can improve accuracy and serve as an additional input into the system as will be more fully described herein with specific reference to weight.

To the extent that a particular module is utilized by more than one individual without resetting or clearing the database for that identified unit, wearer identification or demographics may also be embedded in the unit or its associated database of parameters, settings, preferences or values. These may be manually created during set up or may be detected. With continuous measurement of temperature data, including a personalization period at the beginning of each new user's use, the sensor suite may automatically recognize the wearer's biometrics and therefore proactively provide physiologically based identification information. In addition, this product could communicate with an implantable identification chip in the body before it sends a signal from its wearer, detecting and incorporating the body identifier and integrating it into the reading protocol/header.

The step of feature creation 900 takes as input the temperature data or any other sensor data, which may or may not comprise calibrated signals and produces new combinations or manipulations of these signals, such as [skin-temperature]$^3$ or $\sqrt{}$[skin-temperature] which are created for use in the rest of the algorithm. Additional examples include STD, MEAN, MAX, MIN, VAR and first derivatives thereof. Also, features such as insults, another term for urinations, or dislodgements of the sensor can be included as features that are themselves created by utilizing simple event detectors. These detected features can then be utilized as part of regressions 1200. For example, detecting the active presence of fresh, warm urine by identifying the particular data output pattern of sharp rises followed by gradual falls in ambient-side temperature on the femoral modules, then using the maximum value of the rise as an input into the regressions. The feature is predicated on the fact that when a child urinates, the urine is at core body temperature and so can provide an opportunity for calibration of the device against a known parameter.

Figure 23:
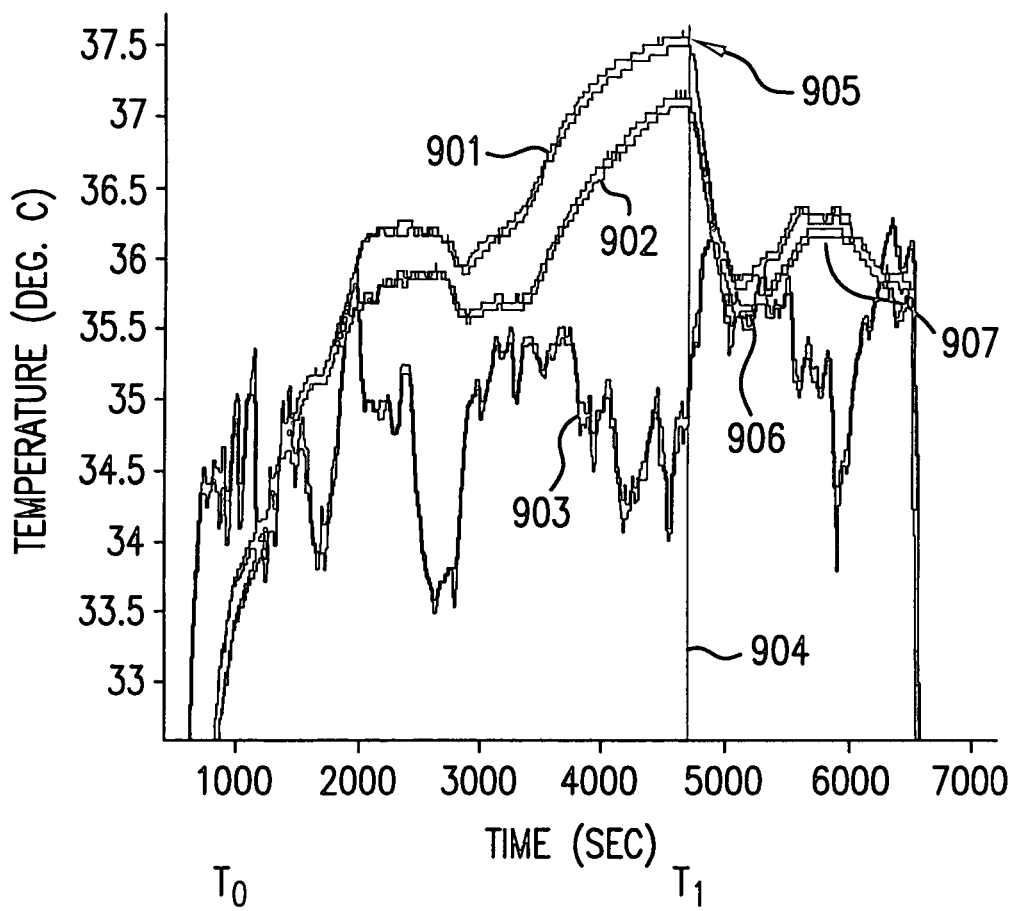
FIG. 23 is a graphical representation of output of the temperature measurement module.
Figure 23A:
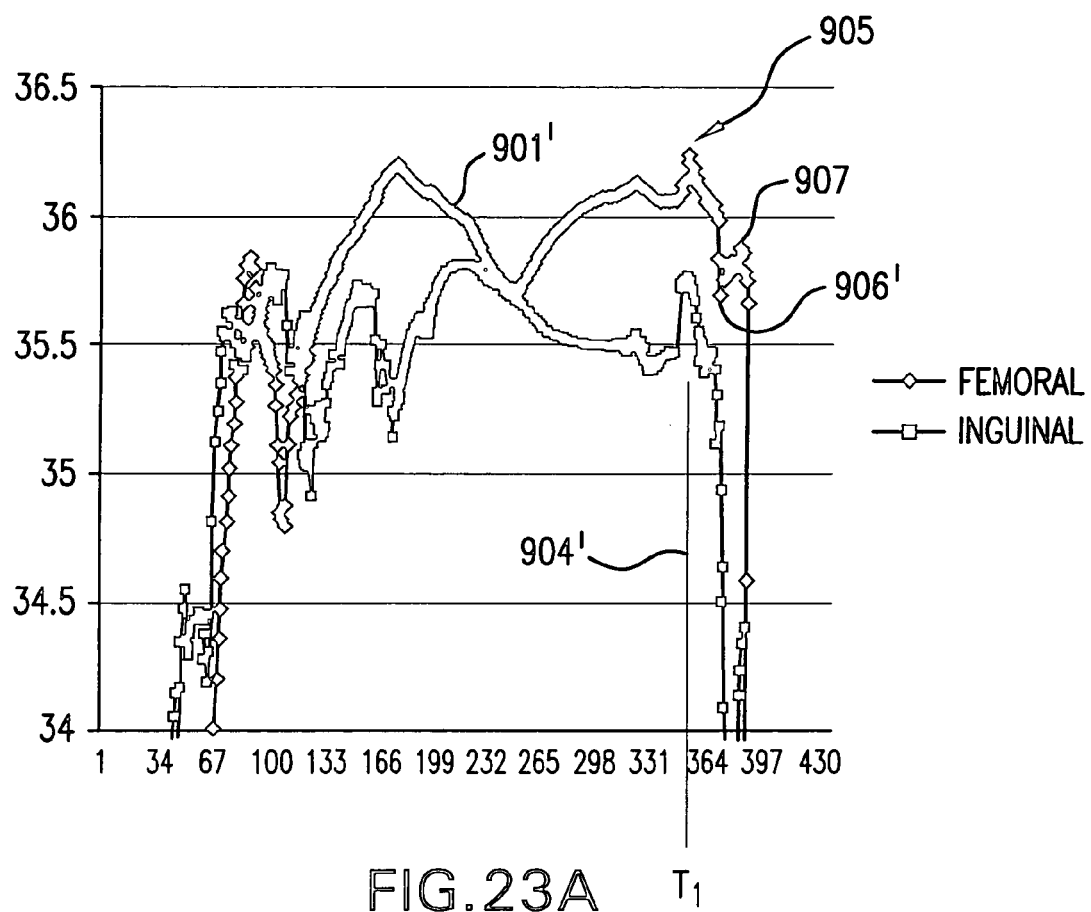
FIG. 23A is a graphical representation of output of the temperature measurement module.

Referring to FIG. 23, a urination insult is graphically illustrated utilizing three sensors in a multi module embodiment, having two femoral modules, identified as left and right and one axillary module. All data is presented from ambient temperature sensor 120 of each module. Left femoral sensor output 901 and right femoral sensor output 902 track relatively similar curves, with a slight variation in detected temperature, which may be caused by variations in the sensor calibrations or slightly different ambient environments within the diaper of the wearer. With respect to FIG. 23, the sensors are not located in the absorbent material of the diaper, and the insult is considered indirect. Axillary sensor output 903 provides a profile which is radically different and provides no information with respect to the insult. Between times $T_0$ and $T_1$, the system is in a warm up phase with the temperature profiles of outputs 901, 902 normalizing to a temperature peak. At time $T_1$, identified by line 904, an insult occurs having peak temperature 905. A characteristic trough 906 in femoral outputs 901, 902 without corresponding changes in axillary output 903 indicates a localized event in the femoral region. The particular shape of trough 906 represents the initial warmth of the core body temperature urine's presence in the diaper and the subsequent cooling of the diaper and liquid. Secondary peak 907 occurs as the now-cooled urine is again warmed by its presence near the body of the wearer. This feature of urination is repeatable and detectable and is an example of the types of pattern, context and event detection referred to within this specification. FIG. 23A provides an illustration of a direct insult, in which the sensor is placed within the absorbent material of the diaper, utilizing a single femoral ambient temperature sensor. This graph provides a more characteristic example of urination or insult detection. At time $T_1$, identified by line 904', an insult occurs having peak temperature 905'. A characteristic trough 906' is once again observed in femoral output 901', representing the initial warmth of the core body temperature urine's presence in the diaper and the subsequent cooling of the diaper and liquid. Secondary peak 907' again is shown as the now-cooled urine is again warmed by its presence near the body of the wearer. Of particular note is the sharp rise or slope of the curve immediately prior to peak temperature 905'. This more characteristic feature of urination is repeatable and detectable and is an example of the types of pattern, context and event detection referred to within this specification. The module is equally adaptable for the detection of feces, which presents a similar impact as urine.

If multiple contexts are simultaneously observed, then several solutions are possible. One embodiment is to consider each combination of contexts to be its own context. Another is to identify a hierarchical order of contexts for choosing which is dominant.

Figure 23B:
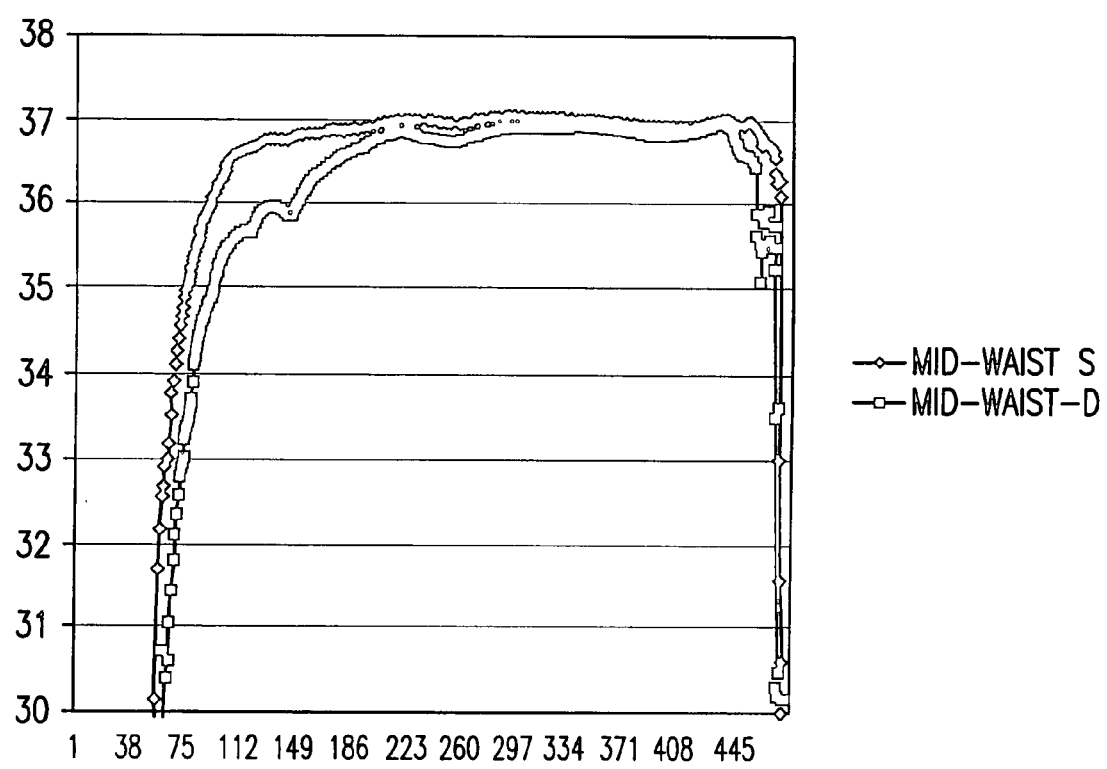
FIG. 23B is a graphical representation of output of the temperature measurement module.

While FIG. 23 does provide some indication of warm up, a more characteristic output is shown in FIG. 23B, which illustrates a less gradual warm up profile than FIG. 23. It is important to note that the warm up phase described with respect to FIGS. 23 and 23B is characteristic of each wearing or use cycle. This warm up phase has standard characteristics and can be easily modeled as a standard context. Simple techniques exist and are well known in the art for adjusting for such standard warm-up curves. These include simple exponential models where the incoming signals are adjusted by a factor based on the time since the module was affixed as well as models where the time since the start of the trial is an input into the regression equations.

Figure 24:
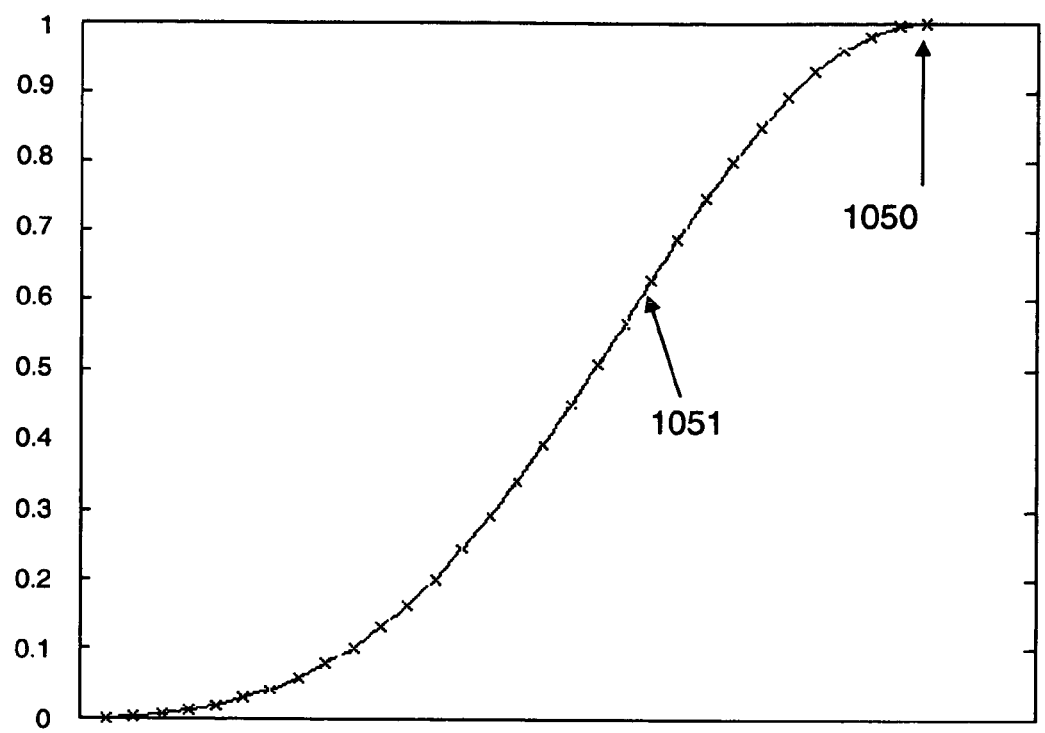
FIG. 24 is a diagrammatical representation of an aspect of the logic utilized in the operation of the temperature measurement module.

Smoothing 1000 utilizes dynamic and/or windowed models of discrete epochs of consecutive data to smooth out noisy values. For example, a Blackman smoother with a window of 30 seconds may be used to smooth out minor second to second variations in both the raw signals and the derived features. In one embodiment, each data point is smoothed according to a Blackman weighting function over the past 30 seconds. This function weights the current point 1050 the most highly and then weights each prior point 1051 to a lesser degree, according to the Blackman function as shown in FIG. 24, illustrating point 1051 as 10 seconds prior in time to point 1050. The function for a given point is calculated as the sum of the weighted recorded values divided by the sum of the weights. In another embodiment, the mean value of each 30 second window is utilized. In another embodiment, data that deviates by more than a present parameter are ignored. In yet another embodiment, smoothing is done using a probabilistic model such as a dynamic probabilistic network. A variety of exact and approximate algorithms for doing this smoothing exists in the literature.

Regressions 1200 are the equations that compute the estimated core temperature for a given context. These equations can be very complex. One rather simple embodiment is the following:

$$\text{EstimatedCoreTemp} = A*\text{SkinSideTemp} + B*(\text{SkinSideTemp} - \text{AmbientSideTemp})^2 + C$$

Where A, B and C are variable coefficients. Another example equation is:

$$A*\text{weight} + B*\text{back25ModDiff} + C*\text{SqBack25ModDiff} + D*\text{ModMidWaist-}S + E$$

where back25ModDiff is the backward average of the difference between the ambient and the skin sensor for the module over the last 25 seconds, SqBack25ModDiff is the average squared difference between the skin and ambient sensors on the module over the past 25 seconds, ModMidWaistS is the module skin temperature, and E is a constant offset. Another embodiment is to utilize a recognized context or feature for modification of the equation, rather than requiring a separate equation. For example, if a feature WithinInsult is created that represents the offset that is expected to have been caused by an insult rather than a core-body-temperature change, then adding in a factor D*WithinInsult increases the accuracy of the derived temperature. One such embodiment is as follows:

$$\text{EstimatedCoreTemp} = A*\text{SkinSideTemp} + B*(\text{SkinSideTemp} - \text{AmbientSideTemp})^2 + D*\text{WithinInsult} + E*\text{warmUpEffect} + C.$$

Context detection 1100 recognizes and incorporates events, conditions, and activities that affect the thermoregulatory properties of the wearer, which are detected and taken into account. For example, warm-up curves due to initial placement or dislodgement, urination heat-up and cool-down events, physical activity, and rest can all be detected. These contexts are detected by any of a variety of techniques, including but not limited to template matching, wavelet matching, decision trees, dynamic belief nets, neural nets, support vector machines, or rule-based detectors. One such example of a detector is a very simple rule for warmup that equates any minute within 15 minutes of a sharp up-swing in skin-side temperature, defined as more than a one degree change within 30 seconds. Other contextual filtering may also be necessary, such as a baby moving around, the diaper being taken off, clothing being taken off, lifting up the arm, dislodgements, and the like. Dislodgement recognition may also be enhanced by the inclusion of a heat flux sensor. In the preferred embodiment, these detectors are probabilistic.

In the preferred embodiment, in weighting step 1300, two main contexts are utilized, active and not-active. In this case, the estimates of the probability of being active created by a probabilistic activity detector, such as a naïve Bayes algorithm or a dynamic belief network are first created. These are identified as P(context|Data). The predictions from each equation are then weighted by the probability of the associated context. If eq_active and eq_rest are two equations for predicting core-body temperature, then:

$$P(active|Data)*eq\_active+P(rest|Data)*eq\_rest$$

is the equation for the estimate of core-body temperature.

Another embodiment utilizes features that correspond to adjusted values of the original temperature signals. For example, if a dip or a rise is explained by other factors, such as an insult or an environmental disturbance, it can be smoothed out to produce a more accurate signal to use in the equations.

Figure 24A:
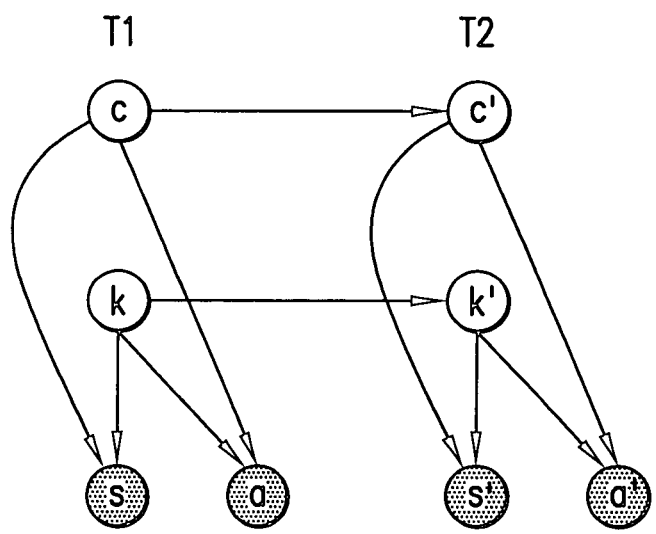
FIG. 24A is a diagrammatical representation of an aspect of the logic utilized in the operation of the temperature measurement module.

Another embodiment is to utilize dynamic belief nets for the entire system. Referring to FIG. 24A, a simple structure is illustrated of a dynamic probabilistic network. T1 and T2 represent time-slices. C and c' are the core temperature at time T1 and time T2, respectively. K and k' are the context at time 1 and time 2. S and s' are skin temperatures and a and a' are the ambient temperatures. The arrows indicate causal links. The joint probability of the above system can be specified by the following set of probability functions:

$$P(c),p(c'|c),p(k),p(k'|k),p(s|k,c),p(a|k,c).$$

Through the use of standard techniques from the graphical models literature, an inference can be drawn computing the most likely core temperatures over a period of time. Smoothing and context detection can be directly performed by selecting an appropriate number of allowed contexts and using standard techniques for training. An alternative embodiment would utilize p(s'|k, c, s, a) instead of just p(s|k,c). This introduces a time dependence to the raw sensors which can improve smoothing.

The computational aspects of regressions 1200 are further refined as a method of creating output data which is more accurate and representative of the wearer's actual parameters than many prior art devices. In many cases, prior art devices and systems utilize a particular aspect of measured data in order to reference a database of compiled average data. In many cases, this presents the appearance of individual data and real-time accuracy, but in fact presents only a weighted average. For a simple example, a typical treadmill permits the input of the user's weight and detects the time and speed of the user's activity. A database is provided with average values of calories expended for a user at each weight gradation point per unit time. A simple relationship is made between the appropriate weight range, the time of activity and the relative amount of exertion, such as speed and distance. The present embodiments described herein are directed toward the actual detection of the relevant physiological parameters necessary to derive the actual condition of the user without reference to average or other pre-selected data libraries. In particular, mathematical functions and/or algorithms are presented in which the value of one detected parameter effects how other detected parameters are mathematically treated. One example is a system having two input variables X and Y, which represent the detected data streams from sensors and a function KNN which is an abbreviation for K (a variable) Nearest Neighbors.

In this algorithm there is presented a set of data points for which the actual relevant values are known. In the example, a plane contains a number of points. Each point has a value of O, therefore each point x1,y1 has a value of O(x1,y1). Applying this to the current system, X may be the detected values of skin temperature, Y could be the detected values of ambient temperature and O could be the true value of the rectal temperature measured for that particular pair of measurements. K, a constant, is selected, usually a small value. In the degenerative case it could be 1, which degenerates KNN to a lookup table, but typically K would be around 3 to 7. Next, a distance metric is selected for the system. The degenerative case is that all units are treated equally, but in the system where X is the skin temperature and Y is the ambient temperature, the distance between two points in the X direction may be more significant than in the Y direction. This may be accounted for by, for example, multiplying all X values by 2. Next, a contribution function is selected. For example, in attempting to predict the value O for a nearby point x2, y2, based upon O(x1,y1), a significant consideration is the predicted distance from x2,y2 to x1,y1. The distance between x2,y2 and x1,y1 is established as D(x2,y2,x1,y1)) and may be calculated or predicted as abs(x2−x1)+abs(y2−y1) where abs is the absolute value. This is identified as the Manhattan distance but is not the most typical way to calculate or predict the distance in association with the KNN function. More typically D(x2,y2, x1,y1) is defined as sqrt((x2−x1)*(x2−x1)+(y2−y1)*(y2−y1)) where sqrt is the square root.

In this system, an algorithm must be developed to predict the correct value for some new point x',y'. This will include the steps of: finding the closest K points in your data space to x',y' which we'll call x1,y1 through xk,yk. Next, the value of O(x',y') is set as the weighted average of O(xn,yn) for n=1 to K where the relative weight for xn,yn is $1/D(x',y',xn,yn)^2$. This provides an example of how data KNN is using a data space of preselected data as the core of its algorithm. It should be noted that KNN is using that data not simply to return some prior output value but to return some newly constructed output value which is particularly appropriate given the sensed values of X and Y. The values of O for each data point may be retrieved from such a preselected database. In choosing not to do so and by actually making the calculations as described herein, this technique presents the opportunity to find non-linear features of the data that exist between the known points. If K=1, then the process devolves to merely retrieving the data from a preselected data set or a lookup table. When K>1, however, then the opportunity is presented for the process to find new facts in the data that don't exist in any of the data points by themselves.

A simple symbolic example in which the value of one detected parameter affects how other detected parameters are mathematically treated is: If X is an even number, Result=X+ Y, if X is an odd number, Result=X−Y. In this example Y has its contribution radically changed depending on the value of X. When X=18 and Y=9 the result is 27. But if X goes up by 1, the result is 10 because of how Y was used has changed so drastically. Another example is: if Y is even, divide by 2, else Y=3*Y+1, and repeat the process X times using the previous output. When complete, return the end value of Y. This is a case where the value of X makes a substantial difference in how Y affects the outcome because where you stop on the growing or shrinking of Y is decided very sensitively by the value of X. While more complex examples may be developed, the essence of these examples is that when utilizing conditional statements, the same results cannot be derived from a fixed formula, database of preselected values, or a lookup table. Another important aspect of the system is that the result of such a conditional test is not itself the answer or final output of the derivation but is instead an equation to be evaluated or a procedure to be executed which in turn produces the answer or output. Other examples include artificial neural networks, decision trees, dynamic belief nets, support vector machines, and hierarchical learned algorithms which create this same qualitative improvement in potential functionality over lookup tables.

Although one can view an algorithm as taking raw sensor values or signals as input, performing computation, and then producing a desired output, it is useful in one preferred embodiment to view the algorithm as a series of derivations that are applied to the raw sensor values. Each derivation produces a signal referred to as a derived channel. The raw sensor values or signals are also referred to as channels, specifically raw channels rather than derived channels. These derivations, also referred to as functions, can be simple or complex but are applied according to an algorithm on the raw values and, possibly, on already existing derived channels. The first derivation must, of course, only take as input raw sensor signals and other available baseline information such as manually entered data and demographic information about the subject, but subsequent derivations can take as input previously derived channels. Note that one can easily determine, from the order of application of derivations, the particular channels utilized to derive a given derived channel.

One aspect of the present invention relates to a sophisticated algorithm development process for creating these algorithms for generating information relating to a variety of variables from the data received from the plurality of physiological and/or contextual sensors. Such variables may include, without limitation, body temperature, energy expenditure, including resting, active and total values, daily caloric intake, sleep states, including in bed, sleep onset, sleep interruptions, wake, and out of bed, and activity states, including exercising, sitting, traveling in a motor vehicle, and lying down, and the algorithms for generating values for such variables may be based on data from various additional sensors such as an accelerometer, heat flux sensor, galvanic skin response sensor and the heart rate sensor, including an array of any of the above, in the embodiment described above.

Note that there are several types of algorithms that can be computed. For example, and without limitation, these include algorithms for predicting user characteristics, continual measurements, durative contexts, instantaneous events, and cumulative conditions. User characteristics include permanent and semi-permanent parameters of the wearer, including aspects such as weight, height, and wearer identity. An example of a continual measurement is the skin, body and near ambient temperatures and related contexts identified herein. Durative contexts are behaviors that last some period of time, such as sleeping, driving a car, or jogging. Instantaneous events are those that occur at a fixed or over a very short time period, such as an infant urinating in a diaper. Cumulative conditions are those where the person's condition can be deduced from their behavior over some previous period of time. For example, if a person hasn't slept in 36 hours and hasn't eaten in 10 hours, it is likely that they are fatigued. Table 1 below shows numerous examples of specific personal characteristics, continual measurements, durative measurements, instantaneous events, and cumulative conditions.

TABLE 1

| | |
|---|---|
| personal characteristics | age, sex, weight, gender, athletic ability, conditioning, disease, height, susceptibility to disease, activity level, individual detection, handedness, metabolic rate, body composition, similarity to prototypical individuals, genetic factors |
| continual measurements | mood, beat-to-beat variability of heart beats, respiration, energy expenditure, blood glucose levels, level of ketosis, heart rate, stress levels, fatigue levels, alertness levels, blood pressure, readiness, strength, endurance, amenability to interaction, steps per time period, stillness level, body position and orientation, cleanliness, mood or affect, approachability, caloric intake, TEF, XEF, 'in the zone'-ness, active energy expenditure, carbohydrate intake, fat intake, protein intake, hydration levels, truthfulness, sleep quality, sleep state, consciousness level, effects of medication, dosage prediction, water intake, alcohol intake, dizziness, pain, comfort, remaining processing power for new stimuli, proper use of the armband, interest in a topic, relative exertion, location, blood-alcohol level, sexual arousal, white blood cell count, red blood cell count, interest level, attention, nutrient levels, medication levels, pain levels |
| durative measurements | exercise, sleep, lying down, sitting, standing, ambulation, running, walking, biking, stationary biking, road biking, lifting weights, aerobic exercise, anaerobic exercise, strength-building exercise, mind-centering activity, periods of intense emotion, relaxing, watching TV, sedentary, REM detector, eating, in-the-zone, interruptible, general activity detection, sleep stage, heat stress, heat stroke, amenable to teaching/learning, bipolar decompensation, abnormal events (in heart signal, in activity level, measured by the user, etc), startle level, highway driving or riding in a car, airplane travel, helicopter travel, boredom events, sport detection (football, baseball, soccer, etc), studying, reading, intoxication, effect of a drug, sexual rhythms and activity, motorcycle riding, mountain biking, motocross, skiing, snowboarding, user-defined activities, ongoing-pain |
| instantaneous events | falling, heart attack, seizure, sleep arousal events, PVCs, blood sugar abnormality, acute stress or disorientation, emergency, heart arrhythmia, shock, vomiting, rapid blood loss, taking medication, swallowing, sexual orgasm, acute pain, bowel movement, urination, onset of sweating, transitions between activities, lying, telling the truth, laughter |
| cumulative conditions | Alzheimer's, weakness or increased likelihood of falling, drowsiness, fatigue, existence of ketosis, ovulation, pregnancy, disease, illness, fever, edema, anemia, having the flu, hypertension, mental disorders, acute dehydration, hypothermia, being-in-the-zone, increased physical prowess, recovery from injury, recovery from disease, recovery from rehabilitation, risks of disease, life expectancy |

It will be appreciated that the present system may be utilized in a method for doing automatic journaling of a wearer's physiological and contextual states. The system can automatically produce a journal of what activities the user was engaged in, what events occurred, how the user's physiological state changed over time, and when the user experienced or was likely to experience certain conditions. For example, the system can produce a record of when the user exercised, drove a car, slept, was in danger of heat stress, or ate, in addition to recording the user's hydration level, energy expenditure level, sleep levels, and alertness levels throughout a day. These detected conditions can be utilized to time- or event-stamp the data record, to modify certain parameters of the analysis or presentation of the data, as well as trigger certain delayed or real time feedback events.

In some embodiments, the raw signals may first be summarized into channels that are sufficient for later derivations and can be efficiently stored. These channels include derivations such as summation, summation of differences, and averages. Note that although summarizing the high-rate data into compressed channels is useful both for compression and for storing useful features, it may be useful to store some or all segments of high rate data as well, depending on the exact details of the application. In one embodiment, these summary channels are then calibrated to take minor measurable differences in manufacturing into account and to result in values in the appropriate scale and in the correct units. For example, if, during the manufacturing process, a particular temperature sensor was determined to have a slight offset, this offset can be applied, resulting in a derived channel expressing temperature in degrees Celsius.

For purposes of this description, a derivation or function is linear if it is expressed as a weighted combination of its inputs together with some offset. For example, if G and H are two raw or derived channels, then all derivations of the form A*G+B*H+ C, where A, B, and C are constants, is a linear derivation. A derivation is non-linear with respect to its inputs if it can not be expressed as a weighted sum of the inputs with a constant offset. An example of a nonlinear derivation is as follows: if G>7 then return H*9, else return H*3.5+912. A channel is linearly derived if all derivations involved in computing it are linear, and a channel is nonlinearly derived if any of the derivations used in creating it are nonlinear. A channel nonlinearly mediates a derivation if changes in the value of the channel change the computation performed in the derivation, keeping all other inputs to the derivation constant. Additionally a non-linear function may incorporate a number of inputs, either weighted or un-weighted, may be added together and their sum used as the independent variable against a non-linear function such as a Gaussian curve. In this case both small and large values of the sum will result in a value near zero and some narrow range of sums around the "hump" of the Gaussian will return significantly higher values, depending on the exact shape and scale of the Gaussian.

Figure 25:
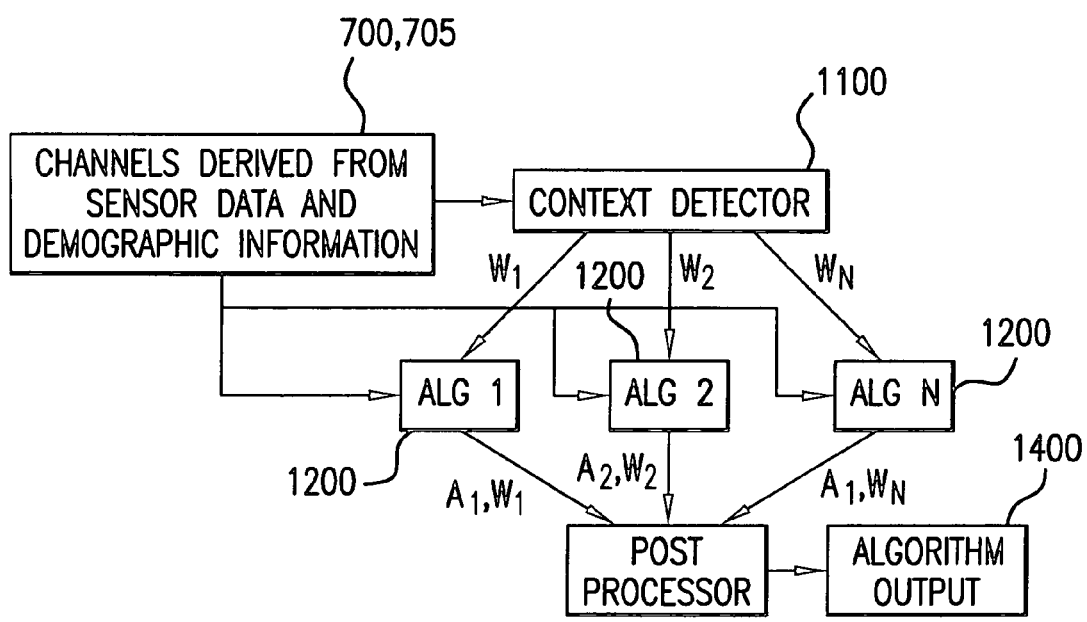
FIG. 25 is a diagrammatical representation of an aspect of the logic utilized in the operation of the temperature measurement module.

Referring now to FIG. 25, the algorithm will take as inputs the channels derived from the sensor data collected by the sensor device from the various sensors 700, 705 and demographic information for the individual. The algorithm includes at least one context detector 1100 that produces a weight, shown as W1 through WN, expressing the probability that a given portion of collected data, such as is collected over a minute, was collected while the wearer was in each of several possible contexts. Such contexts may include whether the individual was at rest or active. In addition, for each context, a regression 1200 is provided where a continuous prediction is computed taking raw or derived channels as input. The individual regressions can be any of a variety of regression equations or methods, including, for example, multivariate linear or polynomial regression, memory based methods, support vector machine regression, neural networks, Gaussian processes, arbitrary procedural functions and the like. Each regression is an estimate of the output of the parameter of interest in the algorithm. Finally, the outputs of each regression algorithm 1200 for each context, shown as A1 through AN, and the weights W1 through WN are combined in a post-processor 1615 which performs the weighting functions described with respect to box 1300 in FIG. 22 and outputs the parameter of interest being measured or predicted by the algorithm, shown in box 1400. In general, the post-processor 1615 can consist of any of many methods for combining the separate contextual predictions, including committee methods, boosting, voting methods, consistency checking, or context based recombination, as previously described.

In addition, algorithms may be developed for other purposes, such as filtering, signal clean-up and noise cancellation for signals measured by a sensor device as described herein. As will be appreciated, the actual algorithm or function that is developed using this method will be highly dependent on the specifics of the sensor device used, such as the specific sensors and placement thereof and the overall structure and geometry of the sensor device. Thus, an algorithm developed with one sensor device will not work as well, if at all, on sensor devices that are not substantially structurally identical to the sensor device used to create the algorithm.

Another aspect of the present invention relates to the ability of the developed algorithms to handle various kinds of uncertainty. Data uncertainty refers to sensor noise and possible sensor failures. Data uncertainty is when one cannot fully trust the data. Under such conditions, for example, if a sensor, for example an accelerometer, fails, the system might conclude that the wearer is sleeping or resting or that no motion is taking place. Under such conditions it is very hard to conclude if the data is bad or if the model that is predicting and making the conclusion is wrong. When an application involves both model and data uncertainties, it is very important to identify the relative magnitudes of the uncertainties associated with data and the model. An intelligent system would notice that the sensor seems to be producing erroneous data and would either switch to alternate algorithms or would, in some cases, be able to fill the gaps intelligently before making any predictions. When neither of these recovery techniques are possible, as was mentioned before, returning a clear statement that an accurate value cannot be returned is often much preferable to returning information from an algorithm that has been determined to be likely to be wrong. Determining when sensors have failed and when data channels are no longer reliable is a non-trivial task because a failed sensor can sometimes result in readings that may seem consistent with some of the other sensors and the data can also fall within the normal operating range of the sensor. Moreover, instead of displaying either of a result or an alarm condition, the system may provide output to the user or caregiver which also identifies a possible error condition, but still provides some substantive output.

Clinical uncertainty refers to the fact that different sensors might indicate seemingly contradictory conclusions. Clinical uncertainty is when one cannot be sure of the conclusion that is drawn from the data. For example, one of or the combined temperature sensor reading and/or accelerometers might indicate that the wearer is motionless, leading toward a conclusion of a resting user, the galvanic skin response sensor might provide a very high response, leading toward a conclusion of an active user, the heat flow sensor might indicate that the wearer is still dispersing substantial heat, leading toward a conclusion of an active user, and the heart rate sensor might indicate that the wearer has an elevated heart rate, leading toward a conclusion of an active user. An inferior system might simply try to vote among the sensors or use similarly unfounded methods to integrate the various readings. The present invention weights the important joint probabilities and determines the appropriate most likely conclusion, which might be, for this example, that the wearer is currently performing or has recently performed a low motion activity such as stationary biking.

According to a further aspect of the present invention, a sensor device may be used to automatically measure, record, store and/or report a parameter Y relating to the state of a person, preferably a state of the person that cannot be directly measured by the sensors. State parameter Y may be, for example and without limitation, body temperature, calories consumed, energy expenditure, sleep states, hydration levels, ketosis levels, shock, insulin levels, physical exhaustion and heat exhaustion, among others. The sensor device is able to observe a vector of raw signals consisting of the outputs of certain of the one or more sensors, which may include all of such sensors or a subset of such sensors. As described above, certain signals, referred to as channels, may be derived from the vector of raw sensor signals as well. A vector X of certain of these raw and/or derived channels, referred to herein as the raw and derived channels X, will change in some systematic way depending on or sensitive to the state, event and/or level of either the state parameter Y that is of interest or some indicator of Y, referred to as U, wherein there is a relationship between Y and U such that Y can be obtained from U. According to the present invention, a first algorithm or function f1 is created using the sensor device that takes as inputs the raw and derived channels X and gives an output that predicts and is conditionally dependent, expressed with the symbol $\pi$, on (i) either the state parameter Y or the indicator U, and (ii) some other state parameter(s) Z of the individual. This algorithm or function f1 may be expressed as follows:

$$f1(X) \pi\ U+Z$$

or $$f1(X) \pi\ Y+Z$$

According to the preferred embodiment, f1 is developed using the algorithm development process described elsewhere herein which uses data, specifically the raw and derived channels X, derived from the signals collected by the sensor device, the verifiable standard data relating to U or Y and Z contemporaneously measured using a method taken to be the correct answer, for example highly accurate medical grade lab equipment, and various machine learning techniques to generate the algorithms from the collected data. The algorithm or function f1 is created under conditions where the indicator U or state parameter Y, whichever the case may be, is present. As will be appreciated, the actual algorithm or function that is developed using this method will be highly dependent on the specifics of the sensor device used, such as the specific sensors and placement thereof and the overall structure and geometry of the sensor device. Thus, an algorithm developed with one sensor device will not work as well, if at all, on sensor devices that are not substantially structurally identical to the sensor device used to create the algorithm or at least can be translated from device to device or sensor to sensor with known conversion parameters.

Next, a second algorithm or function f2 is created using the sensor device that takes as inputs the raw and derived channels X and gives an output that predicts and is conditionally dependent on everything output by f1 except either Y or U, whichever the case may be, and is conditionally independent, indicated by the symbol $\perp$, of either Y or U, whichever the case may be. The idea is that certain of the raw and derived channels X from the one or more sensors make it possible to explain away or filter out changes in the raw and derived channels X coming from non-Y or non-U related events. This algorithm or function f2 may be expressed as follows:

$$f2(X) \pi\ Z \text{ and } (f2(X) \perp Y \text{ or } f2(X) \perp U$$

Preferably, f2, like f1, is developed using the algorithm development process referenced above. f2, however, is developed and validated under conditions where U or Y, whichever the case may be, is not present. Thus, the verifiably accurate data used to create f2 is data relating to Z only measured using highly accurate medical grade lab equipment.

Thus, according to this aspect of the invention, two functions will have been created, one of which, f1, is sensitive to U or Y, the other of which, f2, is insensitive to U or Y. As will be appreciated, there is a relationship between f1 and f2 that will yield either U or Y, whichever the case may be. In other words, there is a function f3 such that f3 (f1, f2)=U or f3 (f1, f2)=Y. For example, U or Y may be obtained by subtracting the data produced by the two functions (U=f1−f2 or Y=f1−f2). In the case where U, rather than Y, is determined from the relationship between f1 and f2, the next step involves obtaining Y from U based on the relationship between Y and U. For example, Y may be some fixed percentage of U such that Y can be obtained by dividing U by some factor.

One skilled in the art will appreciate that in the present invention, more than two such functions, e.g. (f1, f2, f3, ... f_n−1) could be combined by a last function f_n in the manner described above. In general, this aspect of the invention requires that a set of functions is combined whose outputs vary from one another in a way that is indicative of the parameter of interest. It will also be appreciated that conditional dependence or independence as used here will be defined to be approximate rather than precise.

The method just described may, for example, be used to automatically measure and/or report the body temperature of an infant, or the fact that a child is about to wet their bed or diapers while asleep at night, or caloric consumption or intake of a person using the sensor device, such as that person's daily caloric intake or any other data from Table 1.

Figure 26:
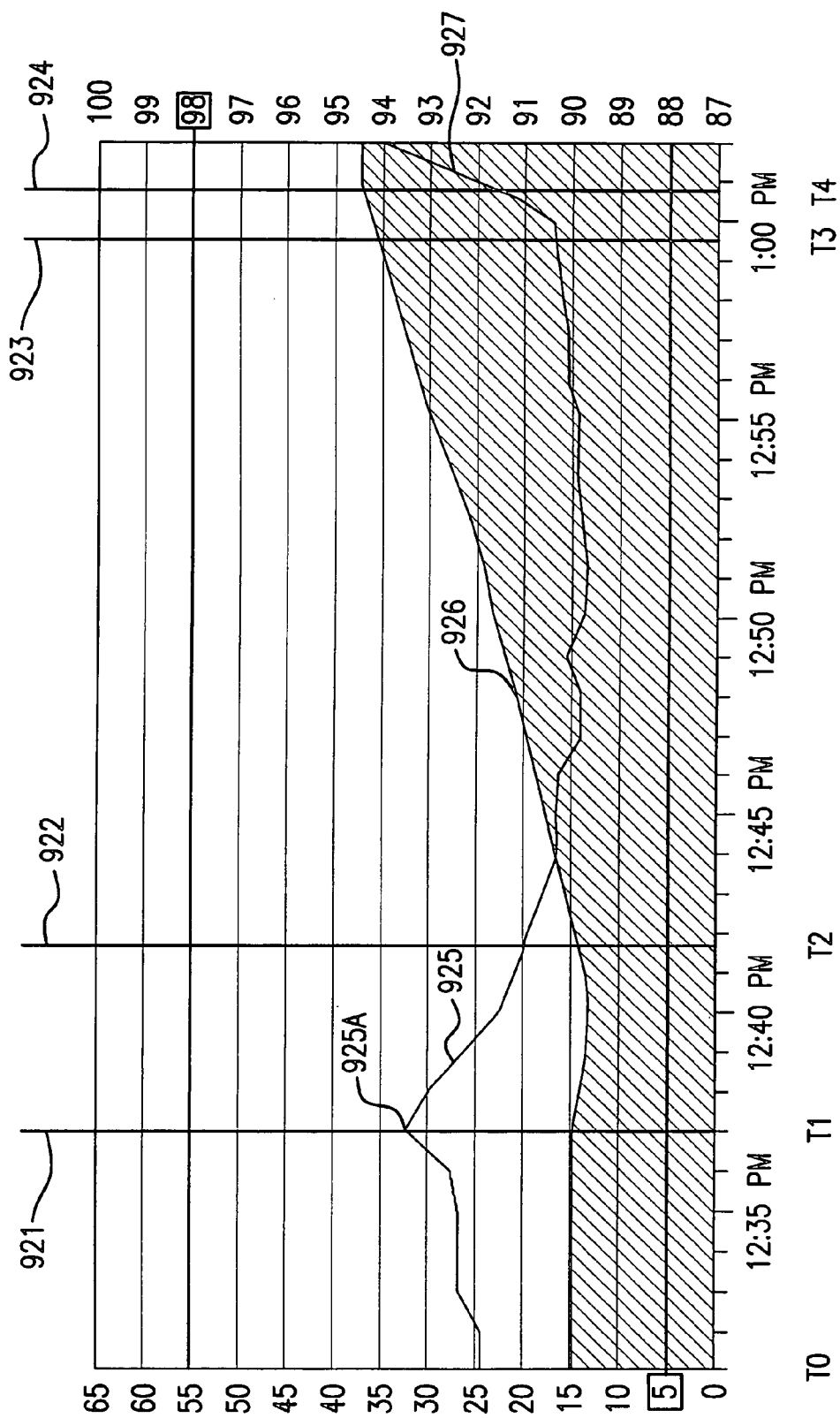
FIG. 26 is a graphical representation of output of the temperature measurement module.

Another specific instantiation where the present invention can be utilized relates to detecting when a person is fatigued. Such detection can either be performed in at least two ways. A first way involves accurately measuring parameters such as their caloric intake, hydration levels, sleep, stress, and energy expenditure levels using a sensor device and using the two function (f.sub.1 and f.sub.2) approach to provide an estimate of fatigue. A second way involves directly attempting to model fatigue using the direct derivational approach described in connection with FIG. 25. This example illustrates that complex algorithms that predict the wearer's physiologic state can themselves be used as inputs to other more complex algorithms. One potential application for such an embodiment of the present invention would be for first-responders (e.g. firefighters, police, soldiers) where the wearer is subject to extreme conditions and performance matters significantly. In a pilot study, the assignee of the present invention analyzed data from firefighters undergoing training exercises and determined that reasonable measures of heat stress were possible using combinations of calibrated sensor values. For example, if heat flux is too low for too long a period of time but skin temperature continues to rise, the wearer is likely to have a problem. It will be appreciated that algorithms can use both calibrated sensor values and complex derived algorithms. Referring now to FIG. 26, a graphical illustration represents a firefighter skin temperature during a training exercise in which a fire retardant suit having limited ventilation is worn. The area between times T0 and T1 indicates the baseline or normal readings for the device having a heat flux sensor, the output of which is identified as heat flux output 935, and a skin temperature sensor, the output of which is identified as skin temperature output 926. At time T1, indicated by line 921, the suit is donned. The effort expended in donning the suit is reflected by peak 925A of heat flux output 925, with a subsequent immediate drop in output 925 as the effects of the absence of ventilation within the suit is shown. Skin temperature output 926 shows little change until the beginning of the exercise at time T2, identified by line 922. While the heat flux output 925 continues to drop, skin temperature output 926 shows a consistent and linear rise in temperature through the end of the exercise at time T3 shown at line 923. The suit is removed at time T4, line 924. A sharp spike 927 in heat flux output is illustrated as the suit is removed. The outputs 925, 925 provide consistent data for which predictions may be made by extrapolated data points. Most importantly, given a known target for a parameter, for example skin temperature, a warning could be sounded prior to a catastrophic event, such as heat exhaustion or suffocation. The use of secondary data types, such as the heat flux output, serves to provide confirmation that differential events are or are not occurring. Referring back to FIG. 23, the reading from the axillary sensor indicates the localized nature of the temperature changes as seen in the femoral region and rules out differential events, such as the patient being immersed in water.

Additional functionality relating to this capability relates to the adaptation of the system to the detected condition. New patterns and data, once categorized, serve to improve predictability of similar or related events in the future. Upon remedying the situation, the predictive clock could be easily reset or newly adjusted, taking into account the identified event, but also evaluating the data for the time period prior to the event, creating new threshold identifiers for the event type.

Figure 27:
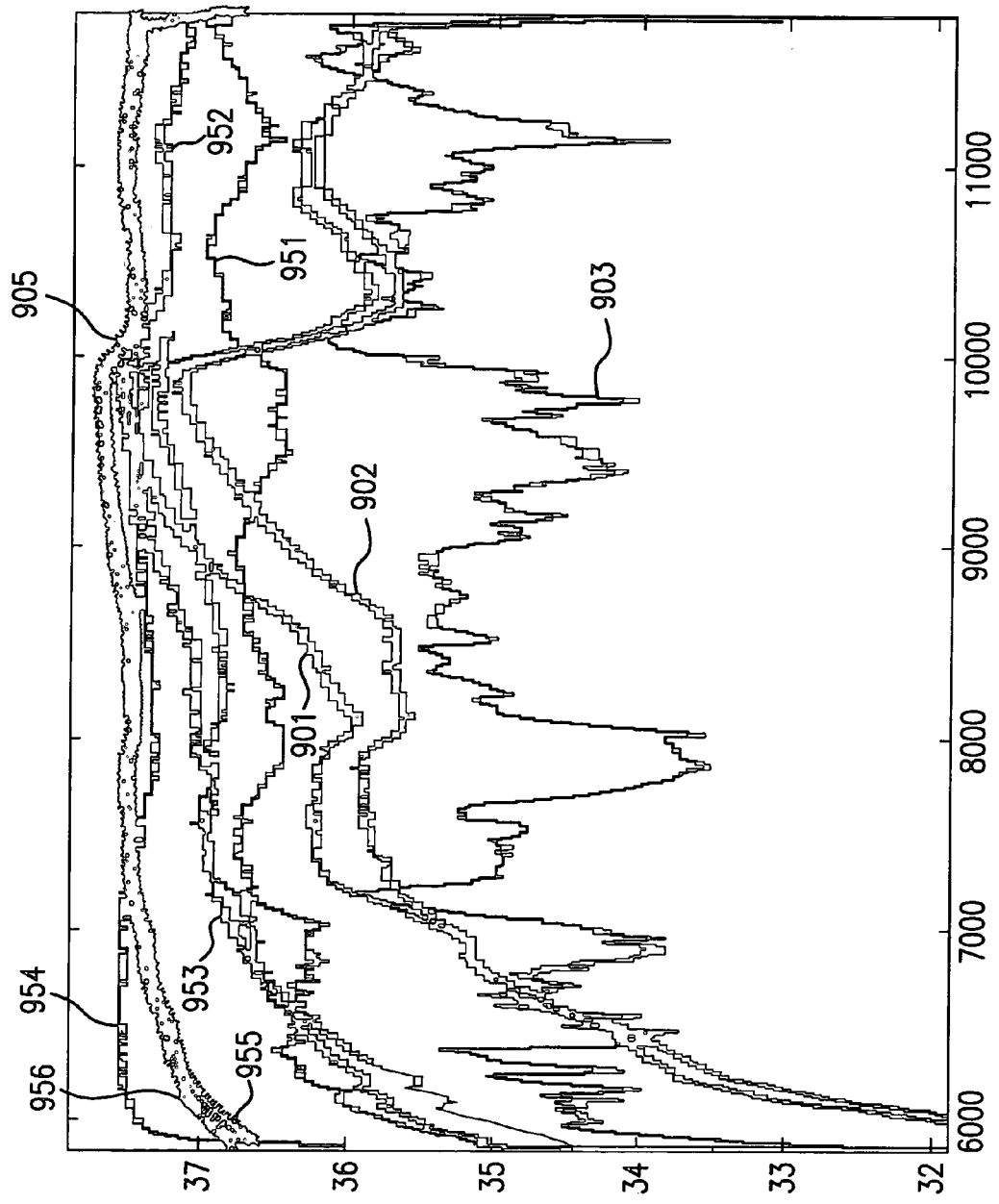
FIG. 27 is a graphical representation of output of the temperature measurement module.

Referring now to FIG. 27, the output of several sensors is illustrated, together with the data from output 1400 also presented for two modules. The data for FIG. 27, similar to that of FIG. 23, is drawn from left and right femoral sensors and an axillary sensor. Each sensor has a skin temperature output and an ambient temperature output, consistent with the description of FIG. 23. The axillary module is therefore supplying axillary ambient temperature output 903 and axillary skin temperature output 951. The left femoral module is supplying left femoral ambient temperature output 901 and left femoral skin temperature output 953. The right femoral module is supplying right femoral ambient temperature output 902 and right femoral skin temperature output 952. A rectal sensor is placed to provide a baseline core temperature reading to which each other measurement is correlated and is illustrated by rectal sensor output 954. The derived temperature output of each femoral module is illustrated as left femoral derived temperature output 956 and right femoral derived temperature output 955.

While certain rough correlations may be drawn from FIG. 27, it is apparent upon even a casual review that the various detected skin and ambient temperature bear little direct correlation to the measured rectal temperature. Axillary ambient temperature is particularly affected by body movement and activity, which forms the basis for the use of this output in many activity related contextual determinations, as will be described more fully herein. As with FIG. 23, a pronounced warm up period is indicated at the leftmost side of the graph. Additionally, peak 905 illustrates the insult more fully described with respect to FIG. 23. Left femoral derived temperature output 956 and right femoral derived temperature output 955, however, show close correlations to the measure rectal output 954, especially after the warm up period and recovery from the insult have occurred, as illustrated at the right most section of FIG. 27.

Figure 28B:
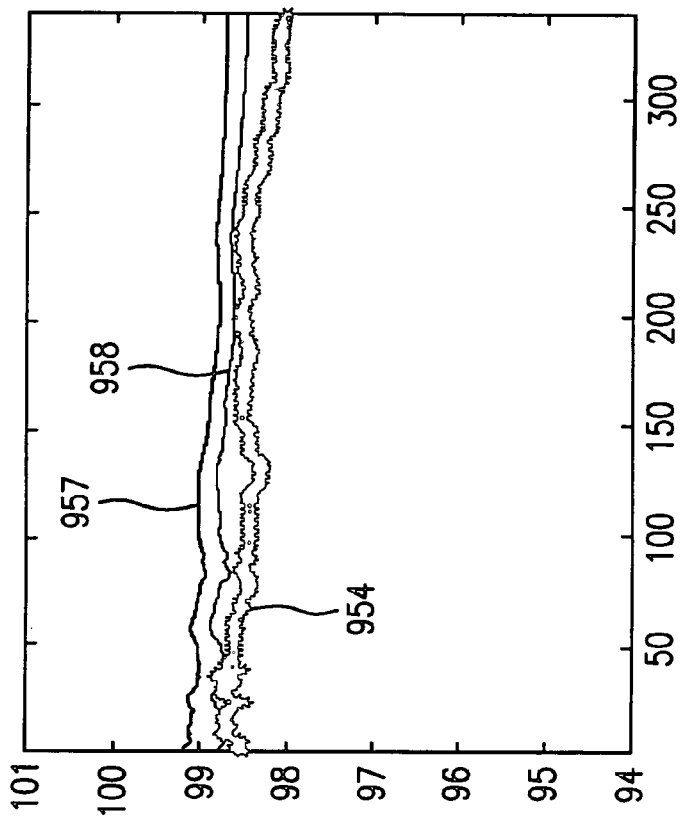
FIGS. 28A and 28B are graphical representations of output of the temperature measurement module.
Figure 28A:
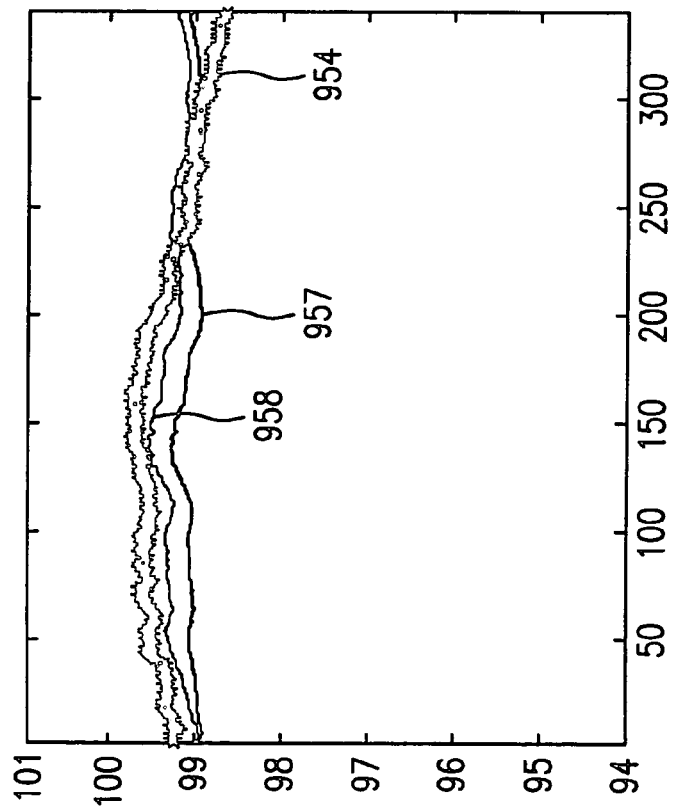

As previously described, the additional parameters may be added to increase the accuracy of derived temperatures. It is also possible that core body temperature may be predictable with no temperature measurements if an appropriate selection of other sensors are utilized, such as heart rate, galvanic skin response and motion. Additional parameters may be used to eliminate obviously compromised data as well as to assist in the selection of appropriate algorithms for contextual application. In many cases, however, additional parameters are incorporated into the derivation of the temperatures themselves as additional factors or coefficients. More specifically, referring now to FIG. 28, the effect of adding the additional parameter of body weight to the previously described derivations is illustrated. Rectal temperature data output 954 again provides a baseline for correlation of the derived measurements. Derived temperature output 957 may be taken from a single module or a combination of multiple modules. In either case, derived temperature output 957 is fairly consistent in tracking the actual rectal temperature within a mean error of better than 0.2 degrees Celsius and more preferably better than the 0.177 degrees Celsius shown in FIG. 28. Clinical or medical applications require an accuracy level having a mean error of better than 0.5 degrees Celsius. With the addition of the weight parameter in the derivation of the temperature, weight adjusted derived temperature output 958 is reflective of the actual rectal temperature output 954 within 0.155 degrees Celsius. These results generally result in a 10% improvement in derived temperature is solely attributable to the addition of this one parameter. FIG. 28 reflects a 16% improvement in accuracy.

Figure 29:
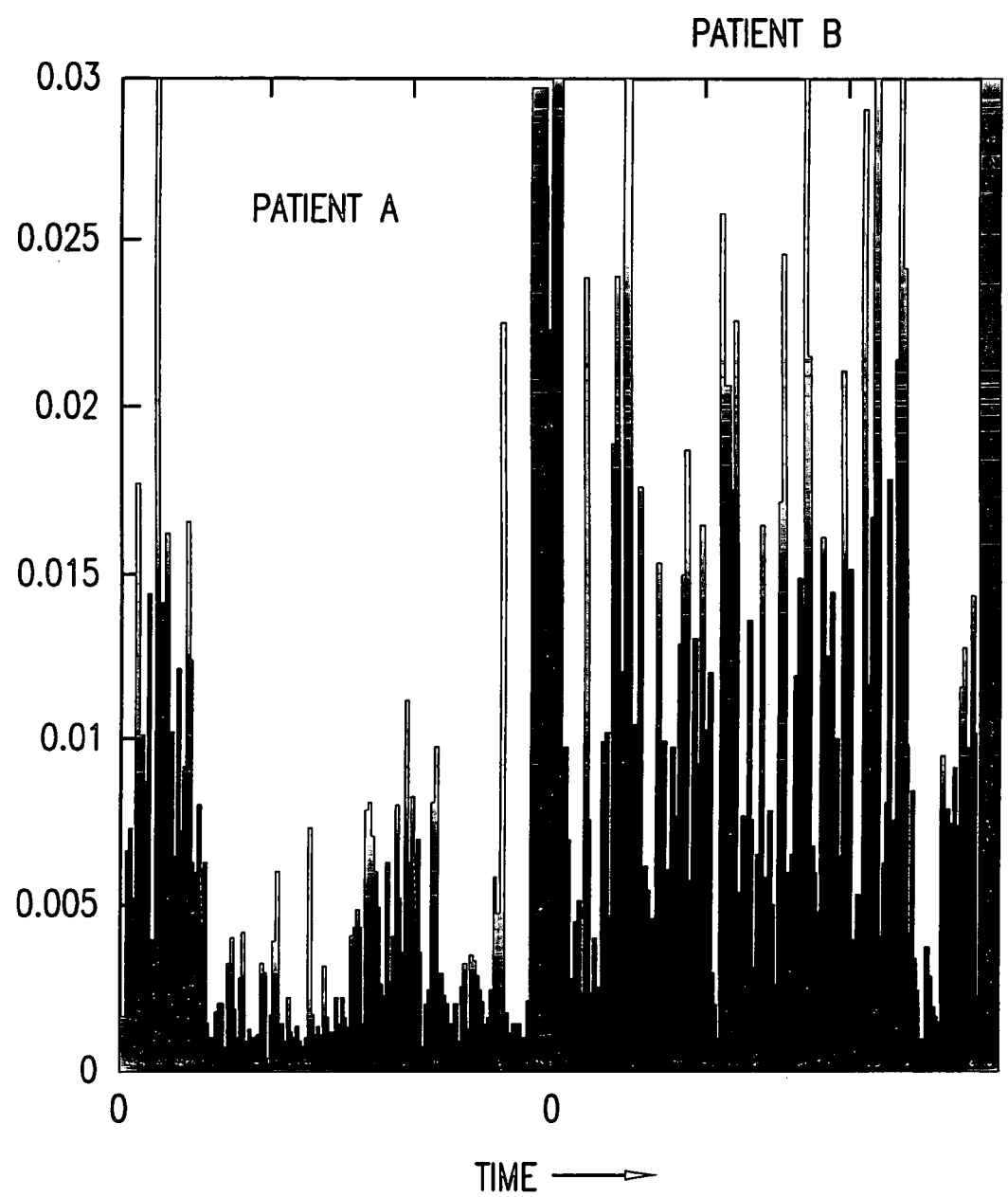
FIG. 29 is a graphical representation of output of the temperature measurement module.

FIG. 29 illustrates the use of an ambient temperature sensor as an activity detector. The graph shows output of the variance of an ambient temperature sensor one second intervals over five minute periods for Patient A on the left and Patient B on the right. Patient A was sedentary for the majority of the test period. Patient B was active. The graph of Patient B's periodic temperature readings over time indicate the heightened temperature sensed in the near body areas. This is also true of ambient temperature sensors which are not contained within a diaper or clothing. The number of peaks as well as their quantitative value provides good insight into the activity level of the patient. While not as quantitatively accurate as an accelerometer, qualitatively the ambient temperature sensor provides a significant amount of data relating to the relative movement of the wearer's body, which can be useful for a number of derivations as will be described more fully herein. It should be specifically noted that one embodiment of the device may monitor only ambient temperature in order to provide basic activity data of the wearer.

Figure 30:
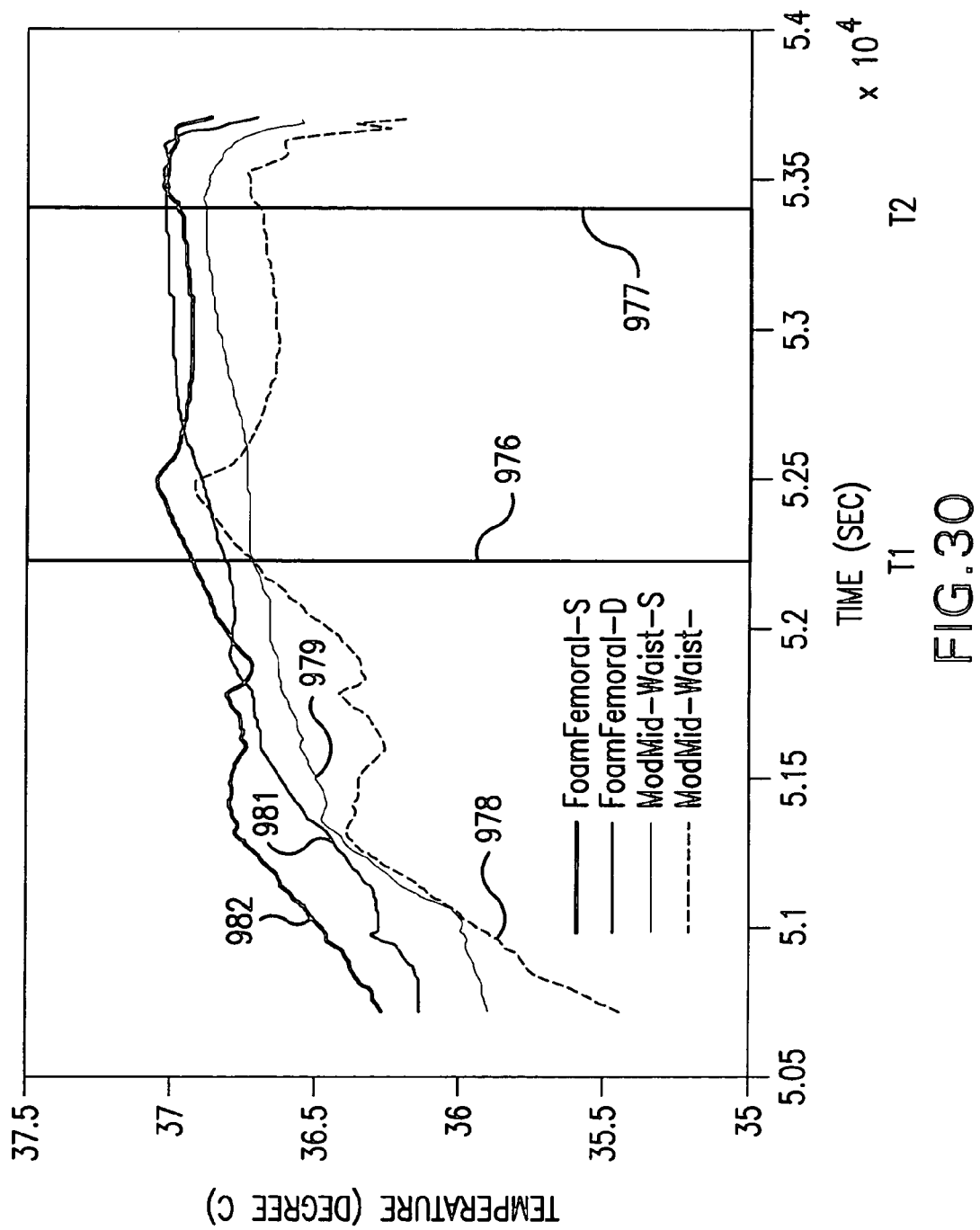
FIG. 30 is a graphical representation of output of the temperature measurement module.
Figure 31:
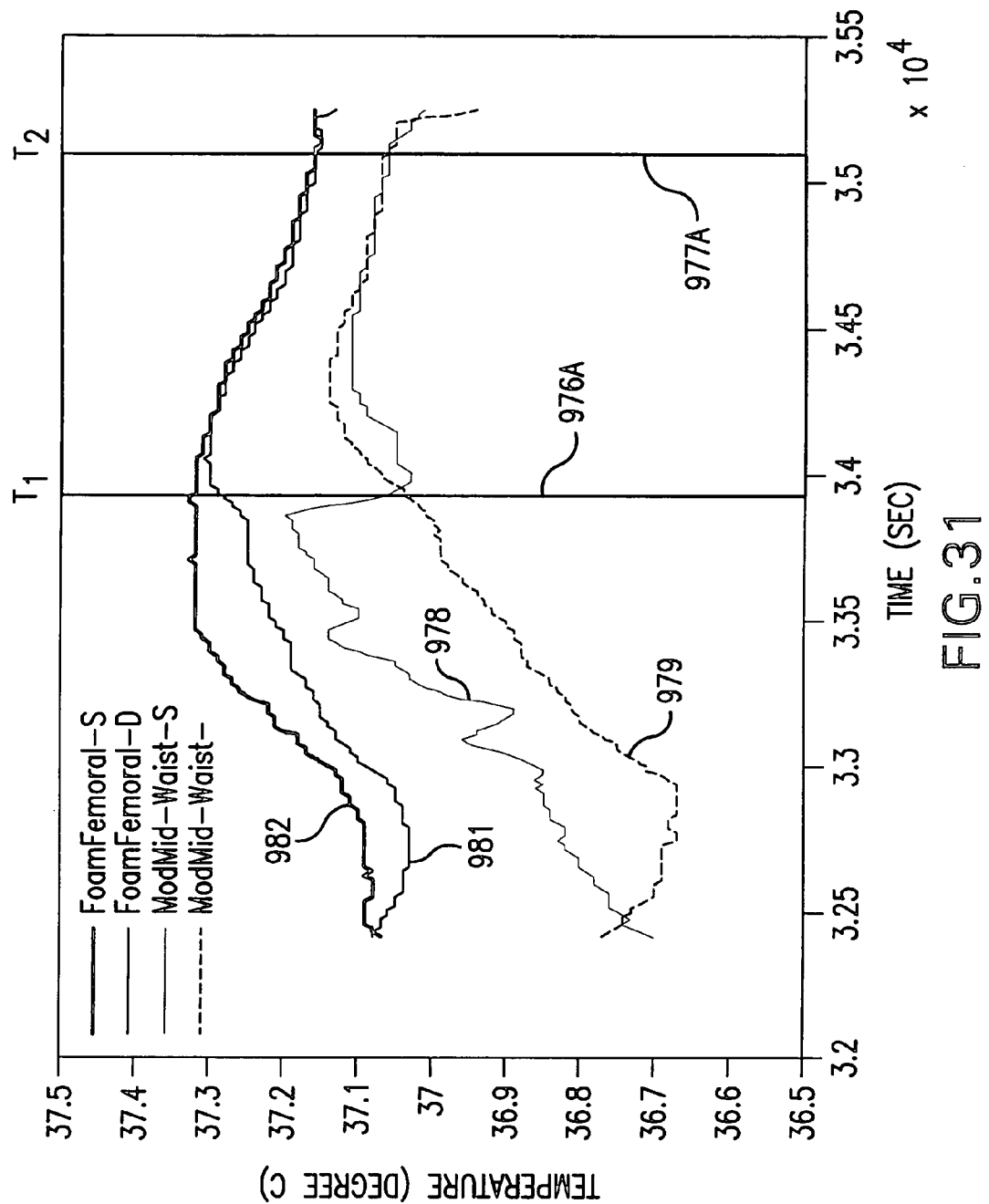
FIG. 31 is a graphical representation of output of the temperature measurement module.

FIGS. 30 and 31 also illustrate additional types of information regarding context and activity level which can be derived from the use of the temperature module and the associated processing. The figures both illustrate the output of two modules, one being placed in the femoral region and one at the waist area. In this particular instance, the locations are not relevant to the determination. Femoral skin temperature output 981, femoral ambient temperature output 979, waist skin temperature output 982 and waist ambient temperature output 978 are graphed against time. Each shows a relative period of interest from time T1 to time T2. In FIG. 30, times T1 and T2, demarcated by lines 976, 977, respectively, indicate a period of sleep for an infant patient while being held by its mother. FIG. 31 indicates a similar time period demarcated by lines 976A, 977A, during which the infant was asleep in a car seat. It is important to note both the consistency of data from all four sensors during the period of sleep, as well as the distinct differences between the graph characteristics. The sleeping child in FIG. 31 has a slowly dropping temperature, consistent with general, unencumbered sleep. The child held while sleeping in FIG. 30, however, maintains a relatively flat temperature profile during this time period. It is therefore possible to determine whether an infant is being held, and for what time periods. Additionally, periods of sleep may be detected and recorded.

The device is also able to detect appropriate data to derive the proximity of other humans to the patient as mentioned above. However, other methods may be employed to detect the presence of bodies near the sensor. Proximity detection currently involves either: (i) detecting the presence of a preselected device with a matched detector or (ii) using external equipment such as a video camera or motion sensor. There is currently no way to conveniently know when a person gets close to an object. What is disclosed herein is intended to detect the motion of an object that can hold a significant static charge within a few feet of the sensor. It is further known that, because this detection is based upon a magnetic field, the relationship between the signal strength or detected charge and distance is correlated to strength=$1/distance^2$. The human body, as it is made mostly of water, has this property in a way that most solid inanimate objects, such as a chair, do not. In principle a cat or dog moving by such a sensor could be mistaken for a person but because those animals hold much less charge than even a child, they would have to be much closer to register the same effect on the sensor.

A proximity detector of this type utilizes an R/C oscillator constructed around the ambient capacitance of a copper plate. As the environment surrounding the plate changes, such as mounting the device on the human body or moving other objects closer/farther from the device armband, the capacitance of the plate changed leading to a change in the frequency of the oscillator. The output of the oscillator is then input into a counter/timer of a processor. Another embodiment utilizes a short antenna tied to the input of a FET transistor with very high gate input impedance. Very slight changes in the environment surrounding the antenna caused very detectable changes in the output of the FET amplifier. When the circuit is moved through the air toward other objects and when objects are moved closer to the antenna, changes in output were detected. The charge reflecting the motion is believed to be static in nature.

In addition to capacitance and other techniques described above, other sensors may be utilized to provide or enhance this type of proximity detection, including galvanic skin response, heat flux, sound and motion to help recognize these context points with greater confidence, accuracy and reliability.

A proximity detector, as described above, may have many applications. These include the use of the device to interact with a computer so that the screen saver, instead of being time-based after the last time you hit a key, turns on as soon as you walk away and comes back to the normal screen as soon as you sit down, without needing to initiate contact. The backlighting for remote controls, light switches, phones, or other items used in the dark may be activated when a body is present, together with the lights or devices controlled thereby. A child-proof gate may be designed such that it is unlocked or even swung open when an adult is present but not when a child is alone nearby. A cell phone or other communication device might be aware if the user is carrying it on his or her person or has it nearby, such as on a night stand. The device might be programmed with two different modes in the two situations to save power, download emails or the like, as appropriate.

Safety-related implementations may include the ability to know if a person has approached or opened a liquor, gun or money cabinet, or the detection of people near a hazardous site or situation, including a pool or beach, when no supervision is present. A device embedded in a key fob or other device might provide the ability to detect whether a person is approaching in a dark parking lot or around a corner of a building. With respect to automobiles, the device may detect whether an adult or child is in the driver's seat and disable the ignition.

A number of entertainment related embodiments are also contemplated. A video game may be provided when a player is running towards the screen to zoom in but as the player runs away from the screen it zooms back to normal view or even further out. Similarly, in a non-video game, if two players are playing with a ball, and as the ball comes closer to them, it glows more brightly, but as it is thrown away from them it grows dimmer until it reaches another person. This system may also detect the approach of an adult, which triggers the ball to discontinue the effect. Expanding the concept to the colorful ball pits in shared playlands, where as the child crawls and jumps through them, the mass of balls directly by them are glowing, while the ones to the other side of the pit are glowing for another child or dark because there is no child there. Lastly, a video wall may be provided which displays a shadow of a stylized image of the user. If the user moves his or her hand closer to the wall, that area about the size of the hand becomes darker in that vicinity but may also become a virtual pointer or paint dispenser can to draw on this wall. This easily extends to making water fountains responsive to children playing in them by manipulating and controlling the water jets to chase a child or create a pattern around the child's proximity. Conversely, the system could stop the specific jet that the child is standing above, making the child the chaser of the water jets. Again, this could be a special child-only effect which discontinues near adults.

Figure 32:
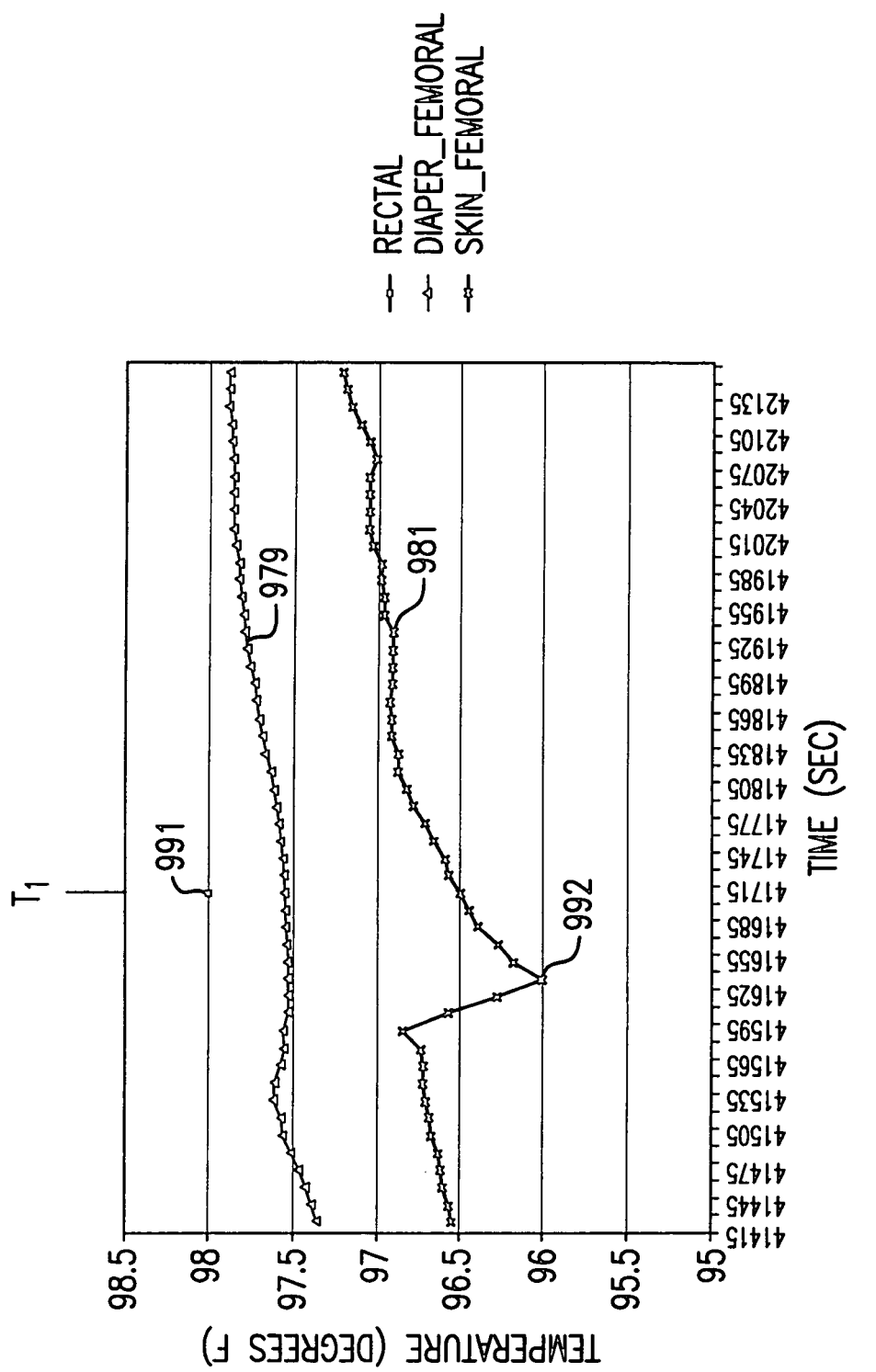
FIG. 32 is a graphical representation of output of the temperature measurement module.

FIG. 32 illustrates another distinct illustration for detection of a particular event or activity. A single femoral module is utilized, producing femoral skin temperature output 979 and femoral ambient temperature output 981. In this illustration, the patient's diaper was removed for collecting the rectal data point 991 at time point T1. A characteristic trough 992 immediately preceding time point T1 in femoral ambient temperature output 981 without corresponding changes in femoral skin temperature sensor output 979 indicates the sudden change in ambient conditions without change in skin temperature. This pattern is identifiable and repeatable and may be detected reliably once the system learns to observe the relevant parameters.

Figure 33:
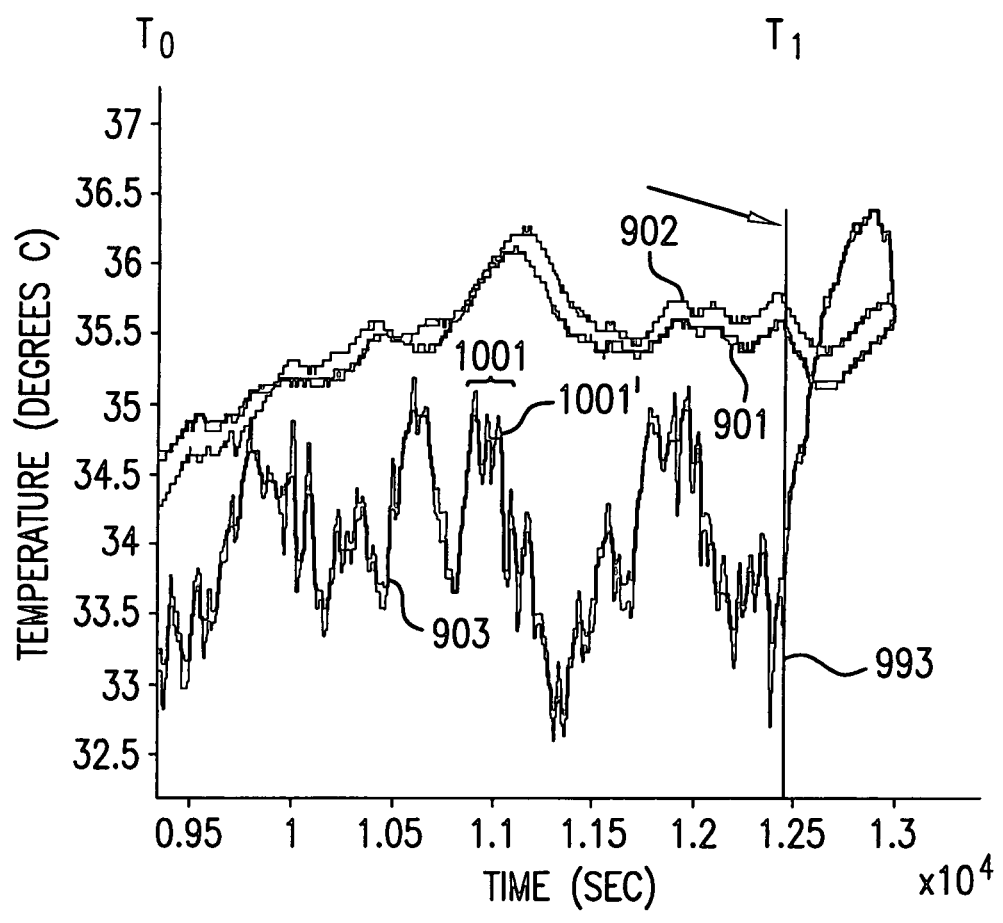
FIG. 33 is a graphical representation of output of the temperature measurement module.

Similarly, FIG. 33 illustrates the determination between resting and activity. Consistent with the findings associated with FIGS. 27 and 29, activity can be monitored through the use of the ambient temperature sensors. In this instance, consistent with FIG. 27, three modules were applied to the patient, being left and right femoral and axillary. Outputs include left femoral ambient temperature output 901, right femoral ambient temperature output 902 and axillary ambient temperature output 903. During the time period from time T0 to time T1, indicated at line 993, the patent was active, as is characterized by the generally random and periodic changes in ambient temperature, as well as the small intermediate peaks of the larger features. These are exemplified by peak 1001 which further comprises a series of intermediate peaks 1001'. At time T1, the patient became sedentary while reading. Instantaneous changes in both the qualitative value and waveform characteristics are noted in the time period immediately subsequent to time T1 in the axillary ambient temperature output 903. While some changes are evident in the femoral outputs during this same time period, when viewed in the light of the entire graph for the femoral outputs, the changes are indistinct and unremarkable. What is notable, however, is the ability to detect periods of activity and rest, together with the interface of the two at a particular and identifiable moment in time. The activity monitor may also detect the wearer falling and sound an alarm or warning to a parent or caregiver.

While the activity monitoring functions of the device, as described more fully herein, are useful for a number of applications, they are not entirely accurate. The device can, however, accurately determine and recognize sleep and sedentary situations because the sensors are steady and are tracking close together. A monitor might therefore be provided that reports how much the user was active during a given period by subtracting inactivity from total time. An accelerometer may be added to more accurately measure physical activity. The temperature sensor, however, improves the ability to filter out contexts like motoring, which create inaccuracies in accelerometer-based detectors, including pedometers and energy expenditure monitors.

Some important applications for the various detection capabilities described above are: (i) monitoring of infants and children in day care or other extended non-parental supervision and (ii) the increasingly important monitoring of elderly patients under institutional or other nursing care. In both cases, significant opportunities arise for both abuse and neglect of the people under care. Additionally, the families and/or parents of these individuals have a constant concern regarding their ability to both monitor and evaluate the care being provided, especially when they are not physically present to observe or enforce appropriate care. The system described herein may be well utilized to place a reliable and tamper resistant watch on the patient, while the observer may track progress and care from a remote location with as simple a device as a baby-monitor style receiver, or any computing device connected to an appropriate network for receiving the output of the device according to the broader teachings of Teller, et al., copending U.S. patent application Ser. Nos. 09/595,660 and 09/923,181. Extrapolations of the data and derived information presented herein include the ability to determine the nature and frequency of urination and bowel movement events, corresponding diaper changes, teething pain, periods of close interaction with other humans, times being held, sleep time, cumulative lack of sleep, activity time, repositioning for bedridden patients, shaking or other physical abuse, overheating and the like. The device may also be provided with the ability to recognize feeding patterns and predict/alert a caregiver that it is time for the next feeding. This can be accomplished through the use of the activity monitoring abilities of the device to make a rough calculation of energy expended or merely recognizing a timing pattern.

The device may further be provided with a unique identification tag, which may also be detectable through wireless or other proximity related transmission such that each module can detect and record which other modules have come within a certain perimeter. This may have applications in military, institutional and educational settings, where it is useful to know, not only where people are, but with whom they have come into contact. This may also be useful in a bio- or chemical terrorism attack. Moreover, in the child care setting described above, it may be useful for a parent or caregiver to assess the level and type of social contact of each child.

With respect to infants and other non-communicative children and adults, the device may be utilized to determine environmental temperature comfort level. This may be related to determining whether the wearer is too hot or too cold in a particular room or whether the clothing being worn is too heavy or too light. Similar to the bathroom training example above, a learning period may be necessary to determine the particular comfort zone of each wearer as well as any ancillary physiological or emotional responses detected during and prior as well as subsequent to the individual getting to such a state. Additionally, certain generalized comfort temperature zones may be provided with the device for use prior to or in lieu of personalization. At its most extreme, the device may also detect hypo- and hyperthermia, shivering or a rise in body or skin temperature to levels of concern as referenced with respect to the firefighter example, above.

In many situations, including new parents, new caregivers or changes in care responsibilities, infants may be placed in situations with inexperienced supervision. Crying, in infants, is a primary means of communication. Unfortunately, there are many reasons why infants are crying and inexperienced caregivers are frequently at a loss to diagnose the problems. The device may be adapted to determine, through detection, derivation of data and/or process of elimination, why an infant is crying. While this is particularly useful for infants, it is also clearly applicable to non-communicative adults and the elderly.

The system may determine that the wearer has a fever through the use of temperature sensing. It may determine that the diaper is soiled in the same manner. Temperature sensing, as described above, may also provide information as to whether the wearer is too hot or too cold. A number of determinations may also be made based on patterns of behavior. Infants especially eat on a regular schedule and the timing of feedings may be detected and/or derived and reported. Additionally, these events may be predicted based on the patterns detected, as presented with respect to ovulation, bed wetting and the like. Hunger may also be detected through the use of microphones or other audio detectors for bowel and stomach sounds. Finally, lack of sleep is another pattern-based behavior that may be predicted or detected, especially when additional parameters related to or affected by lack of sleep are detected, recognized or derived, such as changes in immune response, alertness and social skills.

The system may be provided with the ability to create reports of each wearer's daily routine. While this may be most useful to a parent or caregiver to assess what has happened to the wearer over a past period of time, it may also be used as a predictor of scheduled or pattern behavior. This may be most useful for a new caregiver or baby sitter, for example, to be presented with a map of the supervised time period which includes most expected events or behaviors.

In tracking consistent or pattern activities over time, changes in patterns or physiological parameters may be detected. This is especially true of small changes which occur over long periods of time. This may aid in the detection or diagnosis of certain diseases or conditions. It may also be useful in creating correlations between detected physiological parameters, contexts, derived parameters and combinations of the above. For example, it may be come apparent after some period of time that high quality sleep is correlated to significant exercise within a preceding 6 hour period of time. Additionally, it may become apparent that more significant weight loss is highly correlated to better sleep patterns.

As infants grow and mature, changes occur in the patterns and values of temperature changes within the body. Infants with poorly developed temperature regulatory systems exhibit sharp swings and spikes in their temperature profile. As the body matures, as well as grows and adds fat, these temperature swings become less severe. The system may then provide an assessment of development based upon continued recording of these temperature fluctuations over time.

In many situations, such as administration of medication, physical therapy or activity limitations in pregnant women, compliance with a proper routine over time is essential. In many cases, even the individual is unable to assess the qualitative nature of their own compliance with a prescribed routine or program. In other cases, a medical professional or caregiver must assess and monitor the level of compliance of a patient. The system provides the ability to make these assessments without significant interference and with confidence in the results. In this situation, an insurance company or employer may use the system to collect and/or produce reports to the extent to which a wearer is following a program or reaching certain goals. These reports may then be transmitted for analysis to the insurance company or employer.

Many of the features and functionality described herein are based on the detection of certain parameters; the derivation of certain contexts, parameters or outcomes and the appropriate identification of certain events and contexts. The ability of the system to accurately make these determinations is proportional to the sample size and knowledge base. This is applicable both in terms of the detection of a particular event by the nature and interaction of the detected signals, such as a urination insult, but also in the development of more accurate algorithms which make the determinations. The system is specifically adapted to communicate with a larger system, more specifically a system according to Teller, copending U.S. patent application Ser. No. 09/595,660. This system may include the collection of aggregate data from a number of wearers, together with the correlated data and derivations, in order to more accurately recognize the signals which precede identified events. Modifications in the system processing and/or algorithms may then be retransmitted to the user's systems and modules as an update.

Figure 34:
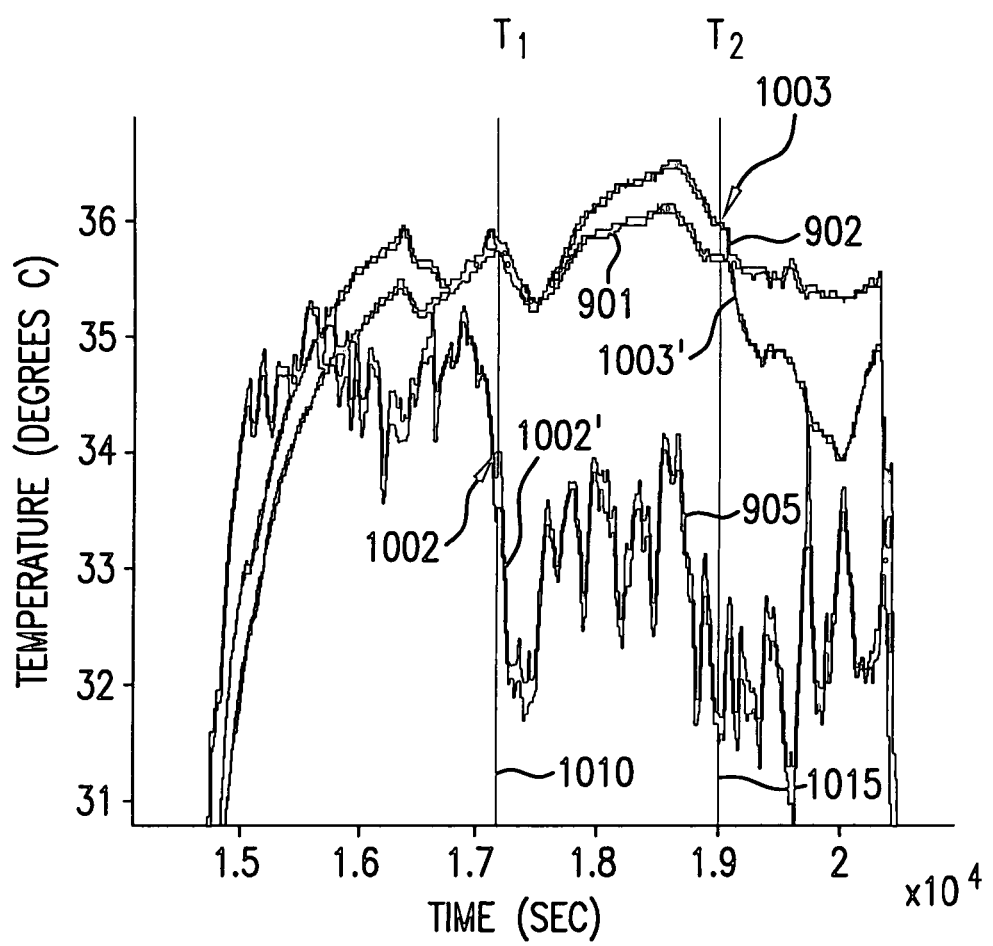
FIG. 34 is a graphical representation of output of the temperature measurement module.

Two other important aspects of any monitoring device must be addressed: detecting the failure of the unit and preventing external factors from upsetting the system. With respect to dislodgement of the module from its appropriate mounting position, FIG. 34 illustrates the easily detectable patterns and data associated with this event. As with FIG. 33, three modules were applied to the patient, being left and right femoral and axillary. Outputs include left femoral ambient temperature output 901, right femoral ambient temperature output 902 and axillary ambient temperature output 903. At time point T1, identified by line 1010, the axillary sensor became dislodged at peak 1002. Trough 1002' is instantly created in the data record. At time point T2, identified by line 1015, the right femoral sensor became dislodged at peak 1003 and trough 1003' is created in the data. It should be noted that the shape of waveform 1003' is more typical of dislodgement wave patterns. These sudden changes in temperature, coupled with no corresponding change in other sensors, such as left femoral ambient temperature output 901 during either event, reliably and consistently identifies this failure and provides the ability to notify a caregiver to remedy the situation.

An additional functionality of the device is the ability to utilize sensed parameters, derived parameters and contexts to control other devices. For example, if the system senses that the user is too cold, it can generate a signal to a thermostat to raise the temperature of the room in which the user is located. Moreover, the system can detect sleep states and prevent phones from ringing or turn the lights or television off during such periods. The device may, through the temperature sensing and motion detection functionalities described above, also be utilized as a pointing device for interaction with a computer or video game system. The system may also be utilized, similar to the video game, for detection of emotional or physiological states utilizing signals or methods known in the field of biofeedback, or for detection of gestures by the wearer and use biofeedback or those detected gestures to control another device. Gestures can include particularized motions of limb, limbs and/or full body. Devices controlled include stage lighting, projectors, music and dance club floors with interactive lighting. Music devices may include stage-based devices as well as group or personal MP3 players.

Although particular embodiments of the present invention have been illustrated in the accompanying drawings and described in the foregoing detailed description, it is to be further understood that the present invention is not to be limited to just the embodiments disclosed, but that they are capable of numerous rearrangements, modifications and substitutions, as identified in the following claims.

What is claimed is:

1. An apparatus for monitoring human status parameters, comprising:
a housing having a skin interface surface for creating an insulated interface with a wearer's skin;
a skin temperature sensor that generates data indicative of a skin temperature of the wearer, said skin temperature sensor mounted within said housing and in thermal communication with said insulated interface;
a temperature sensor mounted on a side of the housing away from the wearer's skin that generates data indicative of a temperature condition within a garment of the wearer, said garment surrounding said housing; and
a processor in electronic communication with said sensors for receiving said data indicative of the skin temperature of the wearer and said temperature condition within the garment and for generating a derived temperature-based parameter of the wearer.

2. The apparatus as described in claim 1, wherein said housing is further comprised of a convex skin interface surface.

3. The apparatus as described in claim 1, wherein said housing is further comprises a concave garment-facing surface.

4. The apparatus as described in claim 1, wherein said skin interface surface has a convex protrusion along a longitudinal axis.

5. The apparatus as described in claim 1, wherein said temperature sensors further comprise at least one thermistor.

6. The apparatus as described in claim 1 further comprising a heat flux sensor.

7. The apparatus as described in claim 6, wherein said housing further comprises an orifice extending from said skin interface surface to an ambient surface adjacent said heat flux sensor.

8. The apparatus as described in claim 1 further comprising an adhesive material for affixing said housing on the wearer's skin.

9. The apparatus as described in claim 8, wherein said adhesive material further comprises at least one sensor.

10. The apparatus as described in claim 9, wherein said adhesive further comprises at least one electrical contact for electronic communication with said processor.

11. The apparatus as described in claim 1, wherein the temperature sensor is mounted on a side of the housing away from the skin interface surface.

12. The apparatus as described in claim 1, wherein said garment is a diaper.

13. The apparatus as described in claim 1 further comprising at least one of: a motion sensor and a heart rate sensor.

14. The apparatus as described in claim 1 further comprising a sensor mounted remotely on a body of the wearer in electronic communication with said processor.

15. The apparatus as described in claim 1, wherein said derived temperature-based parameter is a core temperature of the wearer.

16. The apparatus as described in claim 1, wherein said derived temperature-based parameter is an event.

17. The apparatus as described in claim 16, wherein said event is one of: urination and defecation.

18. The apparatus as described in claim 16, wherein said processor recognizes a signal prior in time to said event which is related to said event.

19. The apparatus as described in claim 18, wherein said processor causes a notification to be generated upon recognition of said signal.

20. The apparatus as described in claim 16, wherein said processor causes a notification to be generated upon occurrence of the event.

21. The apparatus as described in claim 1, wherein said derived temperature-based parameter is a physiological parameter.

22. The apparatus as described in claim 21, wherein said processor recognizes a signal prior in time to initiation of said physiological parameter.

23. The apparatus as described in claim 22, wherein said processor causes a notification to be generated upon recognition of said signal.

24. The apparatus as described in claim 21, wherein said processor causes a notification to be generated prior to or upon initiation of said physiological parameter.

25. The apparatus as described in claim 21, wherein said physiological parameter is selected from the group consisting of heart beat and energy expenditure.

26. The apparatus as described in claim 1, wherein said derived temperature-based parameter is an activity.

27. The apparatus as described in claim 26, wherein said processor recognizes a signal prior in time to initiation of said activity.

28. The apparatus as described in claim 27, wherein said processor causes a notification to be generated upon recognition of said signal.

29. The apparatus as described in claim 26, wherein said processor causes a notification to be generated upon initiation of said activity.

30. The apparatus as described in claim 26, wherein said processor causes a notification to be generated prior to initiation of said activity.

31. The apparatus as described in claim 1, wherein each of said sensors further comprises an array of sensors.

32. The apparatus as described in claim 1 further comprising input means for said wearer to input one of an additional physiological and additional demographic information, said additional information comprising input to the generation of said derived temperature-based parameter.

33. The apparatus as described in claim 32, wherein said temperature-based parameter is at least one of core temperature, body state, and activity.

34. The apparatus as described in claim 1, wherein said housing is mounted on a femoral region of said wearer.

35. The apparatus as described in claim 1, wherein said housing is mounted to at least one of: an inguinal area of said wearer, an axillary area under an arm of said wearer, an upper arm of said wearer, an inside of a thigh of said wearer, a groin area of said wearer, an area behind an ear of said wearer, a forehead of said wearer, a sole of a foot of said wearer, a palm of said wearer, a finger of said wearer, a wrist of said wearer, an area between a corner of an eye and a side of a nose of said wearer, a chest of said wearer, and an area along a spine of said wearer.

36. The apparatus as described in claim 1, wherein said housing exerts pressure on the wearer's skin.

37. The apparatus as described in claim 1, wherein said derived temperature-based parameter is utilized to predict one of: ovulation, menstruation and hot flashes.

38. The apparatus as described in claim 1, wherein said derived temperature-based parameter is utilized to detect dislodgement of the housing from the body of said wearer.

39. The apparatus as described in claim 1, wherein at least a portion of said apparatus is disposable.

40. The apparatus as described in claim 1, wherein the entire apparatus is disposable.

41. The apparatus as described in claim 1, wherein said apparatus is affixed to one of: a diaper and an article of clothing.

42. An apparatus for monitoring human status parameters, comprising:
   a module housing having a skin interface surface;
   a skin temperature sensor that generates data indicative of a skin temperature of a wearer, said skin temperature sensor mounted within said housing and in thermal communication with said skin of said wearer;
   a temperature sensor that generates data indicative of a temperature condition within a garment;
   a first processor in electronic communication with said sensors for (i) receiving at least a portion of said data indicative of the skin temperature of the wearer and said temperature condition within the garment and (ii) transmitting at least a portion of said data indicative of said temperatures of said wearer to a receiver unit; and
   a receiver unit having:
      a receiver for receiving said transmitted data indicative of said temperatures of said wearer;
      a second processor for generating a derived temperature-based parameter of said wearer; and
      data output means for communication of said derived temperature-based parameter of said wearer, wherein said data output means provides an indication of a status of at least one of: an event, an activity, and a body state.

43. The apparatus as described in claim 42, wherein said receiver and said module are adapted to be affixed to each other.

44. The apparatus as described in claim 42, wherein said data output means is at least one of: a visual display, an audio speaker, a tactile signal generator, a haptic signal generator and a Braille display.

45. The apparatus as described in claim 42, wherein said receiver means further comprises an additional temperature sensor.

46. The apparatus as described in claim 42, further comprising a heat flux detector.

47. The apparatus as described in claim 42, wherein said indication comprises a prediction of at least one of an impending event, activity and body state.

48. The apparatus as described in claim 42, wherein said module and said receiver unit are capable of communication with only one another.

49. A system for monitoring human status parameters, comprising:
   a housing comprising an insulated interface for a wearer's skin;

a skin temperature sensor mounted on said housing that generates data indicative of the wearer's skin temperature at said insulated interface;

a temperature sensor mounted on a side of the housing away from the wearer's skin that generates data indicative of a temperature within a diaper of the wearer surrounding the housing; and a processor in electronic communication with said sensors for receiving at a least a portion of said data indicative of the skin temperature of the wearer and said temperature in said diaper and for generating a status parameter of the wearer.

50. The system according to claim 49 further comprising a heart rate monitor mounted in the housing.

51. The system according to claim 49, wherein the status parameter is selected from the group consisting of a removal of the diaper, an activity period, a rest period, urination or defecation in the diaper, and dislodgement of the housing.

52. The system according to claim 50, wherein said processor is located in said housing.

53. The system according to claim 49, wherein said status parameter comprises a core body temperature.

54. The system according to claim 53, wherein the core body temperature is derived with an equation comprising a backward average of a temperature difference between the skin temperature and the temperature in the diaper.

55. The system according to claim 53, wherein the core body temperature is derived with an equation comprising a backward average of a temperature difference between the skin temperature and the temperature in the diaper and also comprising an average squared difference between the skin temperature and the temperature in the diaper.

56. The system according to claim 53, wherein said status parameter is derived using contextual information.

57. The system according to claim 49, wherein said processor is operable to generate a status parameter according to an algorithm, wherein said algorithm is modified by changes to said data indicative of skin temperature at said insulated interface and said data indicative of a temperature condition within an enclosed space.

58. The apparatus according to claim 1 further comprising a sensor for sensing heart related parameters.

59. The apparatus according to claim 42 further comprising a sensor for generating data indicative of heart related parameters.

60. The system according to claim 53, wherein the status parameter is derived using data from a heat flux detector.

61. The system according to claim 49 further comprising a sensor for generating data indicative of heart related parameters.

62. The system according to claim 49, wherein said status parameter is at least one of an event, an activity, or a body state.

63. The system according to claim 62, wherein said event is one of: urination and defecation.

64. The system according to claim 62, wherein said processor recognizes a signal prior in time to said event, said signal being related to said event.

65. The system according to claim 62, wherein said processor recognizes a signal prior in time to said activity, said signal being related to said activity.

66. The system according to claim 62, wherein said processor recognizes a signal prior in time to initiation of said body state, said signal being related to said state.

67. The system according to any one of claims 64-66, wherein said processor causes a notification to be generated upon recognition of said signal.

68. The system according to claim 62, wherein said processor generates a signal upon initiation of said at least one of said event, said activity and said body state.

69. The system according to claim 62, wherein said processor generates a signal prior to initiation of said at least one of said event, said activity and said body state.

70. The system according to claim 49, wherein said insulated interface is created by pressing said skin temperature sensor against the wearer's skin.

71. The apparatus according to any one of claims 1 and 42 further comprising a sensor for generating data indicative of a galvanic skin response sensor of the wearer.

72. The apparatus according to any one of claims 1 and 42 further comprising a sound sensor.

73. The system according to claim 49 further comprising a sensor for generating data indicative of a body potential of the wearer.

74. The system according to claim 49 further comprising a sound sensor.

75. The apparatus according to any one of claims 1 and 42 further comprising a sensor selected from the group consisting of an accelerometer sensor, an ambient light sensor, an EMG sensor, an ECG sensor, and a skin impedance sensor.

76. The system according to claim 49 further comprising a sensor selected from the group consisting of an accelerometer sensor, an ambient light sensor, an EMG sensor, an ECG sensor, and a skin impedance sensor.

77. The apparatus according to any one of claims 1 and 42 further comprising a proximity sensor.

78. The system according to claim 49 further comprising a proximity sensor.

79. The apparatus as described in claim 1 further comprising a galvanic skin response sensor.

* * * * *